(12) United States Patent  
Maenle et al.

(10) Patent No.: US 7,369,304 B2
(45) Date of Patent: May 6, 2008

(54) CYTOLOGICAL AUTOFOCUSING IMAGING SYSTEMS AND METHODS

(75) Inventors: Garrick Maenle, Columbus, OH (US); William J. Knox, West Jefferson, OH (US); David Zahniser, Wellesley, MA (US)

(73) Assignee: Cytyc Corporation, Marlborough, MA (US)

( * ) Notice: Subject to any disclaimer, the term of this patent is extended or adjusted under 35 U.S.C. 154(b) by 247 days.

(21) Appl. No.: 10/008,379

(22) Filed: Nov. 5, 2001

(65) Prior Publication Data

US 2003/0179445 A1    Sep. 25, 2003

Related U.S. Application Data

(63) Continuation-in-part of application No. 09/430,198, filed on Oct. 29, 1999, now Pat. No. 7,006,674, which is a continuation-in-part of application No. 09/430,116, filed on Oct. 29, 1999, now Pat. No. 6,348,325.

(60) Provisional application No. 60/245,971, filed on Nov. 3, 2000.

(51) Int. Cl.
G02B 21/00    (2006.01)

(52) U.S. Cl. .................. 359/368; 359/383; 250/201.3; 382/128

(58) Field of Classification Search ................ 359/368, 359/383; 250/201.2, 201.3, 201.4; 382/128, 382/133, 134
See application file for complete search history.

(56) References Cited

U.S. PATENT DOCUMENTS

| 1,129,742 | A | 2/1915 | Sheaff |
| 3,600,057 | A | 8/1971 | Leffler |
| 3,951,512 | A | 4/1976 | Tolles |
| 4,000,417 | A | 12/1976 | Adkisson et al. |
| 4,011,004 | A | 3/1977 | Levine et al. |
| 4,103,643 | A | 8/1978 | Staunton |
| 4,159,875 | A | 7/1979 | Hauser |
| 4,199,748 | A | 4/1980 | Bacus |
| 4,407,570 | A | 10/1983 | Hayasaka |

(Continued)

FOREIGN PATENT DOCUMENTS

EP    0 849 765    6/1998

(Continued)

OTHER PUBLICATIONS

Brenner et al., "An Automated Microscope for Cytological Research: A Preliminary Evaluation," The Journal of Histochemistry and Cytochemistry, vol. 24, No. 1, pp. 100-111, 1976.*

(Continued)

Primary Examiner—Stephone B. Allen
Assistant Examiner—Lee Fineman
(74) Attorney, Agent, or Firm—Vista IP Law Group LLP

(57) ABSTRACT

The present invention relates to the analysis of specimens. Specifically, the invention relates to methods and apparatus for reviewing specimen slides, including apparatus for holding the slides. The invention also relates to an automatic focusing method for an imaging system and methods for accommodating vibration in the imaging system. In particular, the methods and apparatus may be applied to the automated analysis of cytological specimen slides.

38 Claims, 29 Drawing Sheets

U.S. PATENT DOCUMENTS

| | | |
|---|---|---|
| 4,508,435 A | 4/1985 | Graham et al. |
| 4,833,382 A | 5/1989 | Gibbs |
| 4,902,101 A | 2/1990 | Fujihara et al. |
| 4,907,158 A | 3/1990 | Kettler et al. |
| 4,965,725 A | 10/1990 | Rutenberg |
| 5,000,554 A | 3/1991 | Gibbs |
| 5,016,283 A | 5/1991 | Bacus et al. |
| 5,257,182 A | 10/1993 | Luck et al. |
| 5,287,272 A | 2/1994 | Rutenberg et al. |
| 5,315,700 A | 5/1994 | Johnston et al. |
| 5,333,207 A | 7/1994 | Rutenberg |
| 5,361,140 A | 11/1994 | Hayenga et al. |
| 5,386,318 A | 1/1995 | Kiihnert et al. |
| 5,408,535 A | 4/1995 | Howard, III et al. |
| 5,427,910 A | 6/1995 | Kamentsky et al. |
| 5,428,690 A | 6/1995 | Bacus et al. |
| 5,469,210 A | 11/1995 | Noguchi et al. |
| 5,473,706 A | 12/1995 | Bacus et al. |
| 5,499,097 A | 3/1996 | Ortyn et al. |
| 5,523,207 A | 6/1996 | Kamentsky et al. |
| 5,528,703 A | 6/1996 | Lee |
| 5,532,874 A | 7/1996 | Stein |
| 5,535,751 A | 7/1996 | Rz |
| 5,557,097 A | 9/1996 | Ortyn et al. |
| 5,561,556 A | 10/1996 | Weissman |
| 5,566,249 A | 10/1996 | Rosenlof et al. |
| 5,574,594 A | 11/1996 | Fowler et al. |
| 5,581,487 A | 12/1996 | Kelly et al. |
| 5,581,631 A | 12/1996 | Ortyn et al. |
| 5,587,833 A | 12/1996 | Kamentsky |
| 5,602,674 A | 2/1997 | Weissman et al. |
| 5,619,428 A | 4/1997 | Lee et al. |
| 5,621,519 A | 4/1997 | Frost et al. |
| 5,625,705 A | 4/1997 | Recht |
| 5,625,706 A | 4/1997 | Lee et al. |
| 5,627,908 A | 5/1997 | Lee et al. |
| 5,629,766 A | 5/1997 | Kaplan |
| 5,633,945 A | 5/1997 | Kamentsky |
| 5,638,459 A | 6/1997 | Rosenlof et al. |
| 5,642,433 A | 6/1997 | Lee et al. |
| 5,642,441 A | 6/1997 | Riley et al. |
| 5,647,025 A | 7/1997 | Frost et al. |
| 5,654,535 A | 8/1997 | Ortyn et al. |
| 5,655,029 A | 8/1997 | Rutenberg et al. |
| 5,659,421 A | 8/1997 | Rahmel et al. |
| 5,671,288 A | 9/1997 | Wilhelm et al. |
| 5,677,762 A | 10/1997 | Orten et al. |
| 5,677,966 A | 10/1997 | Doerrer et al. |
| 5,687,251 A | 11/1997 | Erier et al. |
| 5,690,892 A | 11/1997 | Babler et al. |
| 5,694,212 A | 12/1997 | Weissman |
| 5,715,327 A | 2/1998 | Wilhelm et al. |
| 5,717,778 A | 2/1998 | Chu et al. |
| 5,731,896 A | 3/1998 | Baumann et al. |
| 5,740,270 A | 4/1998 | Rutenberg et al. |
| 5,760,387 A | 6/1998 | Ortyn et al. |
| 5,763,871 A | 6/1998 | Ortyn et al. |
| 5,768,013 A | 6/1998 | Kraft |
| 5,781,667 A | 7/1998 | Schmidt et al. |
| 5,783,814 A * | 7/1998 | Fairley et al. ............ 250/201.3 |
| 5,787,188 A | 7/1998 | Nelson et al. |
| 5,787,189 A | 7/1998 | Lee et al. |
| 5,787,208 A | 7/1998 | Oh et al. |
| 5,790,308 A | 8/1998 | Kamentsky |
| 5,793,969 A | 8/1998 | Kamentsky et al. |
| 5,797,130 A | 8/1998 | Nelson et al. |
| 5,799,101 A | 8/1998 | Lee et al. |
| 5,812,692 A | 9/1998 | Rosenlof et al. |
| 5,825,670 A | 10/1998 | Chernoff et al. |
| 5,828,776 A | 10/1998 | Lee et al. |
| 5,833,794 A | 11/1998 | Mayer |
| 5,835,620 A | 11/1998 | Kaplan et al. |
| 5,841,124 A | 11/1998 | Ortyn et al. |
| 5,867,610 A | 2/1999 | Lee |
| 5,875,258 A | 2/1999 | Ortyn et al. |
| 5,889,880 A | 3/1999 | Doerrer et al. |
| 5,963,368 A | 10/1999 | Domanik et al. |
| 5,987,158 A | 11/1999 | Meyer et al. |
| 6,007,996 A | 12/1999 | McNamara et al. |
| 6,049,421 A | 4/2000 | Raz et al. |
| 6,096,271 A | 8/2000 | Bogen et al. |
| 6,134,354 A | 10/2000 | Lee et al. |
| 6,148,096 A | 11/2000 | Pressman et al. |
| 6,148,099 A | 11/2000 | Lee et al. |
| 6,151,139 A | 11/2000 | Haded et al. |
| 6,151,161 A | 11/2000 | Mayer et al. |
| 6,180,061 B1 | 1/2001 | Bogen et al. |
| 6,183,693 B1 | 2/2001 | Bogen et al. |
| 6,198,839 B1 | 3/2001 | Kuan et al. |
| 6,215,892 B1 * | 4/2001 | Douglass et al. ............ 382/128 |
| 6,226,392 B1 | 5/2001 | Bacus et al. |
| 6,249,593 B1 | 6/2001 | Chu et al. |
| 6,327,377 B1 | 12/2001 | Ruenberg et al. |
| 7,117,098 B1 * | 10/2006 | Dunlay et al. ................ 702/21 |

FOREIGN PATENT DOCUMENTS

| | | |
|---|---|---|
| EP | 0 849 765 A2 | 6/1998 |
| EP | 1 085 292 | 3/2001 |
| JP | 06-059194 | 3/1994 |
| JP | 08029693 | 2/1996 |
| JP | 09073033 | 3/1997 |
| JP | 09-179032 | 7/1997 |
| JP | 11-271638 | 10/1999 |
| JP | 2000-010015 | 1/2000 |
| JP | 2000-056229 | 2/2000 |
| WO | WO 89/07255 | 8/1989 |
| WO | WO 92/04651 | 3/1992 |
| WO | WO 98/32004 | 7/1998 |
| WO | 197 18 799 | 11/1998 |
| WO | WO 00/58690 | 10/2000 |

OTHER PUBLICATIONS

"Electric Inking Systems" http://www.xandex.com/Products/inker/electric.htm, pp.2.

Patent Abstract of Japan, vol. 1996, No. 6, Jun. 28, 1996 & JP 08 029693 (Nikon Corp) Feb. 2, 1996.

Patent Abstract of Japan, vol. 1997, No. 7, Jul. 31, 1997 & JP 09 073033 (Olympus Optical CO Ltd) Mar. 18, 1997.

Patent Abstract of Japan, vol. 1995, No. 2, Mar. 31, 1995 & JP 06 324269 (Canon Inc.) Nov. 25, 1994.

Patent Abstract of Japan, vol. 1996, No. 4, Apr. 30, 1996 & JP 07 333517 (Sumitomo Electric Inc Ltd) Dec. 22, 1995.

Olympus America Inc., "AcCell™ Cytopathology System" Version 1.0, (1996), 274 pgs.

Japanese office action and English translation for JP application No. 2005-539859, dated Jul. 27, 2007. (13 pages).

Correspondence dated Sep. 23, 2005, Examiner's First Official Report regarding Australian Patent Application No. 2002228837. (4 pages).

Correspondence dated Apr. 19, 2007, Response to Examiner's First Report regarding Australian Patent Application No. 2002228837 (43 pages).

Correspondence dated May 18, 2007, Examiner's Second Official Report regarding Australian Patent Application No. 2002228837. (2 pages).

Correspondence dated Jun. 18, 2007, First Response to Examiner's Second Official Report regarding Australian Patent Application No. 2002228837 (2 pages).

Correspondence dated Jun. 19, 2007, Second Response to Examiner's Second Official Report regarding Australian Patent Application No. 2002228837 (6 pages).

Correspondence dated Jun. 19, 2007, Notice of Acceptance regarding Australian Patent Application No. 2002228837 (3 pages).

PCT Notification of Transmittal of the International Search Report of the Declaration dated Oct. 1, 2002, forms PCT/ISA 210 and 220 for PCT/US01/46810, Applicant Cytyc Corporation (11 pages).

PCT Notification of Transmittal of the International Search Report of the Declaration dated Jan. 28, 2003, forms PCT/ISA 210 and 220, for PCT/US01/46810, Applicant Cytyc Corporation (13 pages).

PCT Invitation to Restrict or to Pay Additional Fees, dated Feb. 10, 2003, for PCT/US01/46810, form PCT/IPEA/405, Applicant Cytyc Corporation (4 pages).

Response to Invitation to Restrict or to Pay Additional Fees, dated Feb. 10, 2003, submitted on Mar. 8, 2003, for PCT/US01/46810, Applicant Cytyc Corporation (2 pages).

PCT Written Opinion dated May 20, 2003 for PCT/US01/46810, form PCT/IPEA/408, Applicant Cytyc Corporation (10 pages).

PCT Notification of Transmittal of the International Preliminary Examination Report, forms PCT/IPEA/406 and PCT/IPEA/409, dated Sep. 2, 2003, for PCT/US01/46810, Applicant Cytyc Corporation (11 pages).

European Communication Pursuant to Article 96(2) EPC, form EPO 2906, dated Jun. 1, 2007, for EP Application No. 01989956.6, Applicant Cytyc Corporation (3 pages).

* cited by examiner

CYTOLOGICAL AUTOFOCUSING IMAGING SYSTEMS AND METHODS

CROSS-REFERENCE TO RELATED APPLICATIONS

This application claims the benefit of provisional U.S. patent application Ser. No. 60/245,971, filed Nov. 3, 2000, U.S. patent application Ser. No. 09/430,198, filed Oct. 29, 1999, now U.S Pat. No. 7,006,674 and U.S. patent application Ser. No. 09/430,116, filed Oct. 29, 1999, now U.S. Pat. No. 6,348,325 the disclosures of which are hereby incorporated herein by reference in their entirety.

TECHNICAL FIELD

The present invention relates to systems and methods for the analysis of specimens. Specifically, the invention relates to a review system for reviewing specimens, methods of focusing the specimens in an imaging system, and apparatus for holding the specimen.

BACKGROUND INFORMATION

Cytology is the branch of biology dealing with the study of the formation, structure, and function of cells. As applied in a laboratory setting, cytologists, cytotechnologists, and other medical professionals make medical diagnoses of a patient's condition based on visual examination of a specimen of the patient's cells. A typical cytological technique is a "Pap smear" test, in which cells are scraped from a woman's cervix and analyzed in order to detect the presence of abnormal cells, a precursor to the onset of cervical cancer. Cytological techniques are also used to detect abnormal cells and disease in other parts of the human body.

Cytological techniques are widely employed, because collection of cell samples for analysis is generally less invasive than traditional surgical pathological procedures such as biopsies, whereby a tissue specimen is excised from the patient using specialized biopsy needles having spring loaded translatable stylets, fixed cannulae, and the like. Cell samples may be obtained from the patient by a variety of techniques including, for example, by scraping or swabbing an area, or by using a needle to aspirate body fluids from the chest cavity, bladder, spinal canal, or other appropriate area. The cell samples are placed in solution and subsequently collected and transferred to a glass slide for viewing under magnification. Fixative and staining solutions are typically applied to the cells on the glass slide, often called a cell smear, for facilitating examination and for preserving the specimen for archival purposes.

Typically, screening of cytological specimens has been a task for trained cytotechnologists and cytopathologists. Even though screening is done by highly trained individuals, the task is repetitive and requires acute attention at all times. Therefore, screening of cytological specimens is repetitive and tedious and would benefit from automation; however, the complexity and variety of material found in cytological specimens has proven very difficult to reliably examine in an automated fashion. Various image analysis systems have been developed for analyzing image data of specimens taken from a patient to augment the physician diagnosis of the biomedical status of the patient. For example, image analysis systems have been developed for obtaining image data representing blood cells, bone marrow cells, brain cells, etc. Image analysis systems are typically designed to process image data to determine characteristics of the specimen. These systems have been used primarily as prescreening systems to identify those portions of a specimen that require further inspection by a human, i.e., re-screening.

Methods and apparatus for re-screening slides are either very crude or entail great economic expense. The prevailing method in aiding relocation is the placement of an ink dot on the specimen near the location of the event. This method can be crude, awkward, time consuming, and inaccurate. In addition, with this method, it is not possible to ascertain if the entire specimen area of the slide has been uniformly examined or if areas of the specimen have or have not been scanned. It is, accordingly, often the case that if the user is interrupted, it is necessary to restart slide examination. Furthermore, with microscope examination of items for identifying characteristics, the use of ink dots can actually detrimentally impair examination of the item of interest.

In a laboratory, for example a cytology laboratory, a cytotechnologist examines numerous specimen slides under a microscope in order to analyze certain specimen cells of questionable nature. When such suspect cells are located, the cytotechnologist generally marks the slide at that point, so that he or she may recall the location of the cells at some later time for further examination. To date, cytotechnologists have marked slides generally by using one of several manual methods.

One such method exists where a cytotechnologist marks the area of the microscope slide in question with a marking pen. To accomplish this, the cytotechnologist must take his or her eyes away from the eyepiece of the microscope, move the microscope objective out of the way, peer under the nosepiece, estimate the location of interest on the slide, and then mark the slide with the pen. This method requires the cytotechnologist to refocus her eyes, move her body into a potentially awkward position, and to make a guess as to the placement of the mark. This method of marking can be time consuming and is typically not exact.

Another such method consists of marking a microscope slide by using an objective-like configuration marker. In this method, the cytotechnologist must take her eyes away from the microscope eyepiece, rotate the microscope nosepiece until the marking apparatus is in place, and then manually push the marking apparatus down onto the slide in order to mark the area in question. This method requires the cytotechnologist to refocus her eyes and to move her body into a potentially awkward position. Although this method is more exact than the previously described method, it is still tedious and time consuming.

Additionally, many imaging systems that can be used for imaging a specimen must be built to prevent vibration from affecting the imaging of the specimen. Image blur, due to vibration, results if the imaging system is not sufficiently rigid or dampened. A blurred image is typically unusable. Manufacturing a sufficiently rigid dampened system can be costly and adds weight and complexity to the imaging system.

Imaging systems also require apparatus for handling and holding specimens. Devices for holding specimens, slides, or similar objects in a defined position relative to an optical instrument, such as an imaging system, have been in existence for many years. In the instances of slide holding mechanisms, these features have been incorporated into the stages of automated microscopes so that a slide may be moved with the stage relative to the viewing field of the microscope. Many of these slide holding devices do not facilitate repeatably holding the slide in the same precise location in the slide holding area. In some environments, it may be desirable to view the slide through the imaging system on more than one occasion or to view the slide on different imaging devices. Being able to repeatably position a slide relative to a predefined coordinate system is a useful feature of the slide holder assembly.

In particular, when the platform holding the slide is undergoing repeated substantially planar motion to allow the imaging of selected regions of the slide, there needs to be a reliable system for the secure holding and release of a given slide. When large numbers of slides are used in an automated or semi-automated specimen analyzing apparatus, the ability to quickly load, secure, and remove slides from an imaging system in a precise and controlled way becomes an advantageous feature of large scale batch sample analysis.

In order for an automated system for analyzing a specimen on a sample slide to be effective, each image obtained should be in proper focus. Conventional focusing apparatus and methods, however, may be time-consuming, thereby making analysis of sample slides inefficient. Due to variations in distance between positions on the sample slide and imaging optics, focus should be adjusted accordingly during automated imaging of the slide. There is a need for a system that quickly and accurately focuses and scans substantially all of an area of interest of a sample slide. Imaging and analysis may accompany or follow such a scan, whereby specific regions of interest of the sample slide are automatically denoted and subsequently presented to a cytotechnologist, for example, for further analysis.

SUMMARY OF THE INVENTION

Generally, the invention addresses the problems outlined above by applying automated methods and related apparatus for screening specimens. Such methods and apparatus are used for holding the specimens, reviewing and marking specimens, efficient focusing of specimens, and compensating for vibration. The term specimen is used throughout the specification to represent the material being imaged and/or reviewed and is not limited to cytological material. Also, the terms specimen sample, and slide may be used interchangeably throughout the specification and figures.

In one aspect, the invention relates to an apparatus for marking a specimen. The apparatus includes an optical instrument, a marker coupled to the optical instrument and disposed outside a field of view of the optical instrument, and a stage coupled to the optical instrument for receiving the specimen. The stage moves the specimen between an inspection position in an optical path of the optical instrument and a marking position for marking the specimen with the marker. The optical instrument includes a motorized nosepiece, an illumination source, and focusing optics. The optical instrument can be in data communication with a computer. Alternatively, the optical instrument can be a laboratory microscope.

In various embodiments, the motorized nosepiece includes at least one lens and the lens can include a 10× objective. The motorized nosepiece can include a second lens and the second lens can include a 40× objective. The optical instrument can also include a specimen identification reader, which can be a bar code reader or an optical character recognition (OCR) device. Also, the marker can be a nib for applying a marking substance to the specimen. In some embodiments, the apparatus includes a cap mechanism coupled to the optical instrument and engageable with the marker. The cap mechanism is biased away from the marker when disengaged therefrom and actuatable into an engagement position with the marker by a pin disposed on the slide stage. The cap mechanism can include a resilient seal for sealing the nib of the marker. The apparatus can also include an actuator for moving the marker relative to the stage. The actuator can be a solenoid, a motor, a fluidic cylinder, or other suitable device.

In other embodiments, the apparatus can include a user interface control in electrical communication with the optical instrument and a console in electrical communication with the optical instrument. The user interface control can include at least one input device and a stage positioning device, such as a joystick. The input device can perform a variety of operations, such as advancing the specimen to a next position in a field of view of the optical instrument, advancing the specimen to a previous position in the field of view, toggling between the first lens and the second lens, and marking an object of interest. In addition, the user interface control can include four switches or other input devices, each performing one of the aforementioned operations. The console can include a keypad and a display. The apparatus can also include an audio output device in electrical communication with the optical instrument, such as a speaker for emitting an audible warning tone or instructions to a user.

In some embodiments, the apparatus also includes apparatus for electronically marking an object of interest within the specimen and an indicator for indicating marked status of a field of interest. The indicator includes an optical path originating at a light source and passing serially through a diffuser, a mask, an aperture, focusing optics, a lens, and a beam splitter. All of the elements are disposed within a housing. The light source can include two separate light sources. The optical instrument can further include a sensor for detecting presence of a specimen. The sensor can be a proximity switch, a limit switch, a hall-effect switch, a magnetic sensor, an optical sensor, or others suitable device.

In another aspect, the invention relates to a method of marking a specimen. The method includes the steps of positioning an object of interest within the specimen to a marking position, contacting the specimen with a marker, and actuating the specimen to create indicia thereon at least partially bounding the object of interest. The shape of the indicia can be line segments, arcs, and combinations thereof. In one embodiment, the specimen is disposed on a motorized stage and the method includes the step of actuating the motorized stage to position a cap mechanism into an engagement position for sealing the marker.

In yet another aspect, the invention relates to an automated method of reviewing a specimen. The method includes the steps of: (a) loading the specimen in an optical instrument; (b) locating a first datum mark on the specimen; (c) locating a second datum mark on the specimen; (d) establishing a coordinate system based, at least in part, on the first and second datum marks; (e) positioning the specimen to present a first field of interest; (f) moving to a next field of interest; (g) repeating step (f) until a predetermined number of fields of interest are presented; and (h) performing an autoscan of the entire specimen. In one embodiment, twenty-two fields of interest are presented. In some embodiments, the step of moving to a next field of interest includes inputting a user command.

In various embodiments, the method can include the step of electronically marking an object of interest located within the field of interest, which includes inputting a signal to a processor, determining if coordinate values for the object of interest are stored as a target zone within the processor, and adding the coordinate values of the object of interest to a list of marked target zones, if not previously stored. Alternatively, the step of electronically marking the object of interest includes inputting a signal to a processor, determining if coordinate values for the object of interest are stored as a target zone within the processor, and removing the coordinate values of the object of interest from a list of marked target zones, if the values are previously stored. The method can also include the step of indicating visually a marked status of the object of interest.

In addition, the method can include the step of physically marking an electronically marked object of interest, which includes inputting a signal to a processor, positioning the object of interest to a marking position, contacting the specimen with a marker, and actuating the specimen to create indicia thereon at least partially bounding the object of interest. Further, the step of performing the autoscan can be performed after all fields of interest are presented. The step of physically marking the specimen takes place after the autoscan is performed.

In some embodiments, the step of establishing a coordinate system includes centering the first datum mark, assigning a reference coordinate value to the first datum mark, storing in memory the first datum mark coordinate value, centering the second datum mark, assigning a reference coordinate value to the second datum mark, storing in memory the second datum mark coordinate value, and performing a coordinate transformation. The step of establishing a coordinate system can further include comparing the datum mark coordinate values to known, predetermined values to determine if the specimen is loaded in a proper orientation.

In other embodiments, the method can include the steps of reading a specimen identifier, accessing a specimen data record stored within the computer to obtain coordinate values for the object of interest, and updating the specimen data record to include the coordinate values of the electronically marked objects of interest. The method can further include the step of calibrating the marker prior to marking the specimen.

In some embodiments, the step of calibrating the marker includes focusing on an indicia disposed on the specimen, securing a marker into a holder coupled to the optical system, contacting the specimen with the marker, actuating the specimen to create a calibration mark thereon, creating an offset value for the marker by actuating the stage to position the calibration mark into a position relative to the indicia, recording the offset value, and applying the offset value to the marker position for future marks. Further embodiments include the marking step being performed after the entire specimen is scanned. Also, the autoscan step maybe performed after all fields of interest have been presented. The specimen could be cytological material disposed on a slide that is stained with a thionin-phenol solution. The phenol can be a phenol derivative.

In another aspect, the invention relates to a method of accommodating for vibration errors in an imaging system. The method includes the steps of acquiring vibration measurements of the imaging system while scanning portions of a specimen and re-imaging a portion of the specimen when the vibration measurement for the portion exceeded a predetermined threshold. In some embodiments, the method includes the step of rejecting the specimen if the vibration measurement for a predetermined number of portions exceeds the threshold or the step of rejecting the specimen if the vibration measurement exceeds a second threshold. In one embodiment, the vibration can be measured by an accelerometer disposed on the imaging system.

In another aspect, the present invention relates to a slide holder assembly that can be used with an imaging system. The assembly includes a base, a first platform, a second platform, at least one slide positioning member connected to the second platform, and an actuating mechanism attached to the base for moving the slide positioning member into and out of contact with a slide. The first platform is movably disposed on the base. The second platform is disposed on the first platform and includes a slide receiving area. The slide positioning member is operatively connected to the second platform. The actuating mechanism is disposed on the base. In various embodiments of the invention, the base can be coupled with an actuating table, and the actuating table can be coupled to an imaging system.

In some embodiments, the assembly can include two slide positioning members operatively connected to the second platform. The mechanism for actuating the slide positioning member can include a first a pin and a second pin for actuating the first and second slide positioning members, respectively. In other embodiments, the assembly can include at least one stop disposed on the second platform. The slide positioning members can each be connected to a resilient member to bias the slide positioning members towards the slide receiving area of the second platform. The slide positioning members can be rotatably mounted to the second platform and can position a slide in the receiving area into a contact position with the stop. In other embodiments, at least two stops are disposed on the second platform.

The slide positioning members themselves can be selected based on their material properties and then mounted on the slide holder assembly such that they are actuated independently of one another in various embodiments of the invention. The slide positioning members can be serially actuated with respect to one another. In addition, the slide positioning members can be actuated orthogonally with respect to one another. The positioning members can each include a substantially elongate arm with a mounting end and a slide contacting end.

According to other embodiments of the invention, the second platform can include a sensor disposed in the slide receiving area for detecting the presence of a slide. This sensor may be a hall-effect switch, a proximity switch, an optical sensor, a limit switch, or any other suitable sensor.

In other embodiments of the invention, the slide holder assembly can include a slide with a cytological specimen, where the specimen is located in a receiving area of the slide. This specimen can be stained with a conventional stain or a thionin-phenol stain solution. The thionin-phenol solution can include a phenol derivative.

According to an aspect of the invention, the automatic focusing and imaging of locations of specimens on sample slides allows thorough analysis of sample slides, such as biological or cytological sample slides, at accuracies and speeds much greater than would otherwise be possible. During the analysis of a slide, it is routinely necessary to readjust focus at various locations on the slide. Systems that are designed to automatically image substantially all of a region of interest of a slide need to enable the automatic adjustment of focus for various locations within that region of interest. A system which runs through a complete autofocusing procedure at every position it images may accurately image substantially all of a region of interest, but it is inefficient, since many of the autofocusing steps taken have been determined to be redundant and therefore unnecessary. Accordingly, this invention provides an automatic focusing method for an optical system that efficiently and accurately images a series of regions on the slide to address efficiently substantially all of the area of interest of the slide.

In one aspect, the invention relates to an automatic focusing method for an optical system that provides a way to efficiently and accurately image a series of regions on a specimen slide and cover substantially all of the areas of the specimen. One embodiment of the invention involves a method for establishing a global focal plane for the sample slide in order to account for tilt of the slide due to deviations from pure normality to the optical path of the imaging optics. This can occur due to normal assembly tolerances of the slide holder, optical system wear, and slide loading or holding misalignment. In establishing the global focal plane, another embodiment of the invention provides a check of the slope along an index axis and the slope along a scan axis of the slide, to determine whether a predetermined threshold is exceeded. In this embodiment, if the threshold is exceeded, the slide is flagged to indicate the problem and appropriate corrective action can be taken.

Another embodiment of the invention involves a method of performing a scan pass across the surface of a slide in which a coordinate is determined that provides a focus value within a predetermined range of an optimal focus value for a position on the slide. The coordinate is recorded, and may be later retrieved. This coordinate may be expressed, for example, in a Cartesian coordinate system as the focus axis coordinate or z-coordinate, corresponding to the (x,y) point that corresponds to a respective position on the sample slide in a plane of the sample slide. It should be noted, however, that the invention also applies to configurations other than those involving a planar sample slide and may be applied using coordinate systems other than the Cartesian coordinate system, such as biradial, spherical, or cylindrical coordinate systems, among others.

Another embodiment of the invention involves a method of determining an area of fine focus jurisdiction around a position on a slide at which a corresponding value of a coordinate that provides a focus value within a predetermined range of an optimal focus value has been determined. For instance, once a z-coordinate has been determined by successive adjustments of an element of the optical system imaging a position on the slide, the same z-coordinate will provide adequately in-focus images for positions in a given area surrounding that point on the slide. An embodiment of the invention provides that an area of fine focus jurisdiction is elliptical in shape. Another embodiment provides that an area of fine focus jurisdiction has a major axis substantially parallel to a scan axis of the optical system and a minor axis substantially parallel to an index axis of the optical system.

Another embodiment of the invention involves the determination of a second coordinate that provides a focus value within a predetermined range of an optimal focus value for a second position on a slide. This embodiment determines whether the second point lies within at least one previously-determined area of fine focus jurisdiction, and if not, determines an area of fine focus jurisdiction surrounding the second point. This embodiment optionally additionally includes the performance of a fine focus action to determine a coordinate providing sufficient focus at the second position.

Another embodiment provides for the use of a global focal surface of the slide in determining a first estimate of a coordinate providing adequate focus. For example, tilt of the slide may be accounted for in estimating a suitable focus axis coordinate.

Yet another embodiment provides for the determination of whether a second point lies within at least one area of fine focus jurisdiction and the retrieval of the coordinate(s) correlated with this/these area(s). For example, if one or more previously-determined z-coordinates apply over a certain region of a slide, the method will retrieve these coordinates instead of performing a new fine focus action, thereby saving the time associated with performing unnecessary steps. An additional embodiment provides for the adjustment of a retrieved value according to the global focal surface of the slide.

Yet still another embodiment obtains a weighted average of retrieved coordinates for a position on the slide corresponding to a point lying within more than one fine focus jurisdiction. An additional embodiment provides for the adjustment of this value according to the global focal surface of the slide.

Another embodiment searches for previously-measured coordinate values only from among those within a bin wherein a given point lies. In this way, the process may be made more efficient. Still another embodiment determines whether or not a given position is within an area of interest of a slide. Another embodiment combines elements of the embodiments described above in various combinations and permutations and systematically images substantially the entire area of interest of a slide in a step-by-step fashion.

Still another embodiment provides for an automatic focusing method involving two kinds of focus actions—an initial coarse focus and subsequent fine focuses. The initial coarse action is a more thorough procedure than the fine focus actions and may provide a baseline coordinate used to enable quicker performance of the subsequent fine focus actions. Another embodiment limits the number of times the slide is imaged at a particular position to five.

These and other objects, along with advantages and features of the present invention herein disclosed, will become apparent through reference to the following description of embodiments of the invention, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Embodiments of the present invention are described below. It is, however, expressly noted that the present invention is not limited to these embodiments, but rather the intention is that modifications that are apparent to the person skilled in the art and equivalents thereof are also included.

The review system ("RS") defines apparatus used by a cytotechnologist or cytopathologist (collectively "user") to view a slide having a cytological specimen disposed thereon. The review can be through either a customized optical instrument or a traditional microscope interface that utilizes automatic slide movement. The automatic movement presents fields of interest identified by an imaging system. Additionally, the review system provides a method for automated marking of objects for later review. The marking may be electrical, physical, or both.

Generally, when a user places a specimen on the RS for review, they are presented a plurality of fields of interest ("FOIs") that were previously identified by an imaging system and stored in a computer server. In one operational state, the RS requires that each of the identified FOIs be presented to the user before the user can complete the review of the specimen. As each of the FOIs is being presented, the user can electronically mark the contents of a target zone within an FOI for subsequent physical marking. Upon completing the electronic marking process, the RS can physically mark each electronic location (marked target zone) with a translucent marking dye. The actual details of marking are discussed hereinbelow. An electronic file representing the specimen details and provided earlier by the server is used and updated by the RS and maintained on the server.

Figure 1:
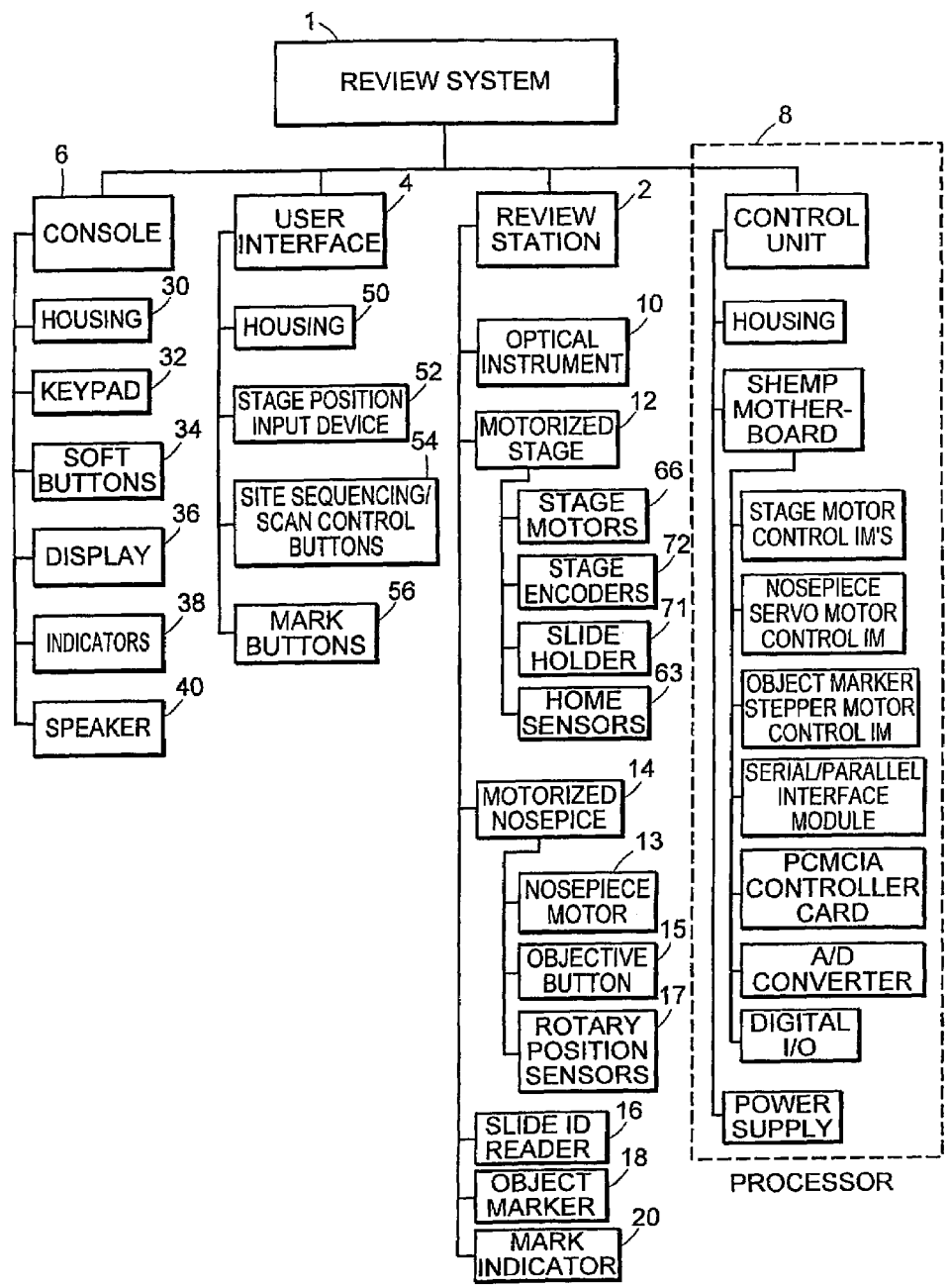
FIG. 1 is a graphical representation of one embodiment of a review system in accordance with the invention.

The RS subsystem architecture is shown graphically in FIG. 1, which illustrates the functional breakdown of the elements in the RS 1 into subsystems. Generally, the elements of the RS 1 include a review station 2, a user interface 4, a console 6, and a processor 8, all of which are described in greater detail hereinbelow. The elements are in electrical, mechanical, or data communication with one another. In some instances, the elements are in a combination of electrical, mechanical, and data communication.

Figures 2, 2A:
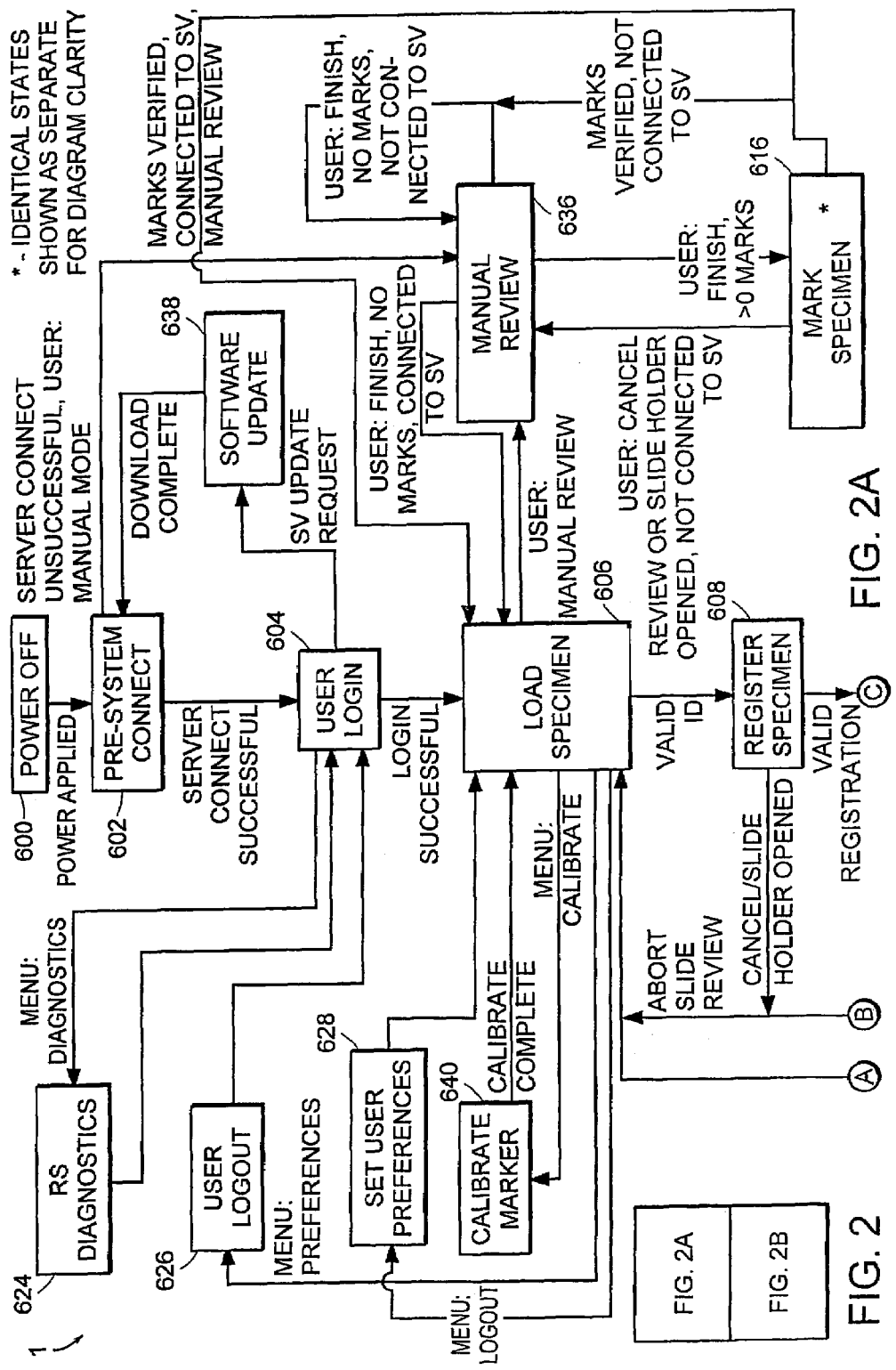
FIG. 2, including
FIGS. 2A and 2B, is a flow chart illustrating the operational modes of the review system of FIG. 1.
Figure 2B:
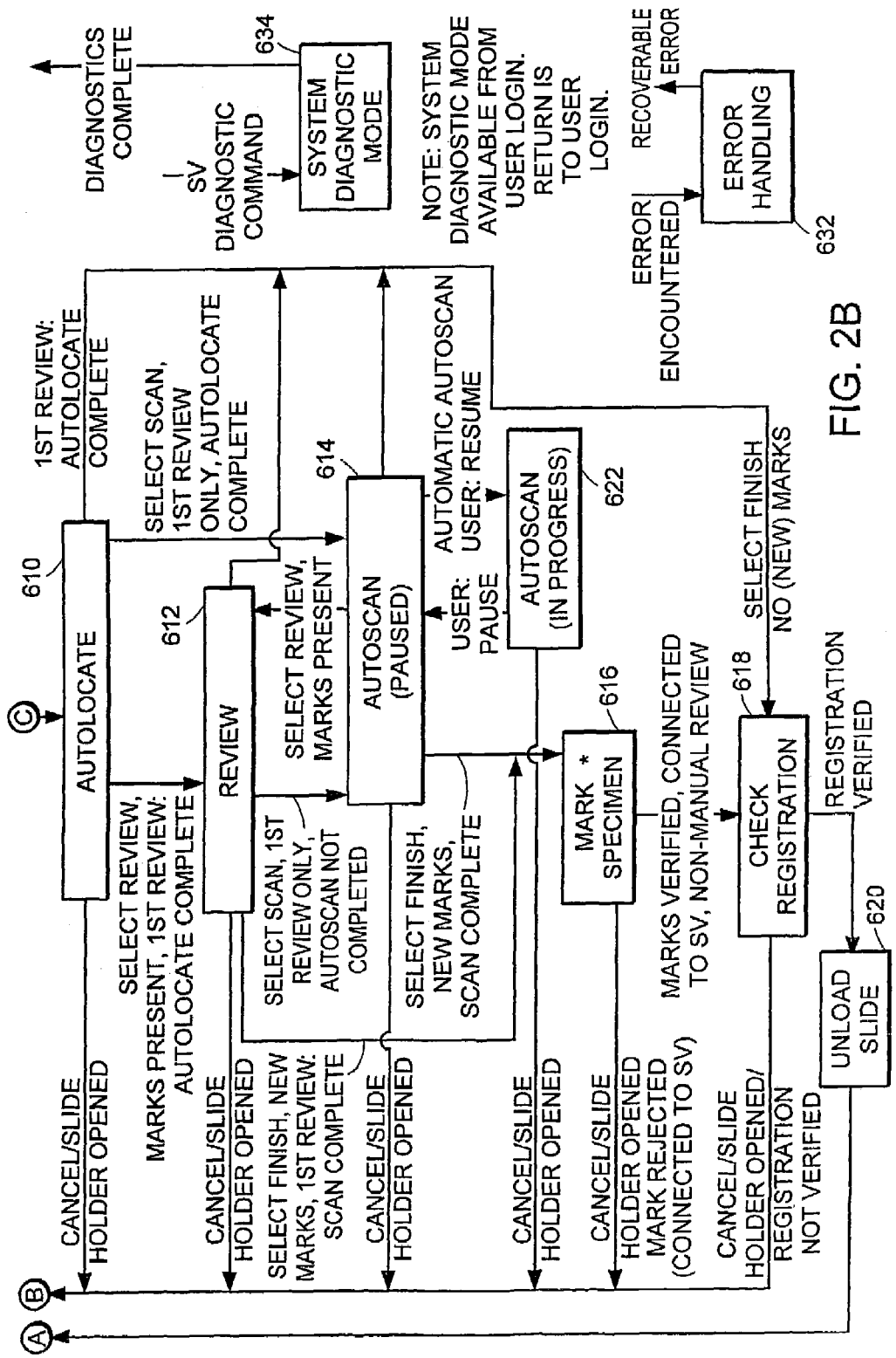
Figure 3:
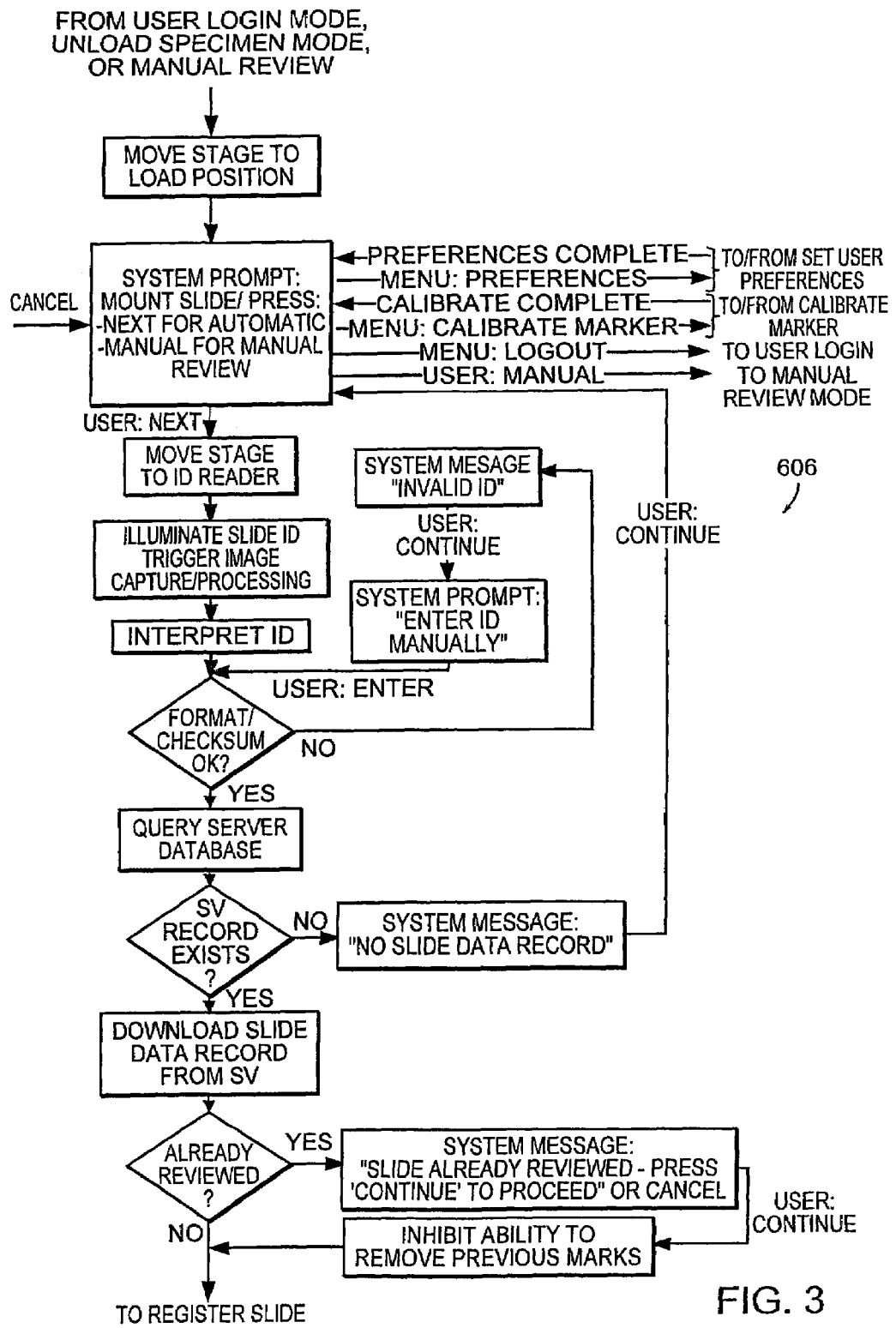
FIG. 3 is a flow chart illustrating the operational mode of loading a slide into a review system.

FIG. 2 illustrates the relationship of the various RS operational modes and FIG. 3 illustrates the functions that the RS 1 performs during the load specimen mode 606. Referring generally to FIG. 2, the functional aspects of the various operational modes will be described. There are a number of functions that are enabled in more than one mode and function identically. The various modes include: power off 600, pre-system connect 602, user login 604, load specimen 606, register specimen 608, autolocate 610, review 612, autoscan 614, 622, mark specimen 616, check registration 618, and unload specimen 620. The power off mode 600 is when there is no power applied to the RS 1. Upon the application of power, the RS 1 transitions to the pre-system connect mode 602. The pre-system connect mode 602 represents RS operation prior to connection to the server. The pre-system connect mode 602 includes a power on self test ("POST").

The POST functions include ram check, processor check, audible/visual indicator tests, console/user interface presence test indicating to the user via the console that the RS 1 is initializing stage motor homing sequence, nosepiece motor homing sequence, object marker test, and specimen ID reader test. If the POST is successful (all elements pass), the RS 1 initiates connection with the server; however, if the POST is unsuccessful, the RS 1 transitions to an error handling mode 632. If the server connection is successful, the RS 1 can download lab preferences from the server and transition to the user login mode 604. If, after a predetermined time, the server connection is still unsuccessful, the RS 1 can warn the user that the server connection was unsuccessful and prompt the user to enter a manual review mode 636 or try to re-establish connection with the server. If the user selects 're-try', the RS 1 reenters the pre-system connect mode 602. If the user selects manual review mode 636, the RS 1 moves the specimen to a load position, prompts the user to load a specimen and confirms by inputting a signal, and transitions into manual review mode 636 upon receipt of an input signal.

During the user login mode 604, the user logs into the RS 1 and the user's preferences are downloaded from the server. Specifically, the RS 1 can prompt the user to enter a login ID via a keypad and press the enter key. During user ID entry, the RS 1 can display the ID in hidden format (placeholders only) and the backspace key can function as a single character delete. After the user presses the enter key following ID entry, the RS 1 queries the server database and, if the ID exists, set user preferences locally according to the server response and transition to the load specimen mode 606. If the ID does not exist, the RS 1 emits an audible tone, warns the user ("Invalid ID") via the display, delays and then returns to user login mode 604. If the RS 1 receives a broadcast message from the server informing it of pending software update activity, the RS 1 can return a response to the message and transition to a software update mode 638. If the RS 1 receives a broadcast message from the server informing it of pending system diagnostic activity, the RS 1 can return a response to the message and transition to a system diagnostic mode 624, 634.

The load specimen mode 606 (FIG. 3) begins with the RS 1 waiting for the user to load a specimen. The specimen ID is read automatically by the ID reader or input manually from the keypad if the automatic read fails. If the ID corresponds to a valid record on the server corresponding to an imaged specimen, the RS 1 proceeds with registration, otherwise the RS 1 continues with manual review. The RS 1 can enable the cancel key on the console during manual slide ID entry. The RS 1 can also enable a specimen presence sensor. The RS 1 can move the stage to the specimen load position and prompt the user to load a slide and input a signal via the user interface to confirm the start of an automated slide review or start manual review. Upon receipt of the input signal confirming the start of automated slide review, the RS 1 can move the stage such that the specimen ID is positioned under the specimen ID reader. The RS 1 then sends a message to the specimen ID reader to initiate the illumination of the specimen label, as well as the capture and processing of an image. The RS 1 interprets the specimen ID string received. If the specimen ID has a valid format/checksum, operation continues with the RS 1 querying the server for existence of a specimen data record with this slide ID. If there was a "bad read" or if the format/checksum are invalid, the RS 1 displays an invalid slide ID message, issues an audible tone, and waits for the user to press the continue key on the console.

Upon receipt of the continue instruction, the user manually enters the specimen ID (including checksum) via the console or cancels the specimen review. During manual specimen ID entry, the RS 1 can display the specimen ID. During manual specimen ID entry, the backspace key can function as a single character delete. Upon receipt of the specimen ID, the RS 1 can interpret the manually entered specimen ID. If the specimen ID has a valid format/checksum, operation resumes with the RS 1 querying the server for existence of a specimen data record with this slide ID. If the format or checksum is invalid, the RS 1 displays an invalid specimen ID message and issues an audible tone.

Once operation resumes, the RS 1 queries the server for existence of a specimen data record with the corresponding specimen ID. If the server response to the database query indicates the presence of a specimen data record ("SDR") corresponding to this specimen ID, the RS 1 downloads the number of fields of interest ("FOIs"), the locations (in Image Processor ("IP") coordinates) of the FOIs, the locations (in IP coordinates) of the fiducial marks, the locations (in IP coordinates) of the marked target zones from previous reviews (if any), the location (in IP coordinates) of the specimen cell spot center, the specimen cell spot diameter, and the specimen reviewed status. If the server response to the database query indicates a communication error or that there is no slide data record corresponding to this slide ID, the RS 1 can issue an appropriate warning on the console, emit an audible tone, and instruct the user to press the continue key to cancel slide review.

After the RS 1 has downloaded the specimen data record, the RS 1 checks to see if the specimen has already been reviewed. If the specimen was previously reviewed, the RS 1 will display a warning message, emit an audible tone, inhibit the unmarking of target zones marked in previous reviews, and request confirmation that the user wishes to proceed. The RS 1 waits for this confirmation, then transitions to the register slide mode. If the specimen was not previously reviewed, the RS 1 transitions directly to the register specimen mode 608.

In the register specimen mode 608, the RS 1 establishes the registration of the specimen by having the user center each of two fiducial marks in an area cradled by a mark indicator in the field of view ("FOV"). Having the coordinates of the fiducial marks in both IP (from the SDR) and review station systems, the RS 1 then computes and performs a coordinate transformation on the field of interest ("FOI") data obtained from the server. The specimen presence sensor is enabled during the specimen registration mode. The RS 1 illuminates a white mark indicator and presents the first fiducial mark within the FOV with the objective at 10×. The RS 1 then enables the specimen position input device ("SPID") for manual stage positioning limited to about plus or minus half an FOV (e.g., 1100 µm) along either of the two slide stage motion axes (x, y). The RS 1 prompts the user to use the SPID to center the first fiducial mark within the mark indicator and enter a next command when the operation is complete. Upon confirmation, the RS 1 presents the second fiducial mark (position derived from the SDR plus the offset recorded in centering the first fiducial mark) and prompt the user to use the SPID to center it within the mark indicator and enter the next command when the operation is complete or enter a previous command to go back to the first fiducial mark. Upon receipt of the previous command, the RS 1 returns to the location of the user-centered first fiducial mark. Upon confirmation that the alignment of the second fiducial mark is complete, the RS 1 computes a coordinate transformation from IP to review station based upon the fiducial mark coordinates as recorded in the SDR and as located at the review station by the user. The RS 1 also applies the coordinate transformation to each FOI location, marked target zone, and the specimen cell spot center, and then transitions into autolocate mode 610.

In the autolocate mode 610, the user is presented with a predetermined number of FOIs using the 10× objective. At any time while in this mode, the user may mark/unmark target zones, manually move the stage using the SPID, and toggle the objective lens. Autolocate is complete when all FOIs have been presented. On the initial review of the specimen, autolocate is typically completed before the user is permitted to review marked target zones, perform an autoscan or complete specimen review.

During the autolocate mode 610, the RS 1 indicates the current mode and progress, (e.g., "1 of 30") on the display and instructs the user (via the display) on how to transition to the next or previous FOI. The RS 1 presents the first FOI in the FOV and enables the SPID for user-directed positioning of the stage. The RS 1 enables electronic marking/unmarking and mark indication while the objective is at 10× The RS 1 also enables changing of magnification and the specimen presence sensor.

The next and previous inputs on the user interface allow the user to change the objective lens to 10×, if not already at 10×, position the stage at the next or previous FOI, update the autolocate mode progress indicator (e.g., "3 of 30") on the display, and instruct the user (via the display) on how to transition to the next or previous FOI. If the user enters next when the current FOI is the last FOI (e.g., all FOIs have been presented), the RS 1 emits an audible tone and indicates on the display, as part of the status of specimen review, that autolocate is complete, if this has not already been done. The RS 1 ignores a previous command if the present FOI is the first FOI. The previous command may be accompanied by a warning, such as a an audible tone.

If the user commands a change to the review mode 612 (e.g., via a review key on the console), the RS 1 changes the objective lens to 10× (if necessary) and transitions into review mode 612. In one embodiment, a user can only change to review mode 612 if the number of marked target zones is greater than zero and the initial autolocate review of the specimen has been completed. If the user commands a change to the autoscan mode 614, 622 (e.g., via a scan key), the RS 1 changes the objective lens to 10× (if necessary) and transitions into autoscan mode paused 614. In one embodiment, autoscan can only be selected on the initial review of the specimen and only if the autolocate mode 610 is complete. If the user enters a finish command during the initial review of the specimen, the RS 1 changes the objective lens to 10× (if necessary) and transitions to the check registration mode 618. During a subsequent review of the specimen, when there are new electronic marks, the RS 1, in response to the finish command, changes the objective lens to 10× (if necessary) and transition to the mark specimen mode 616. If during a subsequent review of the specimen, when there are no new electronic marks, the RS 1, in response to the finish command, changes the objective lens to 10× (if necessary) and transitions to the check registration mode 618.

In the review mode 612, electronically marked target zones from the current specimen review, as well as marked target zones from previous reviews, are presented to the user using the 10× objective. The RS 1 indicates the current mode and progress on the display, instructs the user (via the display) on how to transition to next/previous marked target zones, and presents the first marked target zone (from the first slide review if this is a subsequent review) in the FOV. In addition, the RS 1 enables the SPID for user-directed positioning of the stage, electronic marking/unmarking while the objective is at 10×, mark indication while the objective is at 10×, and changing of magnification.

During the review mode 612, all the electronically marked target zones, including any marks from previous slide reviews, are available for presentation. The order of presentation of marked target zones may be, for example, chronological, such as in the order target zones were marked. Alternatively, the presentation order of the marks may be geographic based. When the user enters a next or previous command via the user interface, the RS 1 changes the objective lens to 10×, if not already at 10×, positions the stage at the next or previous (respectively) marked target zone, updates the review mode progress indicator (e.g., "2 of 5") on the display, and instructs the user on how to transition to a next or previous marked target zone. The RS 1 ignores the next command if the present marked target zone is the last marked target zone. The RS 1 also ignores the previous command if the present marked target zone is the first marked target zone. The RS 1 may generate a warning, such as a an audible tone.

If the user commands a change to the autoscan mode 614, 622, the RS 1 moves to the scan start position if an autoscan has not yet been initiated or moves to the current scan position if an autoscan has already been initiated. The RS 1 subsequently transitions into autoscan paused mode 614. Typically, the user may only command a change to the autoscan mode 614, 622 during an initial specimen review and only if the autoscan has not been completed. If the user enters a finish command during the initial review of the specimen, the RS 1 changes the objective to 10× (if necessary) and transitions to the mark specimen mode 616. If the user enters a finish command during a subsequent review of the specimen and there are new electronic marks, the RS 1 changes the objective to 10× (if necessary) and transitions to the mark specimen mode 616. If the user enters a finish command during a subsequent review of the specimen and there are no new electronic marks, the RS 1 changes the objective to 10× (if necessary) and transitions to the check registration mode 618.

Autoscan mode 614, 622 implements an automated full scan of the specimen cell spot with the 10× objective in place. Autoscan may be automatic or user-triggered. In an automatic autoscan, motion is initiated by the RS 1 and may be paused and resumed by the user. While paused, the user can use the SPID for manual positioning and mark/unmark as in autolocate and review modes 610, 612. The scan resumes where it left off when the user enters a next or resume command. The motion profile for an automatic autoscan may be continuous, consisting of a series of overlapping scan-lines (during which the scan speed can be controlled dynamically by the SPID) or intermittent (i.e., start-stop), consisting of a series of movements to discrete, overlapping FOVs and including a pause at each FOV, the duration of which can be controlled dynamically by the SPID.

The user-triggered autoscan is identical to a start-stop automatic autoscan, except that the user initiates the transitions to successive FOIs by entering a next or previous command. In addition, the autoscan direction can be horizontal or vertical, according to the user's preference. The autoscan is complete when the entire sequence of moves to scan line endpoints (or discrete FOV) has been completed. In one embodiment, a first review of a specimen requires the entire autoscan to be completed if there are any electronic marks. Generally, the autoscan should cover 100% of the specimen cell spot with overlap between FOVs.

At the start of the autoscan mode 614, 622, the RS 1 calculates the end points of all the moves that constitute the scan based upon the cell spot center from the SDR and the selected motion profile (start-stop or continuous) and orientation (horizontal or vertical). The RS 1 moves to the scan start position. In addition, the RS 1 indicates autoscan progress and paused condition on the display (e.g. "scan paused –25% complete"), which will prompt the user to enter the next or resume command to begin/resume the scan if the scan is not complete. The RS 1 also enables the SPID for user-directed positioning of the stage, the electronic marking/unmarking function while the objective is at 10×, the mark indication function while the objective is at 10×, and the changing of magnification. If the user enters a reset command during autoscan, the RS 1 moves to the scan start position and cancels the scan in progress.

If the user enters the previous command during automatic start-stop autoscan, the RS 1 backs the stage up one FOI, if the current scan position is not the scan start position and the scan is not complete. When the user enters a next or resume command during a user-triggered autoscan and the scan is not complete, the RS 1 moves to the next FOI and updates autoscan progress on the display. When the user enters the next or resume command and the scan are complete, the RS 1 emits an audible tone. When the user enters a pause or previous command and the current scan position is not the scan start position, the RS 1 moves to the previous FOI and updates the autoscan progress on the display. When the user enters the pause or previous command and the current scan position is the scan start position, the RS 1 emits an audible tone.

If the user commands a change to the review mode 612 when the number of marked target zones is greater than zero, the RS 1 changes the objective to 10× (if necessary), stores the current scan position, and transitions into review mode 612. If there are marks and the user enters the finish command, the RS 1 transitions to the mark specimen mode 616. If there are no marks and the user enters the finish command, the RS 1 transitions to the check registration mode 618.

When the user enters a next or resume command during an automatic autoscan and the scan is not complete, the RS 1 changes the objective lens to 10× (if necessary), moves the stage to the current stored scan position (in case user-directed positioning occurred), and transitions to an autoscan in progress mode 622. Autoscan in progress mode 622 is when automatic scanning is underway and operation has not been paused by the user. It is typically only entered during an automatic (continuous or start-stop) autoscan.

During a continuous autoscan, the RS 1 moves to the end point of the first (present) scan line at a speed defined by the user. When the X-axis of the SPID is deflected to the right, outside a pre-defined deadband zone, the RS 1 continuously adjusts the scan speed upward. Conversely, when the X-axis of the SPID is deflected to the left, the RS 1 adjusts the scan speed downward. After completion of each scan line, the RS 1 updates the autoscan progress indicator on the display.

During a start-stop autoscan, the RS 1 moves to the first (next) FOI at a speed defined by the user and waits there for a dwell time defined by the user. When the X-axis of the SPID is deflected to the right, outside a pre-defined deadband zone, the RS 1 continuously adjusts the dwell time downward. Conversely, when the X-axis of the SPID is deflected to the left, the RS 1 adjusts the dwell time upward. After arrival at each FOI, the RS 1 updates the autoscan progress indicator on the display.

During either a continuous scan or a stop-start scan, the velocity of inter-scan line moves is at the FOI-to-FOI speed defined by the user. The RS 1 continues moving to FOIs until the final scan line end point or FOI is reached, at which time the RS 1 transitions to autoscan paused mode 614. When the user enters a pause or previous command prior to scan completion, the RS 1 pauses stage motion, stores the current scan position, and transitions to autoscan paused mode 614.

In the mark specimen mode 616, physical marks are made on the specimen in batch fashion by an object marker at the locations of the electronic marks made during the present specimen review. The physical marks are then individually presented to and verified by the user. The mark indicator cursor illuminates green to indicate that electronically marked target zones exist. Upon entering the mark specimen mode 616, the RS 1 translates the electronically marked target zone coordinates into object marker coordinates using the current translation values for the object marker obtained during the most recent object marker calibration. For each target zone electronically marked during the current review session (typically in the order in which it was electronically marked) the RS 1 positions the stage (as necessary) for marking, and creates stage motion (as necessary) and marker motion sufficient to make the physical mark on the specimen. For each target zone physically marked during the current review session, the RS 1 presents the physical mark with the objective at 10× and prompts the user to enter a next command to verify the mark or enter a reject command if it is not verifiable.

If the user enters reject for any mark, the RS 1 prompts the user to confirm that the mark is to be rejected by inputting a yes or no command, which typically involves pressing the 'Y' or 'N' key on the keypad. Upon receipt of the yes command, the RS 1 indicates via the display that the mark has been rejected, emits an audible tone, and waits for the user to enter a continue command, after which the RS 1 transitions to the load specimen mode 606. In one embodiment, the RS 1 prompts the user to erase all physical marks. Upon receipt of the no command, the RS 1 restores the prior operational state. When the user verifies the last of the physical marks, typically by entering a next command, the RS 1 caps the marker, if the marker was equipped with a cap, and transitions to the load specimen mode 606 if this is a manual review and to the check registration mode 618 otherwise.

If the user enters a cancel review command, the RS 1 transitions to the manual review mode 636 accompanied by a warning, for example, suggesting that the user calibrate the marking device and/or an audible tone. When marks are present, the RS 1 additionally prompts the user to erase all physical marks. When the user verifies the last of the physical marks, the RS 1 transitions to manual review mode 636.

In the check registration mode 618, the registration that was established at the beginning of the specimen review in the register specimen mode 608 is verified. Verification of registration confirms accurate presentation of all FOIs, as long as the specimen did not move and later recover position during specimen review. The RS 1 illuminates the white mark indicator cursor. For each of the two fiducial marks, the RS 1 positions the stage at the position the user indicated in the register specimen mode 608 with the objective at 10× and prompts the user to confirm the alignment of the first fiducial mark in the target zone by entering the next command or reject registration by entering the reject command.

If the user enters the reject command after the presentation of either fiducial mark, the RS 1 displays a warning (e.g., mark rejected), emits an audible tone, turns off the mark indicator, and/or prompts the user to enter the continue command. When marks are present on the initial review, the RS 1 additionally prompts the user to erase all physical marks. After entry of the continue command, the RS 1 transitions to the load specimen mode 606. If registration is verified, which the user can indicate by, for example, entering the next command twice in succession, the RS 1 turns off the mark indicator and transitions to the unload specimen mode 620.

In the unload specimen mode 620, the RS 1 uploads the updated SDR information to the server and makes a specimen reviewed mark on the specimen boundary arc. In addition, the RS 1 transforms the marked target zone locations from the present review (new marks) back into the IP coordinate system by reversing the transformation performed during the register specimen mode 608 and updates the SDR on the server with the time of the start of specimen review, the total number of marked target zones (any new plus any old, and the new marked target zone locations in IP coordinates), and the time of the completion of specimen review (present time).

If the review was the first review of the specimen, the RS 1 positions the stage for creation of the specimen reviewed mark, uncaps the pen or marker, creates the stage motion and the marker motion as necessary to make the specimen reviewed mark on the specimen boundary arc, caps the pen, moves the stage to the specimen load position, emits an audible tone, and prompts the user to unload the specimen. When the specimen is removed, as detected by a specimen presence sensor, the RS 1 transitions to the load specimen mode 606.

Other operational modes include user logout 626, set user preferences 628, error handling 632, marker calibration 640, software update 638, manual review 636, and diagnostics 624, 634. In the user logout mode 626, the user logs out of the RS 1. The RS 1 prompts the user to confirm log out, for example, by entering a yes or no command. If the user enters the yes command, the RS 1 uploads the user's preferences to the server and transitions to the user login mode 604.

During the set user preferences mode 628, the user is able set her operational preferences, including autoscan settings and maximum speed for manual positioning. For each user-settable preference, the RS 1 indicates to the user via the display the current setting of the parameter and how to change the setting to the desired value. The setting is stored locally until the user preferences are updated on the server during the user logout mode 626. Other user settable preferences include, but are not limited to, scan type, scan direction, autolocate, input setup, and SPID setup. By way of example only, the scan type settings can include auto continuous, auto start-stop, or user-triggered start-stop; the scan direction can include left-right or up-down; autolocate settings can include the FOI-to-FOI speeds; and the SPID settings can include user-based or specimen-based.

At any time during the set user preferences mode 628, except when running a test, if the cancel command is entered, the RS 1 transitions to the load specimen mode 606. The RS 1 will not save any changes that were not followed by entering a save command. When running a test, if the cancel command is entered, the RS 1 stops all motion, cancels the test, and returns to the menu displayed before entering the test command.

The error handling mode 632 is a special mode that handles errors within the RS 1. This mode can be entered from any mode except the power off mode 600. Within the error handling mode 632, the RS 1 assesses the error and takes appropriate action. If the error does not prevent the system from continuing to operate, the RS 1 takes appropriate action and transitions back to the appropriate mode.

In the marker calibration mode 640, the position of the mark created by the marker is calibrated, for example, by being aligned with the stage coordinate system. This procedure may be performed at a variety of times, for example, every time a new marker is installed, after an error is encountered while verifying marks, or at least once per user session. During the marker calibration mode 640, the RS 1 prompts the user to load a blank specimen slide and confirms the slide is loaded by entering a next command. Upon confirmation of slide load, the RS 1 makes a test mark on the slide at predetermined coordinates, presents the test mark to the user using the 10× objective, and illuminates the white mark indicator. Further, the RS 1 prompts the user to use the SPID to center the test mark within the mark indicator and confirm when the operation is complete. Upon confirmation of the test mark, the RS 1 generates the coordinate translation values ($\Delta X$, $\Delta Y$) or geometric offsets for the marker. The RS 1 then emits an audible tone, indicates completion of marker calibration on the display, and waits for the user to enter a continue command, after which the RS 1 transitions to the load specimen mode 606.

The software update mode 638 enables the server to download and install new software on the RS 1. All system functionality is typically locked out until the software update is complete. Upon completion of the software update, the RS 1 returns a message to the server and transitions to the pre-system connect mode 602.

The manual review mode 636 allows the user to control the motorized stage, the motorized nosepiece, and the marker. The user is able to electronically mark/unmark and physically mark target zones, as well as review the electronically marked target zones. Upon entry into the manual review mode 636, the RS 1 moves the stage to the specimen load position and prompts the user to load a specimen. After manually inputting a command to the RS 1, the stage moves to a nominal location on the specimen for the start of the manual review.

During review, when the user enters a next or previous command, the RS 1 changes the objective lens to 10×, if not already at 10×; positions the stage at the next or previous marked target zone, if any marked target zones exist; emits an audible tone if no marked target zones exist or if the user enters the next command while at the last marked target zone or enters the previous command while at the first marked target zone; and updates the marked target zone status indicator on the display.

If the user enters the finish command and there are electronic marks, the RS 1 transitions to the mark specimen mode 616. If the user enters the finish command and there are no electronic marks, the RS 1 transitions to the load specimen mode 606. In an alternate embodiment, opening the specimen holder causes the RS 1 to clear all electronic marks and re-enter the manual review mode 636. When the user subsequently enters a cancel command, the RS 1 clears all electronic marks and re-enters the manual review mode 636. If the user enters a finish command and there are electronic marks, the RS 1 transitions to the mark specimen mode 616. If the user enters the finish command and there are no electronic marks, the RS 1 re-enters the manual review mode 636.

A system diagnostics mode 628, 638 is entered when the RS 1 is in the user login mode 604 and the server attempts to query the RS 1 for information. The RS 1 sends the requested information to the server and transitions to the user login mode 604. The diagnostics mode does not allow for specimen review, but is used to test subsystem components and view the status of internal variables.

Some of the functions referenced hereinabove are now described in greater detail. One such function is electronic marking and unmarking. When electronic marking is enabled, if the user enters a mark command, the RS 1 determines if the current location is electronically marked. If not, the current X, Y coordinates are added to the list of marked target zones. If the current location is already within a marked target zone made during the current specimen review, the center coordinates of the target zone are removed from the list of marked target zones. Mark indication is another function. When mark indication is enabled, the RS 1 continuously checks stage position and determines if the current location is within a marked target zone. If it is, the RS 1 illuminates the mark indicator to be green in color. Otherwise, the RS 1 illuminates the mark indicator to be white in color. The RS 1 performs this checking during user-directed positioning, while the stage is moving or when motion ceases. During change of magnification, one of the inputs on the user interface is used to change objective lenses, for example, from 10× to 40× or from 40× to 10×. During cancel specimen review, if the cancel command is entered, the RS 1 stops all motion, stage and/or marker, emits an audible tone, and prompts the user for confirmation that specimen review is to be cancelled. If a yes command is entered, the RS 1 transitions to the load specimen mode 606. The display may issue a warning (e.g., "erase all physical marks"). If a no command is entered, the RS 1 returns to its previous operational state. In addition, the RS 1 may include a specimen presence sensor and associated functions. If the specimen holder is opened at any time during an operational mode in which it is enabled, the RS 1 stops all motion, stage and/or marker, displays a warning (e.g., "specimen removed-review cancelled"), emits an audible tone, and prompts the user to enter the continue command. If the specimen holder is opened after the specimen has been physically marked, the display should additionally warn the user to erase all physical marks. Upon entering a continue command, the RS 1 restores the object marker to its resting state, if necessary, and transitions to the load specimen mode 606.

Figure 4:
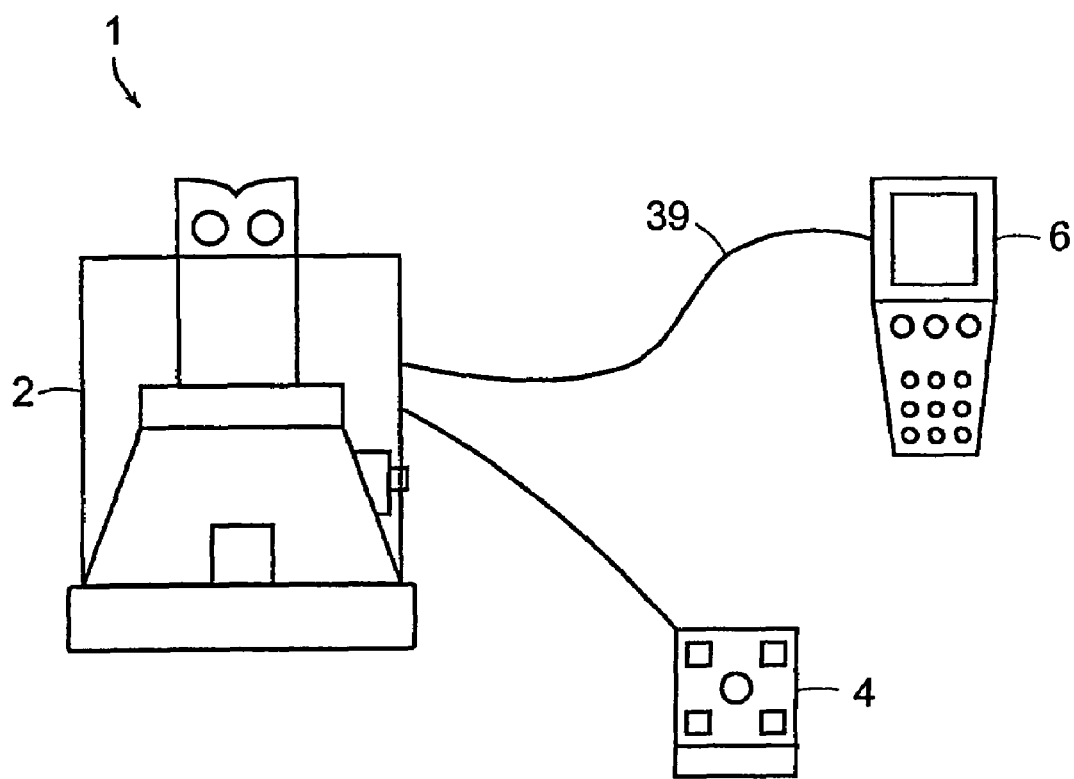
FIG. 4 is a perspective view of a review system including a review station, user interface, and a console.
Figure 5A:
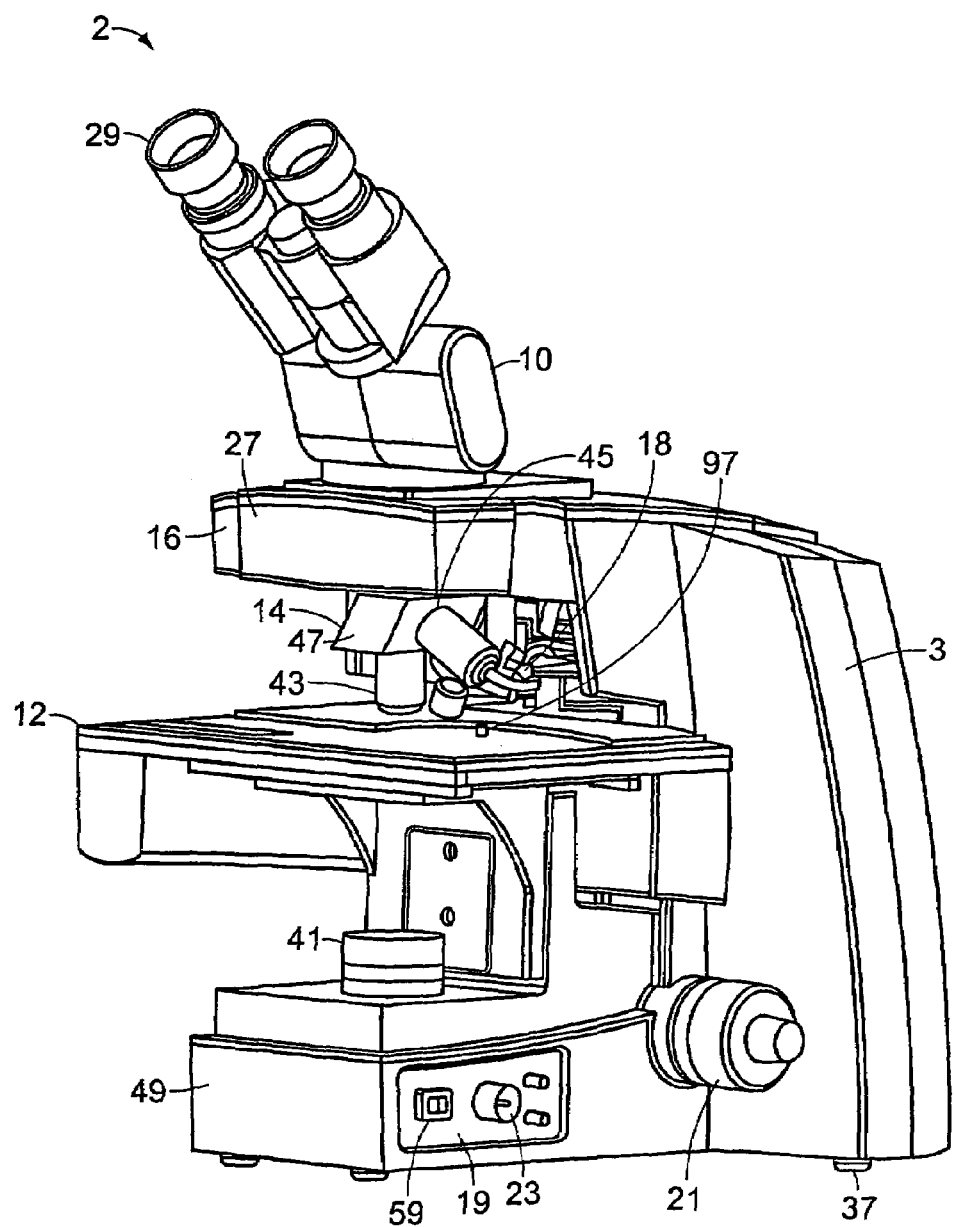
FIG. 5A is a perspective front view of the review station of FIG. 4.
Figure 5B:
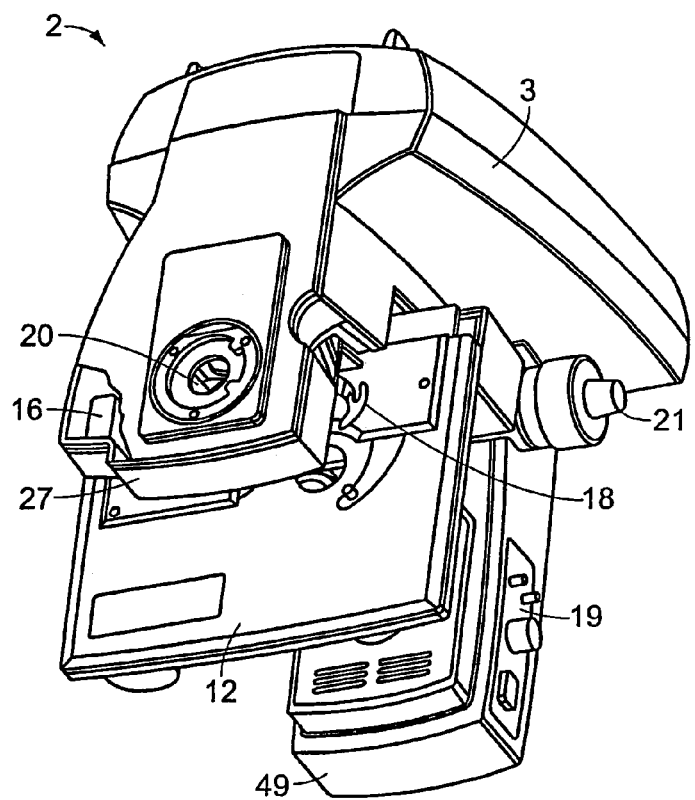
FIG. 5B is a perspective top view of the review station of FIG. 4.
Figure 5C:
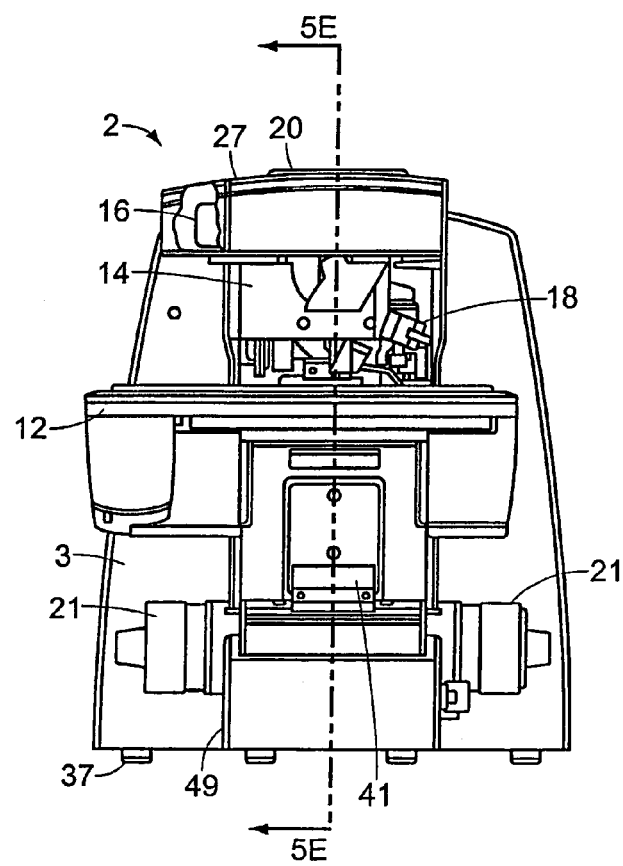
FIG. 5C is a schematic front view of the review station of FIG. 4.
Figure 5D:
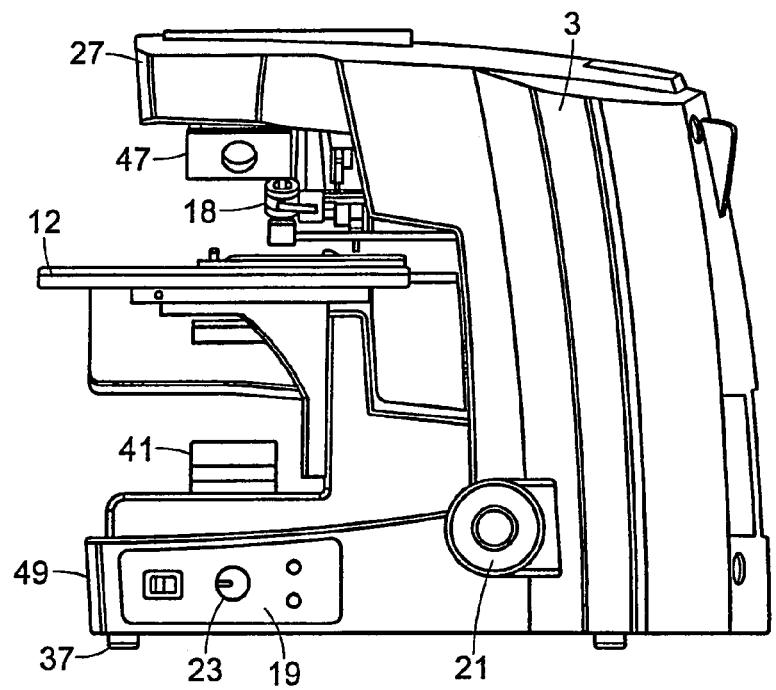
FIG. 5D is a schematic side view of the review station of FIG. 4.

FIG. 4 depicts the RS 1 including peripherals. See also FIG. 1. The RS 1 includes a review station 2, a user interface 4, and a console 6. The RS 1 also includes a processor 8, which in FIG. 4 is located within the review station 2. The review station 2, user interface 4, console 6, and processor 8 are in electrical, mechanical, and/or data communication with one another.

FIGS. 5A-5E are illustrations of the review station 2. In some of the figures, components have been removed for clarity. The review station 2 includes a frame 3, an optical instrument 10, an illuminator subsystem 11, an illumination control panel 19, and focus controls 21. The review station 2 also provides the structural and optical framework for additional custom subsystems, which can be integrated into the review station 2 for the purpose of providing the specific functionality. More specifically, the review station 2 includes a motorized stage 12, an OCR reader 16 (ID reader), a motorized two-position nosepiece 14, a mark indicator 20 (visual indication of mark location in the FOV), an object marker 18 (physical marking of an object of interest in a specimen), a processor 8, a Koehler illuminator, an illuminator controller 23, an upper arm 27 (including the mark indicator module 20 and the object marker subsystem 18), and an eyepiece 29.

The frame 3 is similar in size and form as compared to microscopes currently used in a clinical setting. The frame 3 has a low center-of-gravity, resists damage due to shock or vibration, and minimizes potential pinch points, for example, from stage, nosepiece, or object marker motion. In one embodiment, the frame 3 has a high degree of stiffness to minimize movement in the eyepiece 29 during quick stage moves. The frame 3 includes a upper arm 27 that has minimal deflection. In some embodiments, a support leg may be used to minimize further the deflection of the upper arm 27. The FOV may become blurred during 40× viewing if the upper arm 27 deflects too much. The frame 3 can incorporate four rubber non-skid feet 37 fastened to its base. These rubber feet 37 can minimize shock to the review station 2, dampen impulses and environment oscillations, and prevent sliding on the bench top surface. The frame 3 can be made from cast aluminum; however, other materials, as known to one of ordinary skill in the art, are contemplated.

The review station 2 shown in FIGS. 5A-5E utilizes Koehler type illumination for lighting the specimen. The illumination system provides the user with easy access to the bulb chamber to replace the bulb and for adequate thermal cooling in the illumination area. Proper cooling extends the bulb life and reduces user hazards related to the elevated external surface temperatures. Adjustment of the illumination aperture 41 (view diameter of the illumination source) has easy access, smooth motion, and an adequate gripping surface. The illumination system 11 includes an illumination control panel 19. The illumination controls (power, light intensity, green mark indicator intensity, and white mark indicator intensity) are grouped within easy access of a focus knob 21.

The motorized nosepiece subsystem 14 is located on the bottom side of the upper arm 27 of the frame 3. The nosepiece 14 provides automated selection and positioning of the objective lenses 43, 45 as commanded. In the embodiment shown in FIG. 5A, the objective lenses 43, 45 are 10× and 40×; however, other magnifications could be selected to suit a particular application. The nosepiece 14 rotates from side-to-side approximately 60° to switch between the two objective positions. The necessary motor 13, sensors 17, and drive system are mounted behind the objective holder 47. The right objective mount provides two set screws to translate the objective in a plane perpendicular to the optical path. This allows for parcentricity adjustments. To provide parfocality, adjustment shims can be added between either of the two objectives 43, 45 and the nosepiece 14 to decrease the distance to the common focal plane. The objective lenses 43, 45 can be standard Olympus UIS series infinitely corrected optics. The nosepiece subsystem 14 operates using a DC permanent magnet brushed servomotor 13 with an integral gear head. The motor 13 operates at about 5 volts (V) and has about 22 ohms of resistance. The gear head drives a cam follower that pushes the objective holder 47 from side to side. Another cam and spring arrangement causes the nosepiece 14 to toggle and hold over at correct objective locations.

Electrically, there are three components, a motor 13 and two sensors 17, one for each end of travel, to indicate the objective is in place. The two optical interrupt sensors 17 take +5V and ground inputs and produce an output that is low when a flag is blocking the sensor. The motorized nosepiece 14 interfaces to the review station 2 via the processor 8. The review station processor 8 monitors the rotary position of the nosepiece 14 via position sensors 17 connected to digital input ports. The user can toggle the nosepiece position via a user interface input, such as an objective selection button 15.

The specimen ID reader subsystem 16 is located within the upper arm 27 of the frame 3. The slide ID reader 16 is used in the RS 1 to acquire an image of a specimen label and uses OCR to determine the specimen ID and CRC. In one embodiment, the specimen ID reader 16 is a custom Welch Allyn camera and processor that includes a camera, a lens, a CCD sensor, a light source, a processor, and a frame grabber. The specimen ID reader 16 has a working distance (i.e., the distance from the camera lens surface to the specimen label surface) of about 3.7 inches; however, the working distance can vary to suit a particular application. The specimen ID reader 16 has a viewing angle (i.e., the angle deviation from parallel between the camera lens surface and the specimen surface) of about 13°+/−2°; however, the viewing angle can be chosen to suit a particular application. The specimen ID reader 16 operates accurately in an external light environment such as normal office lighting (e.g., 100 foot-candles).

The specimen ID reader 16 captures an image of the specimen ID and CRC on the specimen label. The specimen label may have at least one line of characters with up to 7 characters on a line. The label may include characters representing a patient ID. In one embodiment, the last three characters are the CRC. All characters are OCR-A and are limited to the digits 0 through 9 and the symbol "−". The electrical interface to the specimen ID reader 16 consists of two cable assemblies, which can be combined into one for routing from the review station processor 8. Communication over the interface is bi-directional and allows the review station processor 8 to control the specimen ID reader 16 and receive the specimen ID data or any error messages.

Figure 13:
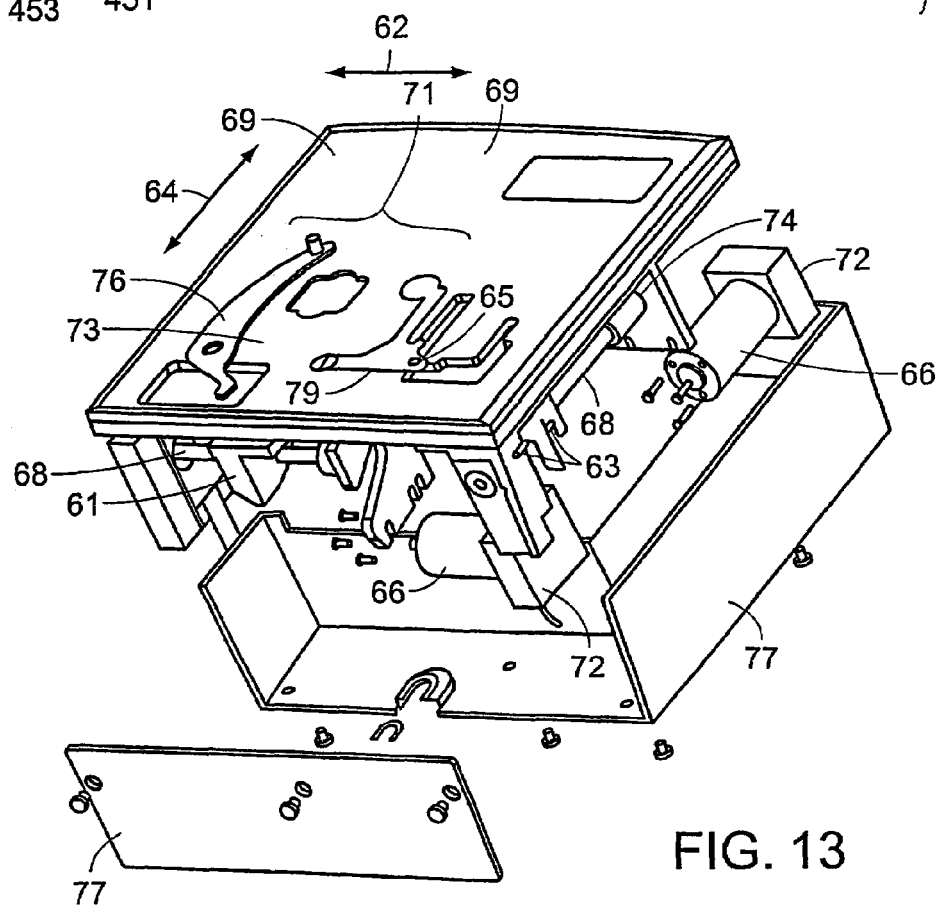
FIG. 13 is an exploded perspective view of a motorized slide stage.

The motorized stage subsystem 12, which is located on the frame 3, can be seen in FIG. 13. The motorized stage 12 moves the specimen in the horizontal plane with respect to the motorized nosepiece 14 to facilitate specimen loading, specimen ID reading, specimen review, viewing of the fiducial marks, and object marking. In addition, the motorized stage 12 is used to position the slide specimen area in the FOV to facilitate the location of FOIs, marked target zones, and destinations arrived at manually. The stage 12 can move at a constant velocity in a single direction within the cell spot boundary during an autoscan mode 614, 622. Further, the stage 12 moves the specimen to create physical marks, for example, the specimen reviewed mark. See FIGS. 15A and 15B. The stage 12 includes hard stops 61 to limit travel on the X and Y-axes 62, 64 and sensors 63 to indicate home positions, and a sensor 65 to sense the presence of a specimen on the stage 12. The sensors 63, 65 are hall-effect switches, but could also be limit switches, proximity switches, or optical or magnetic sensors. In one embodiment, the stage size is about 255 mm wide, 280 mm deep, and 90 mm high.

The stage 12 provides travel along two orthogonal axes, where the X-axis 62 is left/right and the Y-axis 64 is front/back. Each axis 62, 64 includes a platform 69 guided on a linear bearing system. A DC servomotor 66 drives each axis 62, 64 through lead screws 68 with the drive system using plastic anti-backlash nuts 70 to minimize backlash. In order to minimize loads on the motor shaft and maintain axial alignment of the encoder 72, the lead screws 68 are mounted with a centering coupling system 74 on the servomotor end and thrust bearings on the other end. Both axes 62, 64 are controlled using encoder feedback and home sensors 63. The stage 12 includes a specimen holder 71 mounted on the Y-axis platform 69 to maintain alignment of the specimen with the stage 12. A spring-loaded arm 76 allows the user to load and unload the specimen, and a sensor 65 is included to verify the presence of a specimen in the specimen holder.

The stage 12 is attached to the frame 3 by a Z-axis horizontal mount. The stage 12 is fastened to the horizontal mount using screws; however, other commonly known fastening methods could be utilized, such as welding, rivets, chemical bonding, and the like. The stage 12 includes locating features, such as pins, in order to establish the stage position relative to the frame 3. In one embodiment, the X-axis motion is about 60 mm and the Y-axis motion is about 56 mm. A double shaft, DC brushed servomotor is used for the X and Y axis drive. The lead screw pitch is about 2 mm, and a self-centering coupling is used to connect the lead screw to the motor to maintain axial alignment. A thrust bearing can be used to support the lead screw free end to minimize velocity ripple. In one embodiment, the stage 12 has a maximum speed of 32 mm/sec and a minimum speed of 0.02 m/sec; however, the stage speed can be selected to suit a particular application. The drive connection may use an anti-backlash nut to minimize backlash, for example, a drive screw/nut that is self-lubricating to eliminate servicing requirements and minimize noise and stiction. The stage 12 incorporates motor covers 77 to cover and protect the motors, sensors, and wire harnesses. The motor covers 77 also protects the user from any possible pinch points.

The stage home position is determined using one sensor 63, for example a hall-effect switch, per axis. A hard stop 61 is used to prevent damage in the event of loss of motor control. The specimen holder 71 incorporates a sensor 65, for example a hall-effect switch, to detect specimen presence. In order for the specimen to be loaded properly and the correct position maintained through a full sequence of operations, it is desired that the specimen sensor arm 79 actuation force be significantly lower than the specimen retaining arm 76 actuation force. For example, the actuation force of the specimen sensor arm force can be about 5 g to about 20 g and the specimen retaining arm force can be about 100 g to about 140 g. This arrangement helps to prevent the sensor arm 79 from moving the specimen away from a datum position. The slide retaining arm 76 should apply sufficient force on the specimen to prevent any movement of the specimen away from the datum position during object marking. The specimen resting surface 73 is preferably stiff, flat, resistant to scratching, and has a low friction coefficient with little noticeable stiction. In one embodiment, the specimen resting surface has a flatness of ±4 µm over 0.22 mm.

Each axis has a brushed DC servomotor 66 for motion. Each motor 66 can be controlled via a separate servomotor interface module in data communication with the review station processor 8. Feedback is provided by an optical encoder 72 mounted on the motor shaft; however, other feedback devices can be used. The interface module supplies power to the motors 66 and monitors encoder feedback. Each axis has at least one sensor 63 that determines the home position of the stage 12 and interfaces with the review station processor 8. The home sensors 63 are used to establish the stage home position. The specimen presence sensor 65 also interfaces with the review station processor 8.

Figure 5E:
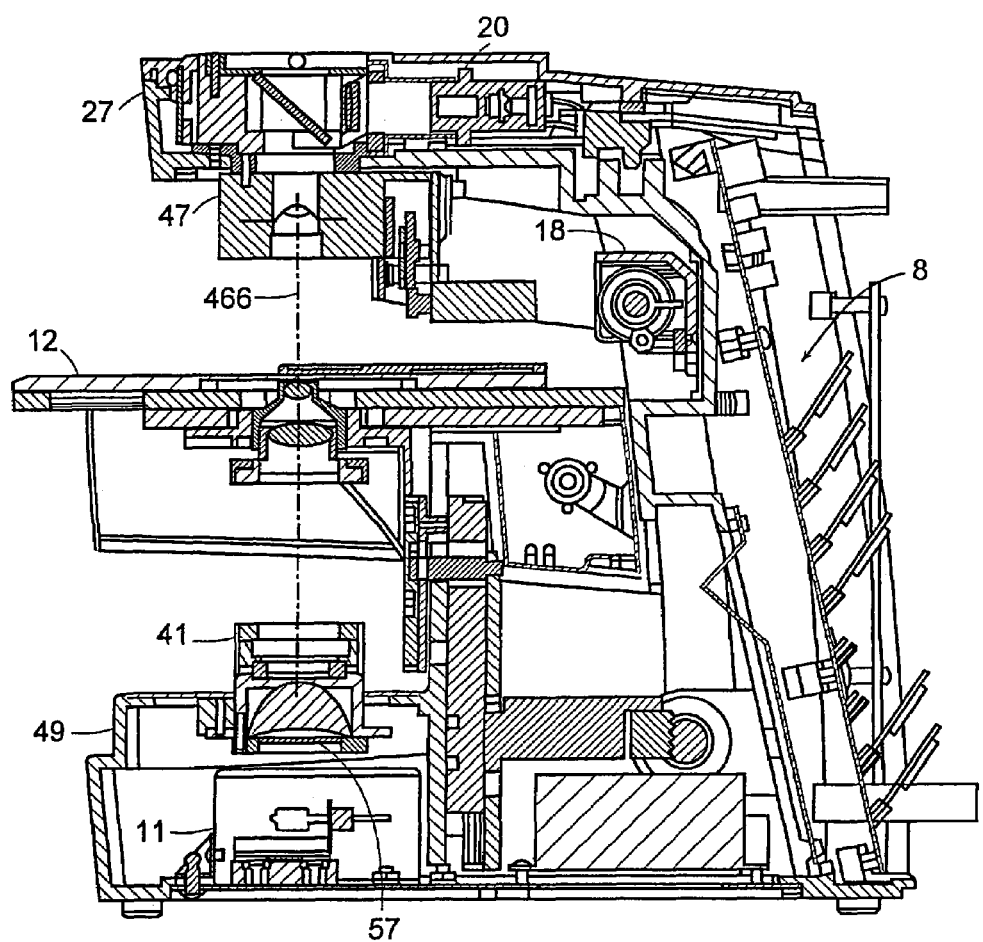
FIG. 5E is a schematic cross-sectional view of the review station of FIG. 4 taken at line 5E-5E in FIG. 5C.

One embodiment of an illuminator subsystem in accordance with the invention is shown in FIG. 5E. The illuminator subsystem 11 is located in the lower arm 49 of the frame 3 and provides for the illumination of the specimens being viewed on the review station 2. The frame 3 supports and aligns the illuminator 11 with respect to the condenser assembly 57 and optics. Alignment and calibration of the condenser assembly 57 facilitates proper specimen illumination. The illuminator 11 includes a base plate with access door, a power supply, an illumination controller 23, and a halogen lamp. The power supply and illumination controller converts AC voltage into the user-adjustable DC voltage supplied to the halogen lamp. The lamp is located in a lamp holder that is attached to the access door on the base plate. This positions the lamp for illumination of the specimen through the condenser assembly 57 and allows the lamp to be accessed for replacement. Heat from the lamp is transmitted through a heat shield and base plate and is dissipated to the frame 3. The base plate provides structure for the illuminator 11 and attaches to the bottom of the frame 3. In one embodiment, the illuminator operates at 90-264 VAC, single phase, 47-63 Hz, and has a power output of 35 W.

The illumination control panel 19 is located on the side of the lower arm 47 of the frame 3 and provides an on/off switch 59 and control 23 for adjusting illumination. The control panel 19 also holds the potentiometers for adjusting the intensity of the white and green mark indicator images.

Figure 8:
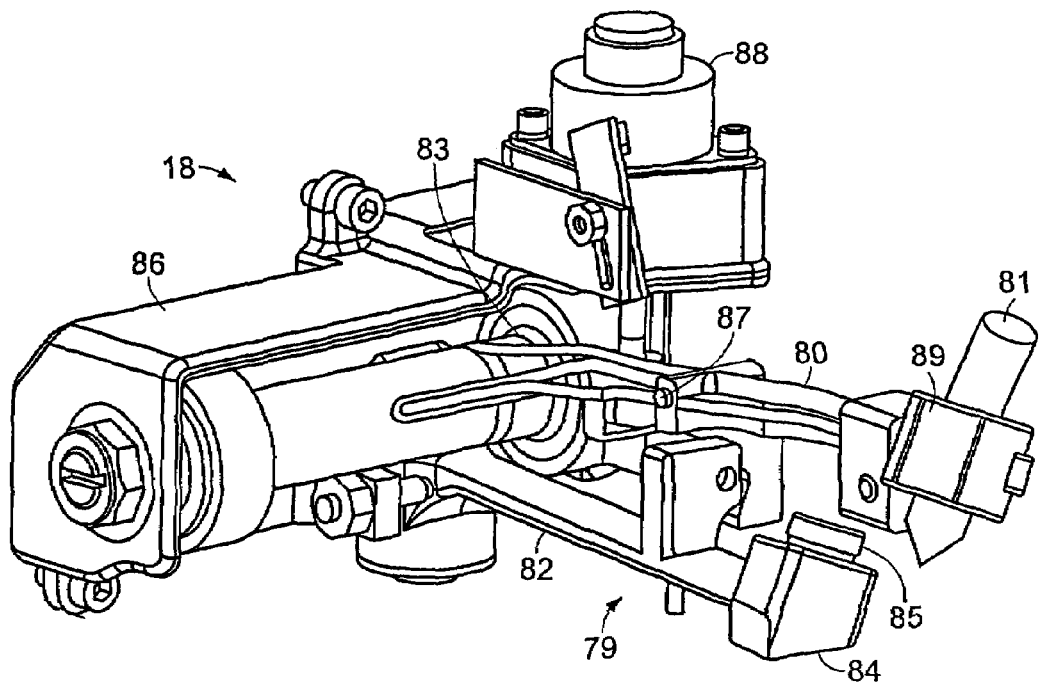
FIG. 8 is a perspective view of one embodiment of a marker module for use with a review system in accordance with the invention.
Figure 9:
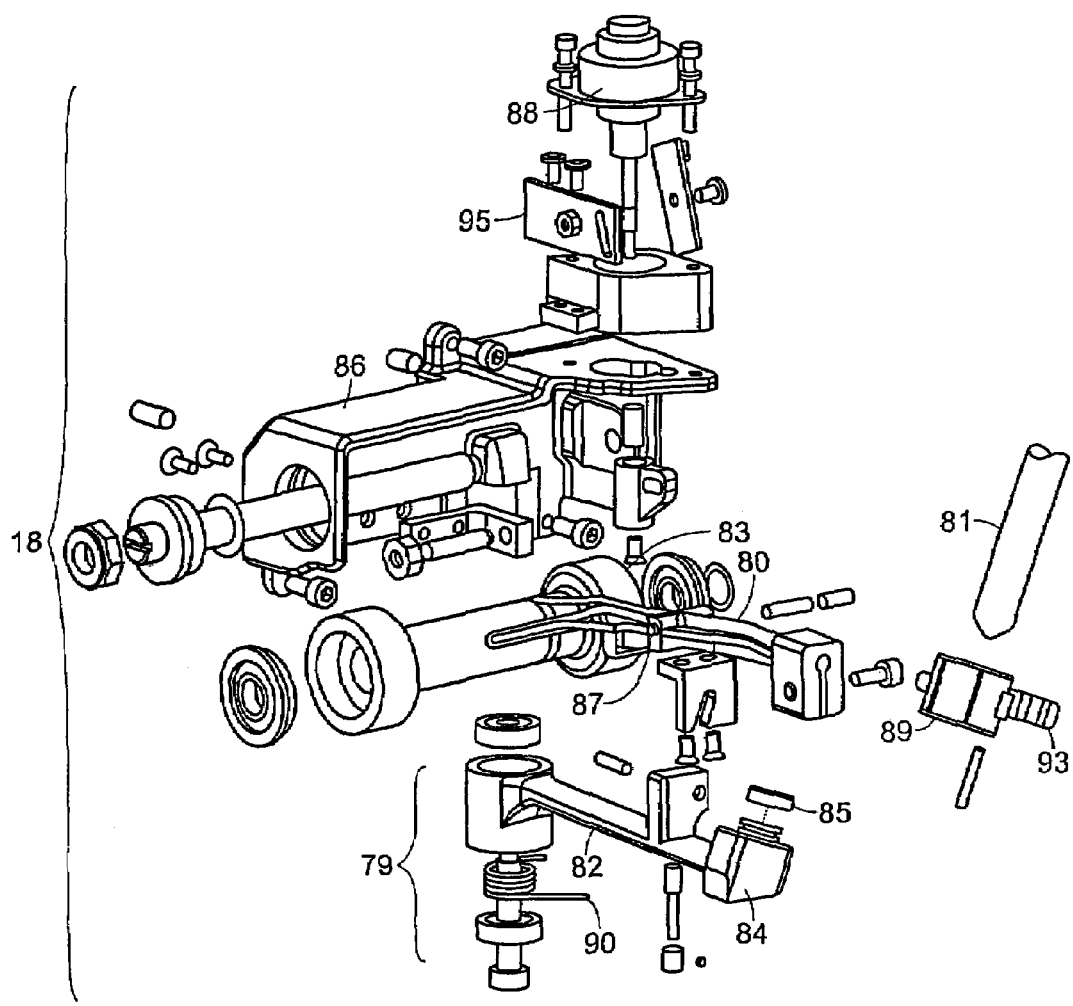
FIG. 9 is an exploded perspective view of the marker module of FIG. 8.

FIGS. 8 and 9 illustrate one embodiment of the object marker subsystem 18. Specifically, FIG. 8 is the assembled object marker subsystem 18, as it resides on the review station 2, and FIG. 9 is an exploded view of the object marker subsystem 18. The object marker subsystem 18 is located on the review station 2 under the upper arm 27 and behind the stage 12. The marker 81 places physical marks at the locations of electronically marked target zones on a specimen mounted on the stage 12. The marker's functions include, but are not limited to, physically placing marks on the specimen to indicate sites where further investigation is suggested, physically marking the specimen to indicate that the specimen has been reviewed, and providing for capping and sealing the marker 81 when not in use. The marker 81 is capable of marking on conventional glass slides, float glass slides, coatings on the glass slide, glass coverslips, and plastic coverslips.

In one embodiment, the marker utilizes a Sharpie® pen, which can be obtained from the Sanford Corporation in Bellwood, IL, to generate the mark on the specimen. This pen is widely used and accepted for manually marking cover slips and slides. The solvent based ink marks reliably and quickly on glass or plastic cover slips, dries quickly so it does not smudge easily, is fairly translucent, and is non-toxic. The marker motion is provided by a cantilevered arm 80 rotating about a fixed pivot point 83. This arrangement provides highly repeatable, reliable motion with minimal frictional effects. One linear stepper motor 88 is used to drive the marker 81; however, other numbers and types of actuators are contemplated. A sensor 87 is used to establish the home position of the marker 81.

The object marker subsystem 18 includes a capping/uncapping mechanism 79. The uncapping motion is spring actuated; however, other types of biasing apparatus 90 are contemplated. The capping motion is actuated by the stage 12. The stage 12 moves to a specific position to push the marker cap 84 into an engagement position with the marker 81. The stage 12 includes a pin 97 or other type of protuberance to contact the cap arm 82 and drive the cap arm 82 into the engagement position.

The marker 81 is positioned at a tilt angle of approximately 24°; however, other angles are contemplated. Orienting the marker 81 at an angle positions the marker 81 closer to the optical axis, which minimizes the required stage travel and size. The marker 81 is held firmly during operation, without slippage or backlash due to variation in marker manufacturing. The marker holder 89 is located on the right side of the frame upper arm 27. The marker 81 is easy to load and unload. The marker holder 89 weight is minimized to prevent any incremental weight from contributing to potential marker impact issues on the specimen. In addition, the marker holder 89 can include a clamping mechanism to securely hold the marker 81 and is structurally robust enough to prevent damage due to accidental bumps.

The marker cap 84 provides a repeatable and reliable airtight seal compliant with the manufacturing variation of the marker 81. The cap 84 includes a replaceable diaphragm 85 to allow for replacement due to wear and damage. This diaphragm 85 is easily replaced by the user. The diaphragm 85 has a combination of a low insertion/extraction force and a high seal compliance to assure reliability.

Figure 16:
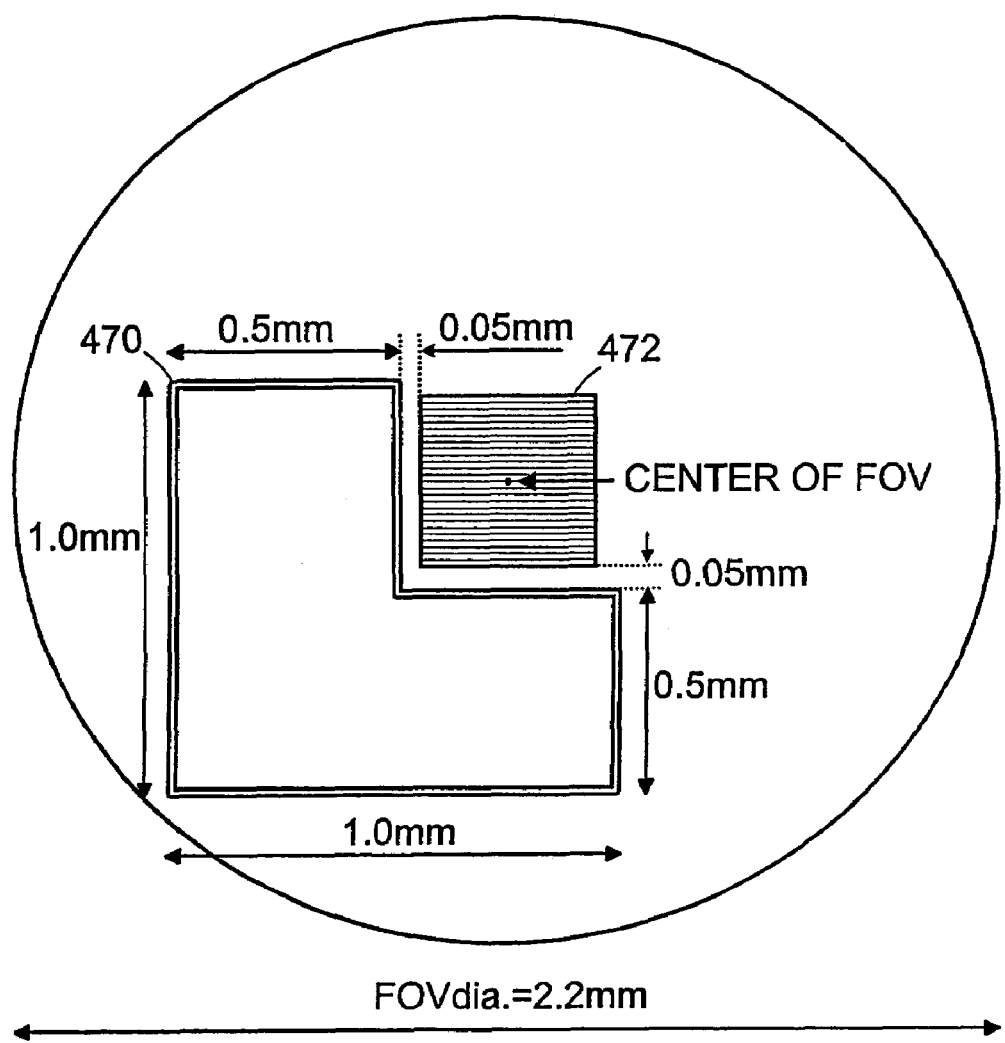
FIG. 16 is a schematic view of one embodiment of a mark indicator.

During marker 81 loading, the marker arm 80 moves to a home position (up in the current embodiment) and the marker cap 84 moves to an disengaged position. The marker 81 is manually loaded and clamped in the holder 89. The RS 1 then proceeds to make a sequence of marks to calibrate the marker's vertical position relative to a focal position of the specimen. During marking, the marker arm 80 raises the marker 81 to the home position. As the marker arm 80 is raised, the spring loaded cap arm 82 releases from the marker 81 and the cap 84 is biased away from the marker 81. In some embodiments, the stage 12 will position the specimen into a marking position relative to the marker 81. Next, the marker arm 80 lowers the marker onto the specimen with a controlled velocity, and the stage 12 moves the specimen relative to the marker 81 to create the mark. In some embodiments, the stage 12 makes multiple corresponding moves to repeatedly mark the specimen in an over-writing fashion. The mark is a combination of line segments and/or arcs that at least partially bound the object of interest, an example of which is shown in FIG. 16. The marker arm 80 raises and maintains this marker position if further marks are required. If there are no more marks to be made, the marker arm 80 returns the marker 81 to the home position. The stage 12 then moves the cap arm 82 and cap 84 into the engagement position. The marker arm 80 lowers the marker 81 into the marker cap 84.

In one embodiment, the maximum allowable normal force (Z-direction) the marker 81 may transmit to the specimen is 30 g. This is intended to minimize the marker impact on the specimen. To prevent cell migration due to marker loading on the specimen, in particular, a coverslip may be located over the specimen. A high impact may cause cell migration and/or marker 81 bounce.

To ensure accuracy, the marker 81 should be calibrated each time it is replaced. Calibration is recommended due to the relatively high accuracy needed for the maker location and the corresponding large variation in the manufacturing tolerances of the marker 81. A calibration procedure is used to establish the position of each new marker 81 to ensure that a mark is placed accurately with respect to a marked target zone. Once calibrated, the dimensional variation between the mark indicator center and the physical mark center during repeated cycles is preferably about ±0.1 mm or less.

Figure 10:
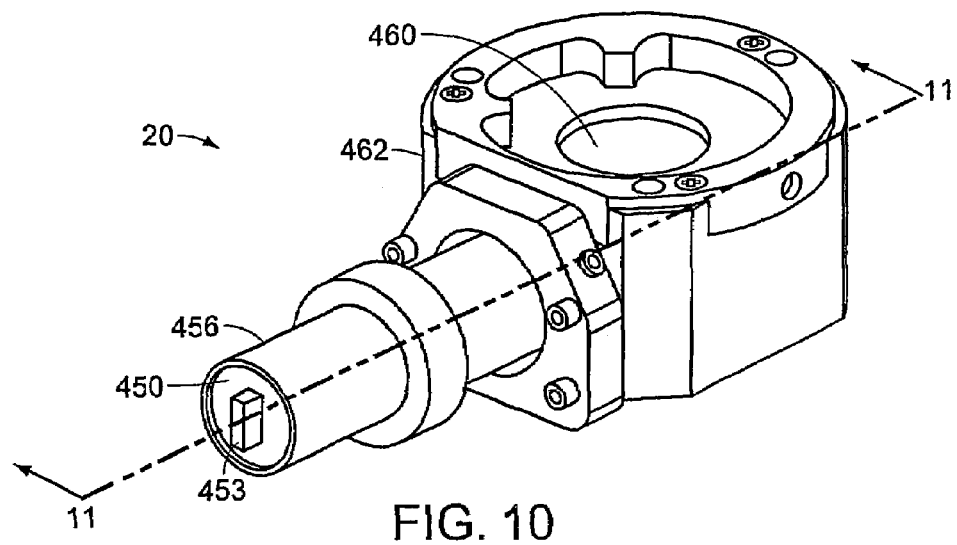
FIG. 10 is a perspective view of a mark indicator module for use with a review station in accordance with the invention.
Figure 11:
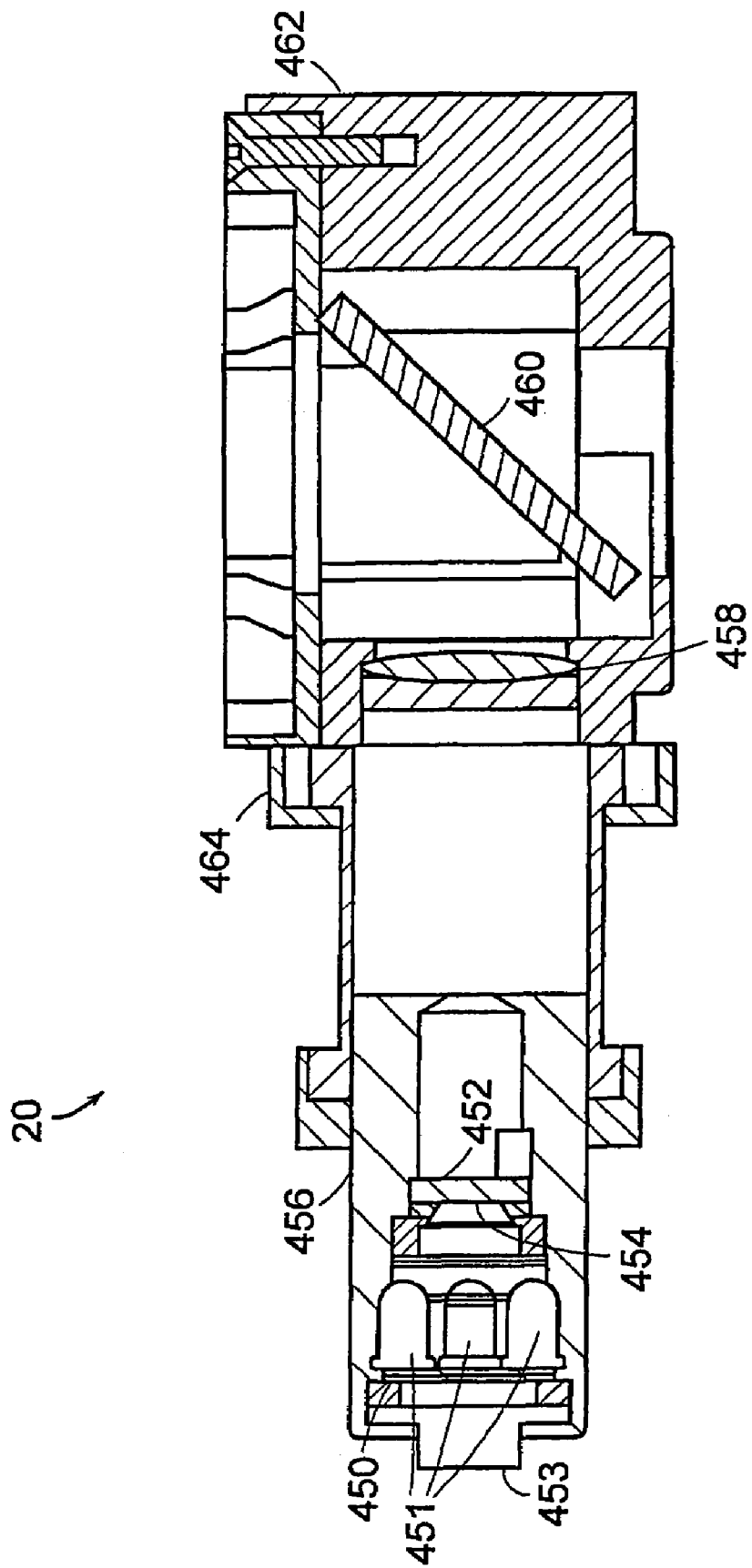
FIG. 11 is a schematic cross-sectional view of the mark indicator module of FIG. 10 taken at line 11-11.
Figure 12:
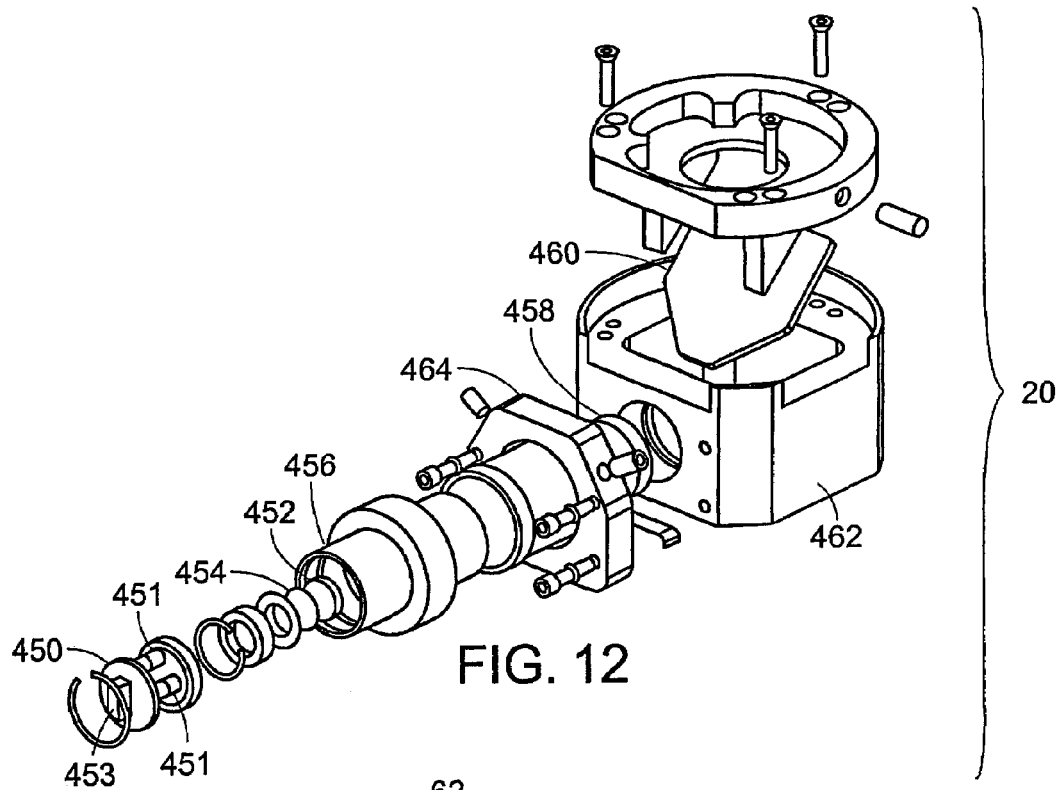
FIG. 12 is an exploded perspective view of the mark indicator module of FIG. 10.

FIGS. 10-12 depict the mark indicator module 20. The module 20 is located in the upper arm 27 of the review station frame 3, directly above the motorized nosepiece 14. The bottom of the mark indicator module 20 interfaces to the review station 2 via an optical mount ring. The mark indicator module 20 produces a shaped pattern 470 in the FOV that indicates to the user whether a target zone is marked or not. The shaped pattern 470 can be a line segment, an arc, or combinations thereof, for example, an "L" or "V" shape. The mark indicator 20 is also a means for the user to locate material in the FOV prior to electronic marking or a feature present in the optical path utilized in establishing or verifying registration, i.e. a fixed reference within the FOV to which fiducial marks on the slide may be aligned by the user. In one embodiment, the mark indicator 20 is a device that produces an LED-illuminated pattern 470 that overlays the view of the specimen seen by the user. The pattern 470 is produced by directing light from an LED 450 through a mask 452, focusing and combining the resulting pattern 470 in the optical path 466 between the objective 43, 45 and the optical instrument 10. The mark indicator 20 includes an illumination light source 450 (white and green LEDs), a diffuser 454, a mask 452 with an opening the shape of the indicator pattern 470, an aperture 456, a lens 458, a beam splitter 460, a housing 462, and pattern alignment and focusing features. In one embodiment, the illumination light source 450, the diffuser 454, the mask 452, the aperture 456, the lens 458, focusing optics 464, and the beam splitter 460 are in serial relationship beginning with the light source 450.

The illumination source 450 includes two green LEDs 451 and two white LEDs 451; however, any number and/or color of LEDs may be used and, depending on the particular application, illumination sources other than LEDs may be used, such as a halogen bulb. When the green LEDs 451 are on, a green shaped pattern 470 is visible to the user looking into the eyepieces 29 of the review station 2. Similarly, when the white LEDs 451 are on, a white shaped pattern 470 is visible to the user. The operation of the LEDs 451 is mutually exclusive, such that either of the sources of illumination (green or white) can be on, but not both. The LEDs 451 are directed at the diffuser 454, which ensures that the pattern 470 is uniformly illuminated by the LEDs 451.

In the illustrated embodiment, the mask 452 is a chrome deposit on a glass substrate in the shape of the indicator 470, where the shape is clear and the background is opaque (chrome). This allows the light generated by the LEDs 451 to pass through the mask 452, thereby generating the shape 470 seen by the user. The aperture 456 reduces stray light and limits the numerical aperture of the system. The lens 458 allows the pattern 470 to be properly focused in the optical path 502. The beam splitter 460 combines the pattern image into the review station optical path 466. The housing 462 offers mechanical support for the optical and electrical elements of the mark indicator 20. The pattern alignment and focusing features allow the pattern 470 to be properly centered (translated), rotated, and focused so that the pattern 470 appears at the correct orientation, position, and in focus in the review station FOV. Electrically, the mark indicator LEDs 451 connect to digital output lines from a digital output port 453 to the processor 8. The brightness of the illumination source 450 can be adjusted by varying series resistance in the output lines.

Referring now to FIG. 16, an "L" shaped mark indicator pattern 470 is shown. The dimensions shown are approximate and for illustrative purposes only. In the embodiment shown, the pattern 470 is about 1 mm by about 1 mm and about 0.5 mm wide; however, the size and shape of the pattern 470 can be chosen to suit a particular application. As can be seen, the pattern 470 at least partially bounds the marked target zone 472 on two sides.

Figure 6:
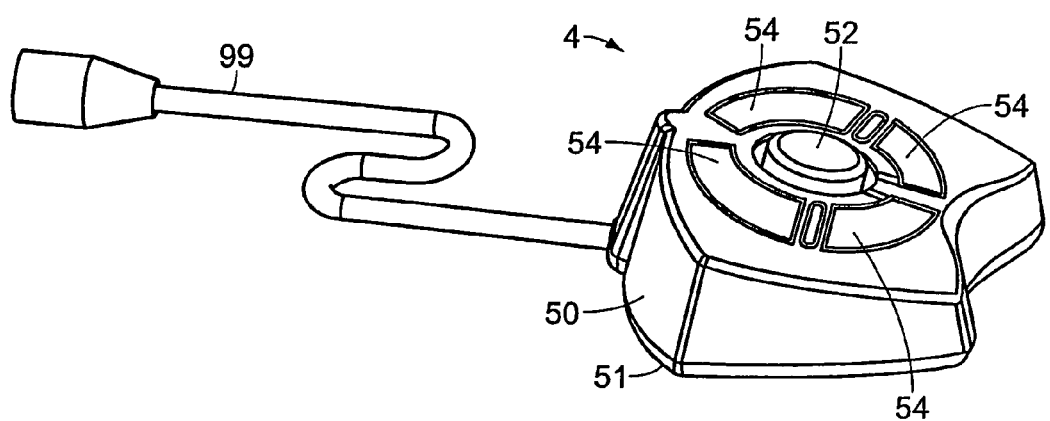
FIG. 6 is a perspective view of the user interface shown in FIG. 4.

The user interface 4 is illustrated in FIG. 6. The user interface 4 is typically located on a work surface adjacent to the review station 2. The user interface 4 is an input device intended for use when the user's visual attention is required for viewing in the review station 2. The user interface is a two-piece plastic housing 50 with five input/output devices. The user interface 4, however, may include any number and/or combination of input/output devices to suit a particular application. In one embodiment, the input/output devices include a specimen position input device ("SPID") 52 and four independent buttons 54 facilitating the following commands: next, previous, objective, and mark. The user interface 4 allows the user to manually position the stage 12 via the SPID 52. The SPID 52 is used for centering FOIs within a target zone for subsequent review and marking by a user.

The housing size and shape is intended to provide ergonomic benefit to the user as well as the physical space required for the electronic components. The size is preferably small to minimize the space required for the user interface 4. The housing 50 may be fabricated from sheet metal, plastic, machined components, or combinations thereof. The housing base 51 may include non-skid rubber feet attached to the bottom to prevent slipping during use. The rubber feet are adequately spaced to prevent tipping during button actuation. In one embodiment, the housing 50 is shaped to orient the input/output devices at about 15° relative to the work surface to provide for ease of use.

In one embodiment, the SPID 52 is a button joystick that utilizes hall-effect sensor technology to sense displacement along two orthogonal axes. The SPID 52 utilizes the magnitude of the displacement along the two axes to control the speed and direction of the stage 12. The SPID 52 outputs are two analog signals ranging from 0 to 5 volts. The other input devices are push-buttons 54, but could be any similar device, such as a toggle switch. The buttons are positioned relatively close to the SPID 52 for ease of use. The button force and travel characteristics are similar to a computer "mouse" feel with relatively low actuation force (e.g., <200 g), and high tactile response for user feedback. The user interface 4 houses an electrical interface 53 that is in data communication with the RS processor 8 via a cable 99.

The following is one example of an application of the user interface. The SPID 52 can be used to align fiducial marks with a mark indicator 470 to establish registration. Two of the buttons 54 function as next and previous commands for sequencing through a predetermined number of FOIs during an autolocate mode 610 and through a series of electronically marked target zones (if any) during a review mode 612. The buttons 54 trigger the transition to the next or previous FOIs in a user-triggered autoscan. A third button 54 can be used to electronically mark or unmark a target zone. A fourth button 54 can be used to toggle between multiple objective lenses, for example 10× and 40×.

Figure 7:
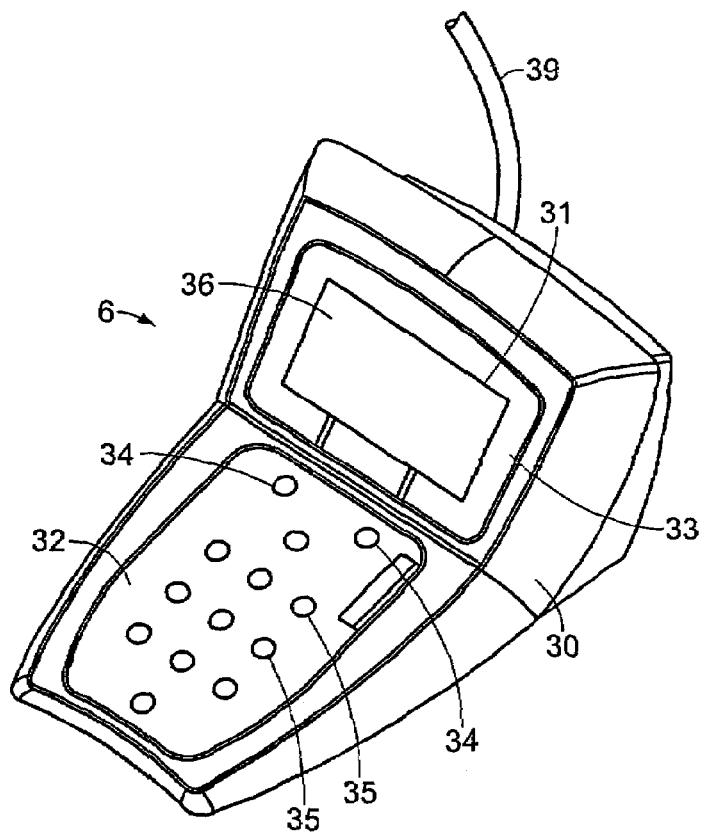
FIG. 7 is a perspective view of the console shown in FIG. 4.

The console 6 is illustrated in FIG. 7. The console 6 is also typically located on the work surface adjacent to the review station 2. The console 6 is an input/output interface for the review station 2 intended for use when the user's visual attention is not required for viewing in the review station 2. The console 6 includes a housing 30, a keypad 32, a display 36, a serial interface/controller, and a cord 39. The housing 30 protects and supports the electronic components contained within and may be fabricated from sheet metal, plastic, machined components, or combinations thereof. The housing 30 size and shape is intended to provide ergonomic benefit to the user as well as the physical space required for the electronic components. The width of the housing base should be optimized to provide adequate button spacing and to minimize tipping during keypad entry and to minimize overall console profile. The housing base may include non-skid rubber feet attached to the bottom to prevent slipping during use. The rubber feet are adequately spaced to prevent tipping during button actuation. In one embodiment, the console is about 3.6" high, about 6.3" deep, and about 4.6" wide.

In one embodiment, the display 36 is a 128×64 backlit, dot-matrix graphics LCD. The character height is about 6 mm. The character height should be optimized to provide adequate viewing from a nominal distance of about 3 feet; however, the text height could be varied for any particular application. The display 36 has a viewing angle of about 35° to provide for optimal viewing. The display 36 is viewed through a protective window 31 on the console bezel 33. The display 36 presents the user with the following information: system status including progress updates, display error log, maintenance record, usage history entries, prompts and error messages, user preference menus, diagnostic information, and the current operational mode of the device; however, this list is not exhaustive.

The keypad 32 may be a membrane switch with a graphic overlay. The membrane switch utilizes a metal dome (in a specific "dummy dome" construction method) to enhance switch tactile feedback. In one example, the keypad actuation force is less than 250 g. The keypad 32 has the following keys: 0-9 (numeric), soft (software definable) keys, and cancel. The soft keys 34 are buttons in the vicinity of the display 36. The labels associated with these keys 34 appear on the display 36. The labels and the actions associated with pressing the soft keys 34 may change depending upon the current operational mode. Keypad 32 orientation is preferably 15° to provide for ease of keypad entry. Examples of console functions performed via the keypad 32 include accepting inputs from the user, inputting user identification during login, manual slide ID input, changing the operational mode (autolocate 610, review 612, autoscan 614, 622, and manual review 636) of the RS 1, accept user input to complete specimen review, accept user input to logout, accept input of user preferences, and accept user input to cancel a slide review, among others. The serial interface/controller is a PCA that has an RS-232 interface to a Parallel-Serial Interface Module (PASEIM) on the processor 8. The serial interface/controller controls the LCD, stores fonts, graphics, and macros, and scans and encodes the keypad 32 and operator interface buttons 35.

Figure 14:
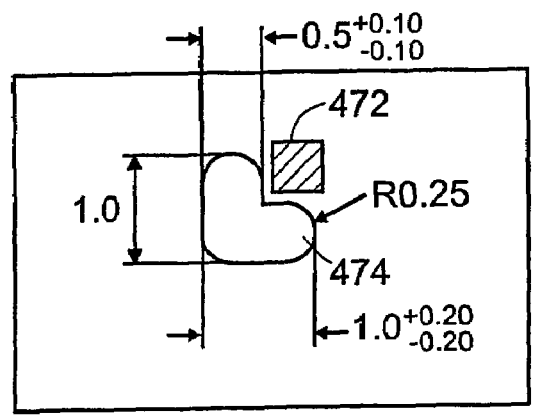
FIG. 14 is a schematic view of one embodiment of a physical mark.

FIG. 14 depicts one embodiment of a target zone mark 474, the dimensions of which are approximate and for illustrative purposes only. The mark 474 is essentially an "L" shape; however, the size and shape of the mark 474 can vary to suit a particular purpose. For example, the mark can include line segments, arcs, or combination thereof, which at least partially bound a target zone 472.

Figure 15A:
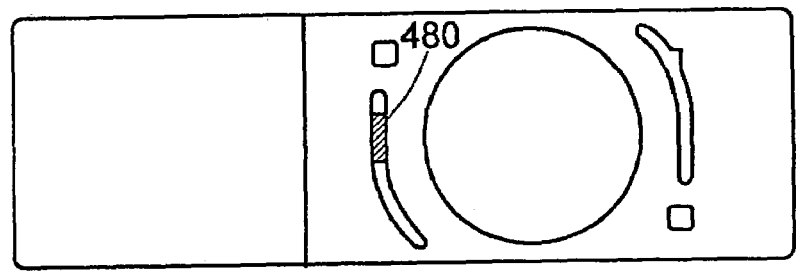
FIG. 15A is a schematic view of a specimen slide after being reviewed on a review system in accordance with the invention.
Figure 15B:
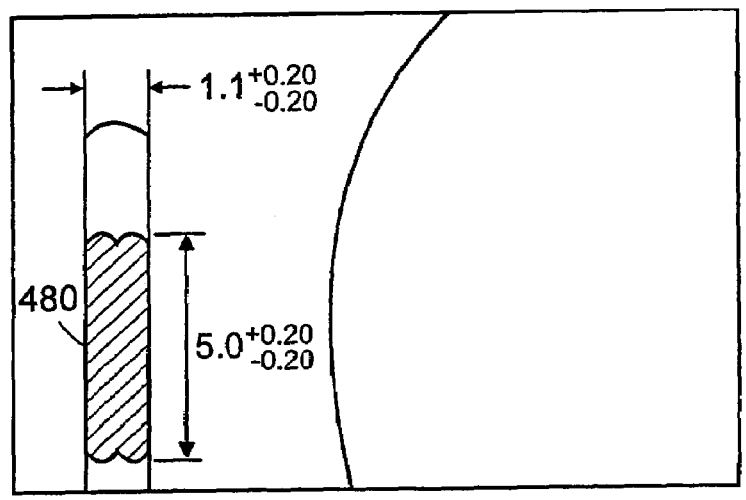
FIG. 15B is an enlarged view of a section of the specimen slide of FIG. 15A.

An embodiment of the slide reviewed mark 480 is shown in FIGS. 15A and 15B. The mark 480 is a vertical line about 1 mm thick and about 5 mm in height centered on a screen-printed left hand arc of the specimen slide shown in FIG. 15A. FIG. 15B is a partial enlarged view of FIG. 15A and shows dimensions, which are approximate and illustrative only, for one embodiment of a slide reviewed mark 480. The size and shape of the mark 480 can be selected from line segments, arcs, or combinations thereof.

Figure 17:
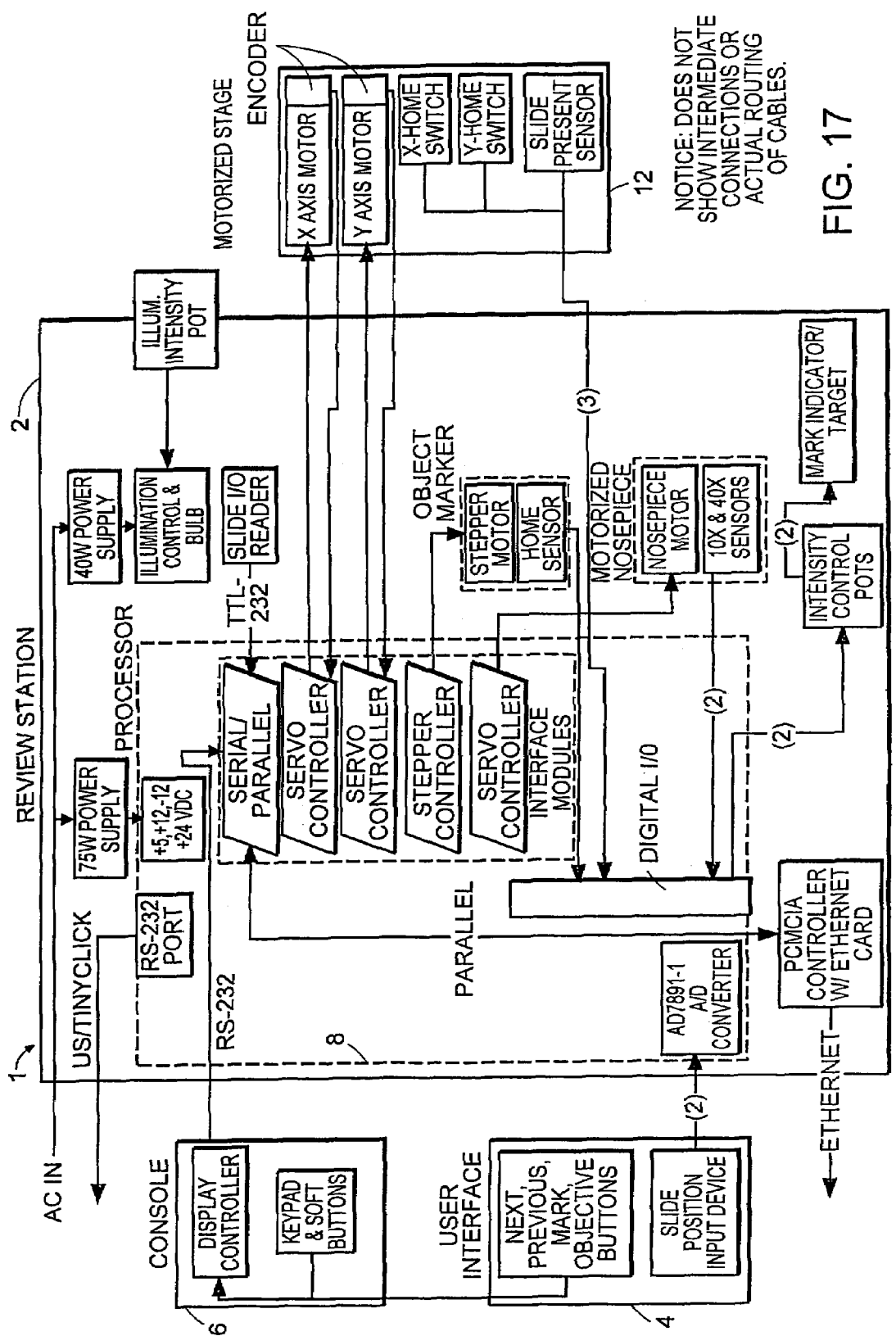
FIG. 17 is an electrical schematic of a review station in accordance with the invention.

FIG. 17 is a graphical representation of one possible electrical arrangement for an embodiment of a RS 1 in accordance with the invention.

Figure 18A:
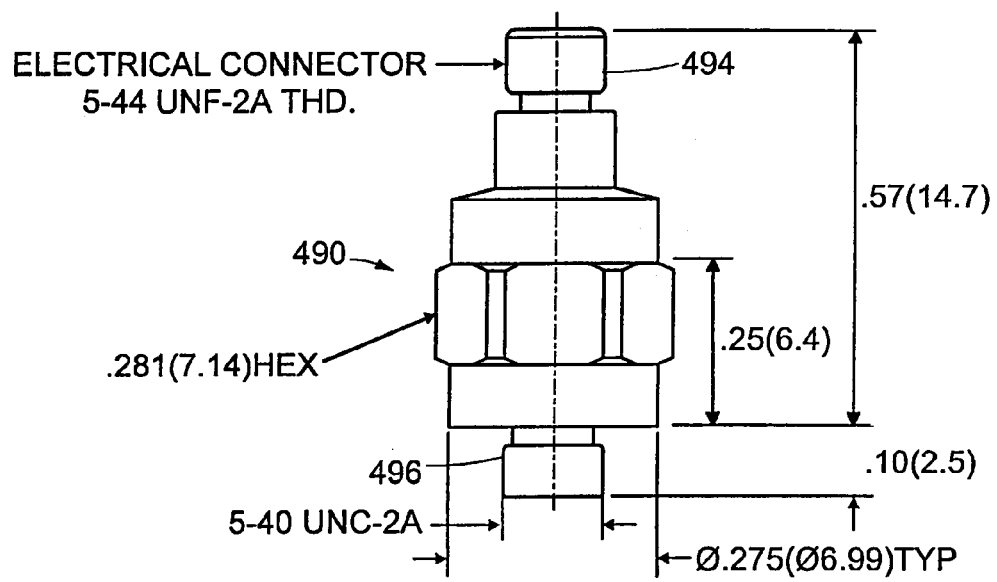
FIG. 18A is a schematic view of one embodiment of an accelerometer.

FIG. 18A depicts one embodiment of an accelerometer 490 that can be used with an imaging system for accommodating vibration errors that occur during imaging. The dimensions shown are approximate and for illustrative purposes only. The size and model accelerometer 490 used will vary to suit a particular application. The accelerometer 490 is typically a high-precision, high-resolution device utilizing a ceramic shear mode sensing element. The accelerometer 490 shown has a voltage sensitivity of 100 mV/g, a measurement range of +/−50 g [+/−491 ms2 peak] for +/−5V, a frequency range of 0.2 to 20,000 Hz (preferably 1 to 10,000 Hz), and an excitation voltage of 18-30 VDC/2-20 mA. The accelerometer 490 can be a commercially available product, such as model 352C66 available from PCB Piezotronics of Depew, N.Y. The accelerometer 490 includes an electrical connector 494 for electrical communication to a processor.

Figure 18B:
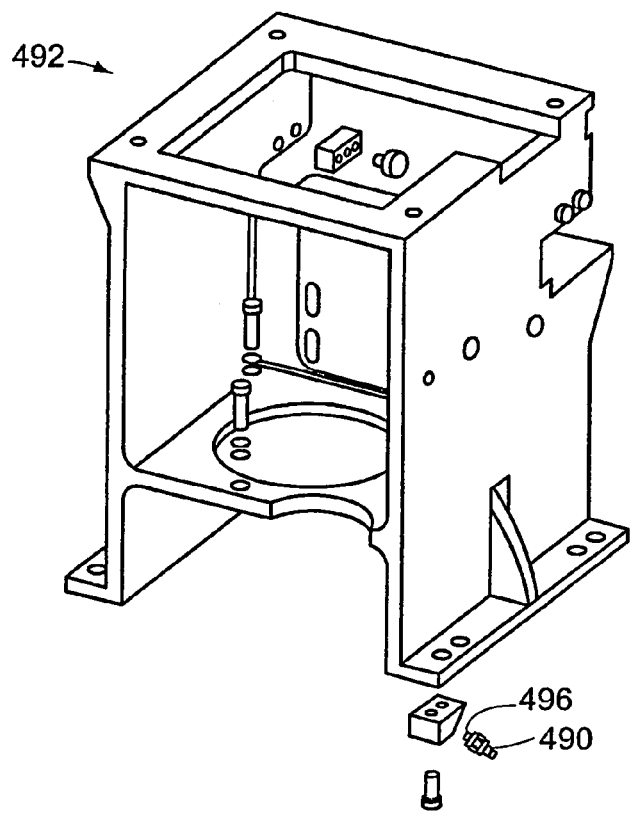
FIG. 18B is a schematic view of an imaging system structure with the accelerometer of FIG. 18A mounted thereon.

FIG. 18B depicts the accelerometer 490 of FIG. 18A mounted on one embodiment of a frame 492 for the imaging system. Mounting is via a threaded end 496 on the accelerometer 490; however, the mounting can be done via any known methods of fastening. The accelerometer measures the vibration the imaging system experiences while imaging a specimen. The vibration measurement is taken for each portion of the specimen that is imaged. If the measurement exceeds a set threshold, the system will re-image the portion of the specimen that was being imaged immediately following the vibration measurement. If the number of portions re-imaged exceeds a set threshold, the system may reject the specimen. Alternatively, if the vibration measurement exceeds a second set threshold, the system may reject the slide without re-imaging the specimen portion.

Figure 19:
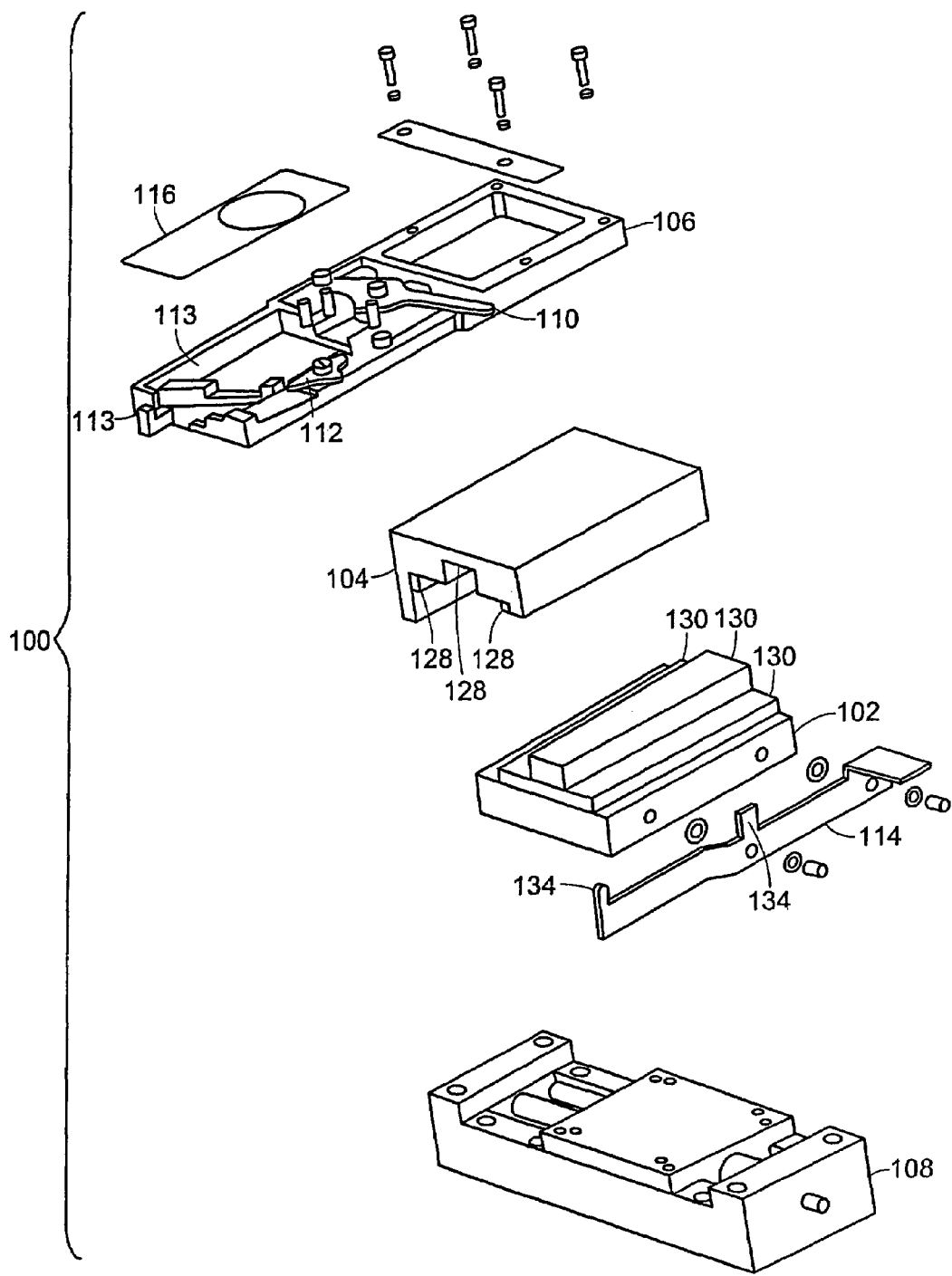
FIG. 19 is an exploded perspective view of one embodiment of a slide holder in accordance with the invention.

Referring to FIG. 19, one embodiment of the slide holder assembly 100 is shown. A first platform 104 of the slide holder assembly 100 is movably connected to a base 102. The first platform 104 slides relative to the base 102 via a series of rails 130 on the base 102 that contact mating surfaces 128 on the underside of the first platform 104. This movable relationship of the first platform 104 relative to the base 102 may be achieved by any suitable mechanism including, but not limited to, a tongue and groove mechanism, a sliding dove-tail joint, a roller assembly, a ball bearing assembly, or combination thereof. A second platform 106 is attached to the first platform 104. Attachment of the second platform 106 to the first platform 104 can be by welding, bonding, rivets, bolts, machine screws, or other suitable attachment methods. The base 102 can be connected to an actuating table 108. The connection between the base 102 and the actuating table 108 may be a permanent attachment or a temporary attachment, so that the base 102 may be detached from the actuating table 108 and a different embodiment of a slide holder assembly 100 may then be configured. The actuating table 108 itself may be fixed to ground or temporarily attached to a suitable support via a lock and release mechanism.

Respective upper surfaces of the base 102, the first platform 104, the second platform 106, and the actuating table 108 are shown as being substantially rectangular in shape; however, the shape of these surfaces may be circular, triangular, oval, elliptical, square, an irregular contour, or any other suitable geometric shape. In addition, the base 102, the first platform 104, the second platform 106, and the actuating table 108 may be any suitable three dimensional solids and are not limited to machined or molded rectangular solids.

The base 102, the first platform 104, the second platform 106, and the actuating table 108 may be made from the same or differing materials through molding, machining, casting, sculpting, cutting, etching, thermosetting, or other suitable fabrication process. The class of suitable materials for the base 102, the first platform 104, the second platform 106 and the actuating table 108 includes metals, alloys, woods, plastics, composite materials, resins, or any other sufficiently strong and durable material. Similarly, any component part of the holder assembly 100 may be made of any material as may be suitable to the operational requirements of the component part. In addition, any of the component parts disclosed in this specification and the various embodiments of the invention illustrated herein, may be hollow, solid, or a combination of both, as required for a particular application.

A first slide positioning member 110 and a second slide positioning member 112 are shown connected to the second platform 106. A stop 113, in this embodiment of the invention, is an edge wall of a recessed cavity within which the slide 116 may be positioned by the first slide positioning member 110 and the second 112 slide positioning member. The stop 113 may also be, for example a raised pin, a tab, a recessed cavity, a ridge, a groove, any combination of the preceding structures, or any other suitable slide restraining structure. In various embodiments of the invention, the slide 116 is preferably manufactured of float glass, which is extremely flat. The open configuration of the second platform 106 in this embodiment of the invention allows viewing, imaging, and marking systems easy access, in conjunction with robotic systems for slide positioning and transfer to and from the imaging system.

The slide actuating mechanism 114 in this embodiment is manufactured from formed sheet metal, although other suitable materials may be used. The first slide positioning member 110 and the second slide positioning member 112 engage the actuating mechanism 114 when the first platform 104 is moved relative to the base 102. This occurs, in part, because the actuating mechanism 114 is attached to the base 102. The actuating mechanism may be bolted, welded, chemically bonded, or otherwise physically connected to the base 102. The actuating mechanism 114 engages the first slide positioning member 110 and the second 112 slide positioning member at protrusions 134 extending from the actuating mechanism 114. Alternative actuating mechanisms include, a cam system, an actuating motor, an internal spring system, or other suitable apparatus or structure.

Still referring to FIG. 19, the biasing of the first 112 slide positioning member 110 and the second 112 slide positioning members towards the slide receiving area with a slide 116 in contact with the stop 113 is achieved by the presence of a first resilient member 120 and a second resilient member 118 in contact with the respective positioning members 110, 112. The slide positioning members 110, 112 are rotatably mounted to the second platform 106. The resilient members 120, 118 are connected to the positioning members 110, 112 so that when the resilient members contract, they cause the slide positioning members 110, 112 to rotate towards the slide receiving area. When the resilient members 120, 118 are springs, they may be connected to the slide positioning members 110, 112 and to the second platform 106 through drilled holes 132 in the members 110, 112, and the second platform 106 respectively. The resilient members 120, 118 and the positioning members 112, 110 may also be connected via chemical bonding, screws, bolts, catches, hooks, or other suitable means. The resilient members 120, 118 may be springs, elastic bands, collapsible shocks, or other suitable devices in various embodiments of the invention.

The resilient members 120, 118 bias the first 110 slide positioning member and the second 112 slide positioning member towards the slide receiving area. This biasing is opposed when the actuating mechanism 114 causes the slide positioning members 110, 112 to pivot away from the slide receiving area to facilitate removal of a slide 116 from the assembly 100. The actuating mechanism 114 in this embodiment of the invention has two raised protrusions 134. When the first platform 104 slides relative to the base in a first direction, the actuating mechanism 114, which is fixed to the base 102 makes contact with each slide positioning member 110, 112, such that one protrusion 134 contacts one member. The protrusions 134 move against the slide positioning members 110, 112 as the base 102 and first platform 104 continue to move relative to one another, in a first direction, which causes the members 110 and 112 to rotate away from the slide. When the base 102 and the first platform 104 move in the opposite direction, the protrusions 134 disengage from the positioning members 110, 112 and the tension supplied by the resilient members 120, 118 causes the respective slide positioning members 110, 112 to move toward and contact the slide 116, which moves the slide 116 into contact with the stop 113. The slide 116 is held in place by opposing contact forces originating from the stop 113 and the slide positioning members 110, 112 as biased by the resilient members 120, 118.

Figure 20:
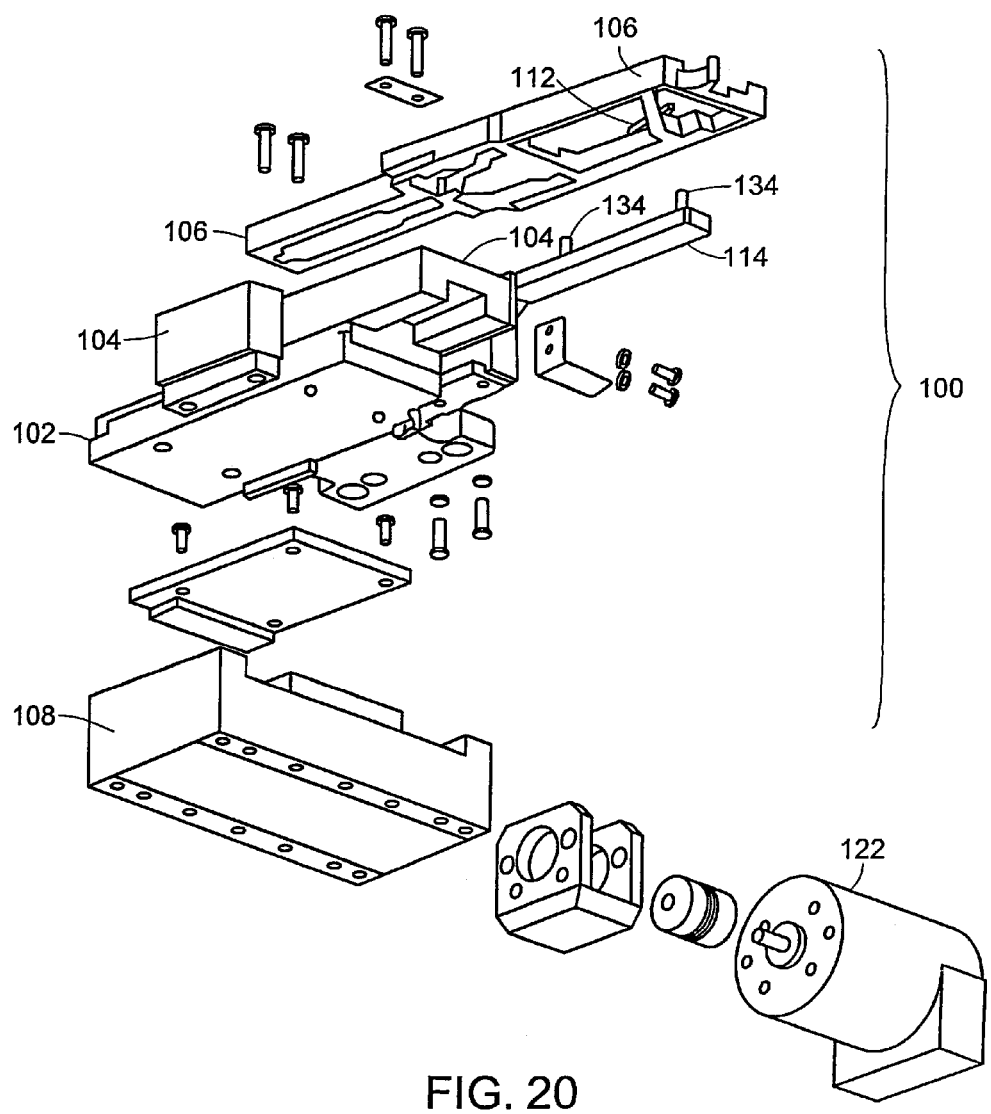
FIG. 20 is an exploded bottom perspective view of another embodiment of the slide holder in accordance with the invention.

Referring to FIG. 20, another embodiment of the slide holder assembly 100 is shown. In this view of the holder 100, only one slide positioning member 112 is visible. This embodiment is similar to that described herein above with respect to FIG. 19. For example, the base 102, the first platform 104, and the second platform 106 are very similar to those shown in FIG. 19. The embodiment shown in FIG. 20 does differ from that shown in FIG. 19 in some respects. For example, this embodiment depicts a motor 122 for driving the actuating table 108. The motor 122 may be a solenoid, servo, or any other suitable actuating device. In addition, this embodiment shows the actuating mechanism 114 as a solid machined member. The protrusions 134 extending from the solid member actuating arm 114 in FIG. 20 are raised round cylinders. This differs from the protrusions 134 in FIG. 19, which are shown as cut metal tabs.

Figure 21:
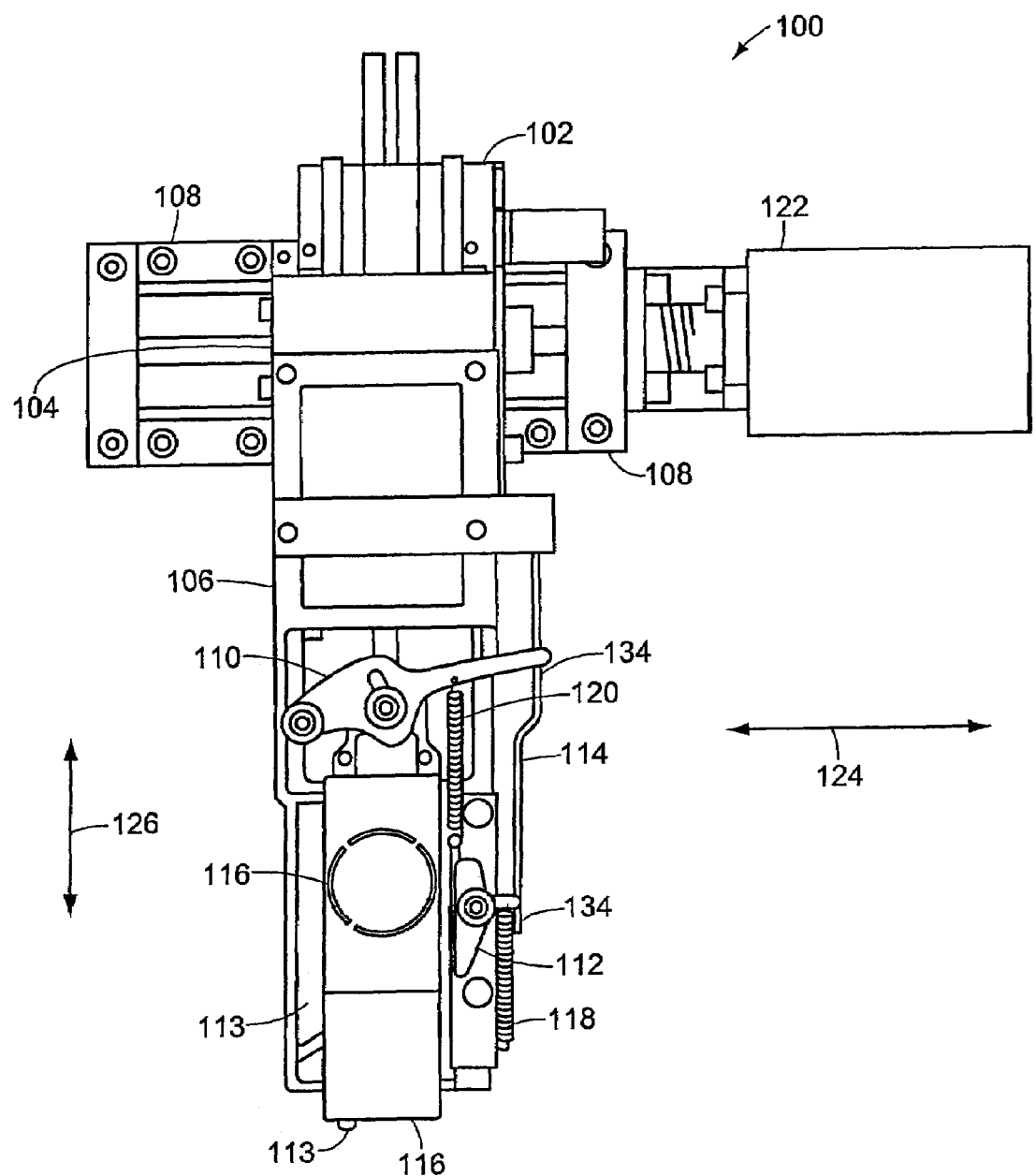
FIG. 21 is a schematic top view of the slide holder of FIG. 19.

Referring to FIG. 21, the arrow 124 illustrates the direction in which the actuating table 108 may move the base 102, the first platform 104, and the second platform 106. This view of the holder 100 shows a slide 116 in an unsecured position in the slide receiving area of the second platform 106 with the first slide positioning member 110 and the second slide positioning member 112 actuated away from the slide 116 by the protrusions 134 of the actuating mechanism 114. Arrow 126 illustrates the motion of the first platform 104 relative to base 102. The resilient members 120, 118 are connected to the second platform 106 and are oriented substantially parallel with the motion of the platform. Arrow 126 shows one possible axis of motion of the base 102 relative to the first platform 104. The resilient members 118, 120 exert a force on the first positioning member 110 and the second positioning member 112, respectively, to engage the slide 116. When the first platform 104 moves, the slide positioning members 110, 112 contact parts of the actuating mechanism 114, such as the protrusions 134. The contact between the slide positioning members 110, 112 and the actuating mechanism 114 creates a force which opposes the biasing of the positioning members 110, 112 by the resilient members 120, 118 towards the stops 113 of the slide receiving area. The biasing opposing force of the actuating mechanism 114 may be adjusted by the movement of the first platform 104 so that the first and second slide positioning members 110, 112 come into secure contact with the slide 116, thereby moving it into secure contact with the stop 113. The stop 113 is defined as any slide position restricting element. In some embodiments of the invention, a slide restraining system such as a series of vacuum channels, may be incorporated into the assembly 100 to exert a normal force on the slide 116 to hold the slide 116 firmly in place on the second platform 106 once against the stops 113.

Figure 22:
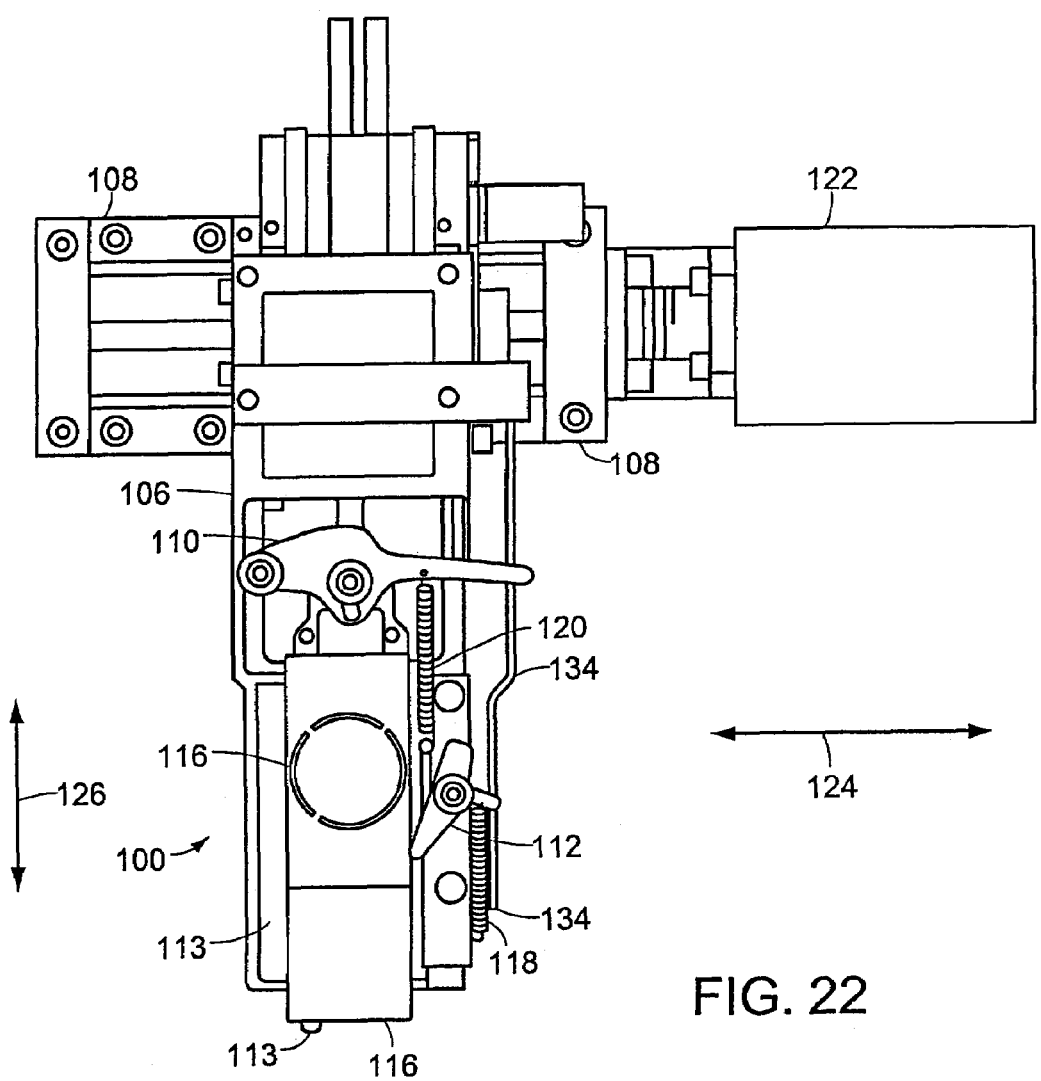
FIG. 22 is a schematic top view of the slide holder of FIG. 21 with slide positioning members securing a slide against two stops.

FIG. 22 shows the same embodiment of the invention as shown in FIG. 21, but with the actuating mechanism 114 in a different position as a result of the first platform 104 being moved with respect to the base 102. The motion of the first platform 104 and the disengagement of the actuating mechanism 114 from the slide positioning members 110,112 causes the slide positioning members 110,112 to contact the slide 116 and secure it in a position abutting the stops 113. The slide positioning members 110, 112 are shown in a slide contacting position. The slide 116 is secured between the members 110, 112 and the stops 113.

Figure 23:
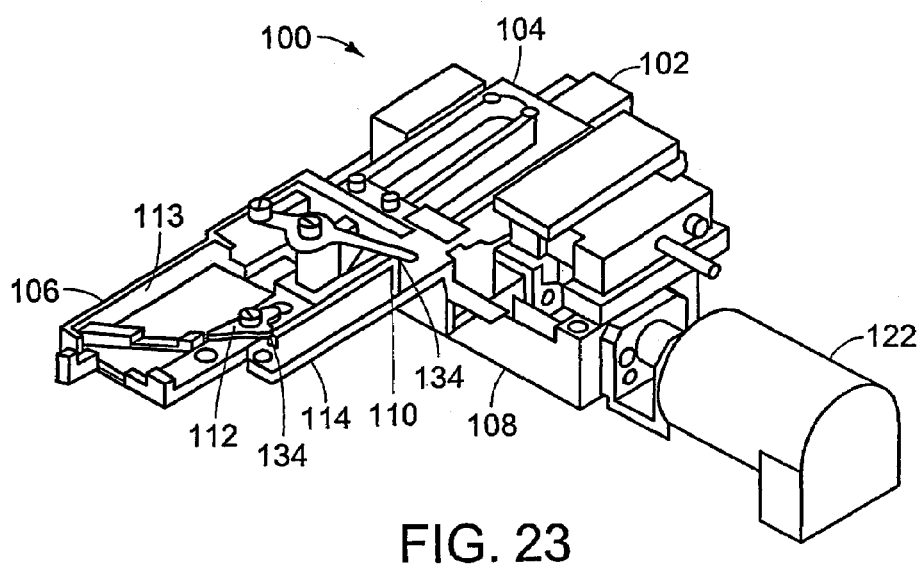
FIG. 23 is a perspective view of the slide holder of FIG. 20.

FIG. 23 depicts a perspective view of the slide holder assembly 100, wherein the actuating mechanism 114 is restraining a first slide positioning member 110 and a second slide positioning member 112 in an open state.

Figure 24:
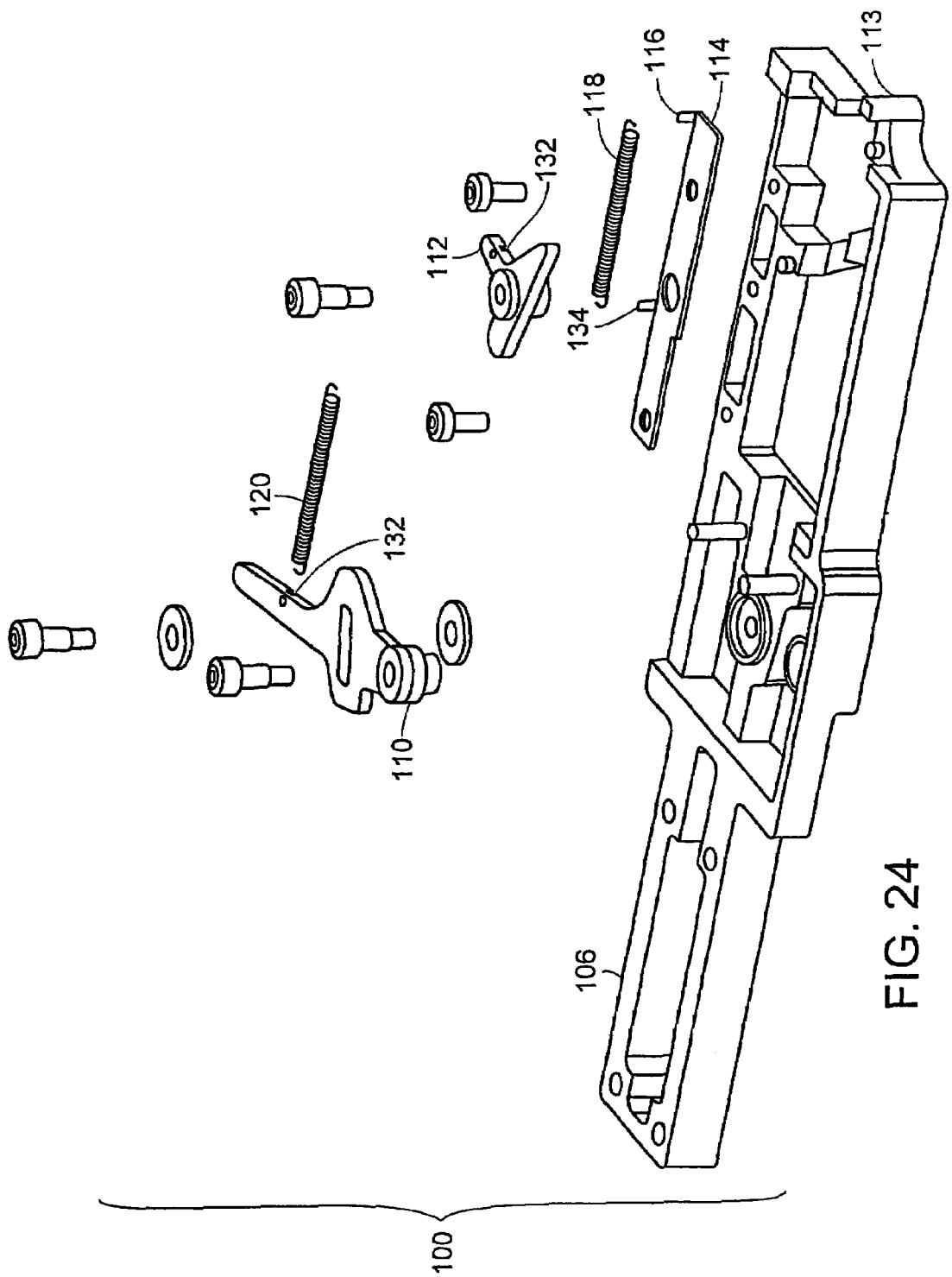
FIG. 24 is an exploded perspective view of one embodiment of a second platform for use with a slide holder in accordance with the invention.

Referring to FIG. 24, some of the constituent parts of some embodiments of the invention are shown. The second platform 106 is shown as a machined or cast metal frame with pre-drilled holes in this embodiment of the invention. The first slide positioning member 110 and the second slide positioning member 112 are shown in position to be rotatably mounted to the second platform 106. A first resilient member 120 and a second resilient member 118 are in position to be connected to their respective slide positioning members 110,112. The resilient members 120, 118 are metal springs in this embodiment of the invention. A raised stop 113 is fabricated as part of the metal frame forming the second platform 106.

Figure 25:
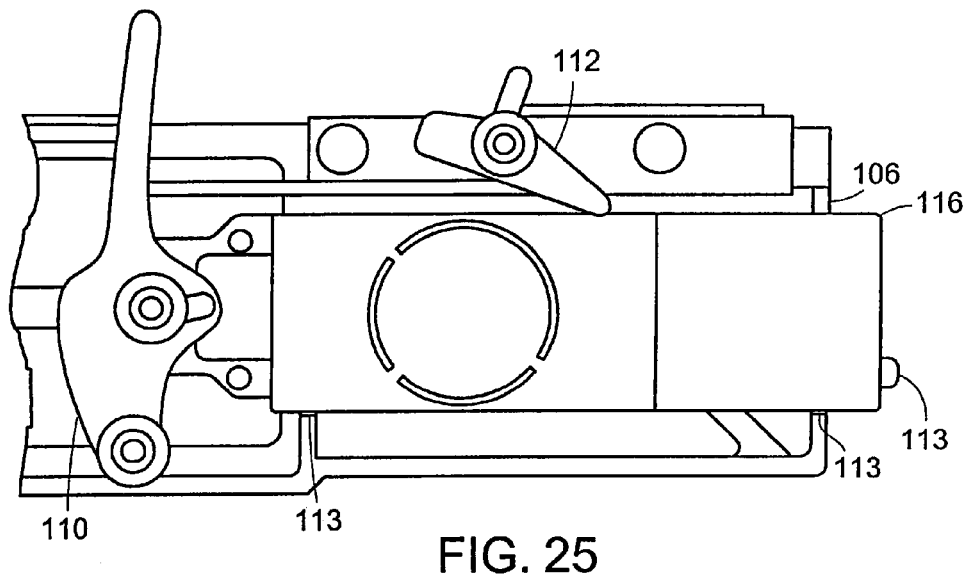
FIG. 25 is a partial schematic top view of the slide holder of FIG. 19 including a slide.

Referring to FIG. 25, a close up the slide receiving area is illustrated, wherein the slide 116 is shown in a position secured by a first slide position member 110, a second slide positioning member 112, and various stops 113. The first slide positioning member 110 is shown in contact with the slide 116 at a contact region at an end of the slide 116. Similarly, the second slide positioning member 112 is shown in contact with the slide 116 at another contact region along an edge of the slide 116. When the slide 116 is in this position, the actuating table 108 may be used to move the slide 116, as desired, under imaging optics.

Figure 26A:
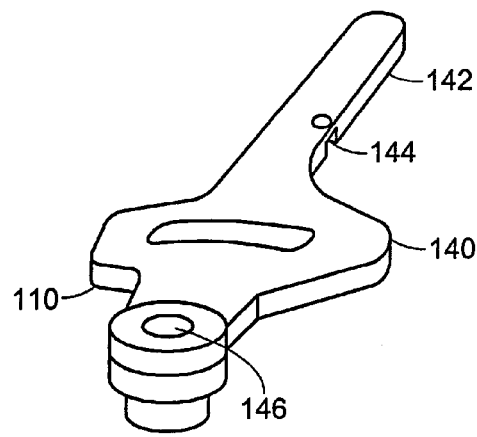
FIGS. 26A and 26B are perspective views of two embodiments of slide positioning members.
Figure 26B:
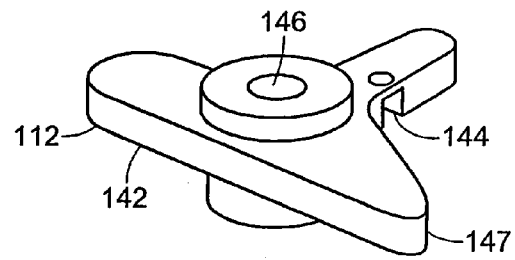

Referring to FIG. 26A one embodiment of the first slide positioning member 110 is shown. Similarly, referring to FIG. 26B, one embodiment of the second slide positioning member 112 is illustrated. These embodiments of the slide positioning members 110, 112 are depicted in FIG. 24 prior to their assembly to the second platform 106. The slide positioning members 110, 112 each have a slide contacting end 140, an actuating mechanism contacting region 142, a resilient member attachment point 144, and pivot region 146 for mounting to the second platform 106. The slide holding members 110, 112 may take on any geometric shape that allows them to be mounted to the second platform 106, while retaining the ability to move, make contact with a slide 116, and be operatively engaged and disengaged from the slide 116 by an actuating mechanism 114. The configuration of the slide positioning members 110, 112 and the protrusions 134 can be designed so that both members 110, 112 actuate simultaneously or serially, as desired. In various embodiments slides 116 designed for use with cytological specimens may be used. Slides 116 that contain cytological specimens stained with thionin-phenol solutions, including stains with phenol derivatives are well suited for use in the assembly 100.

Figure 27:
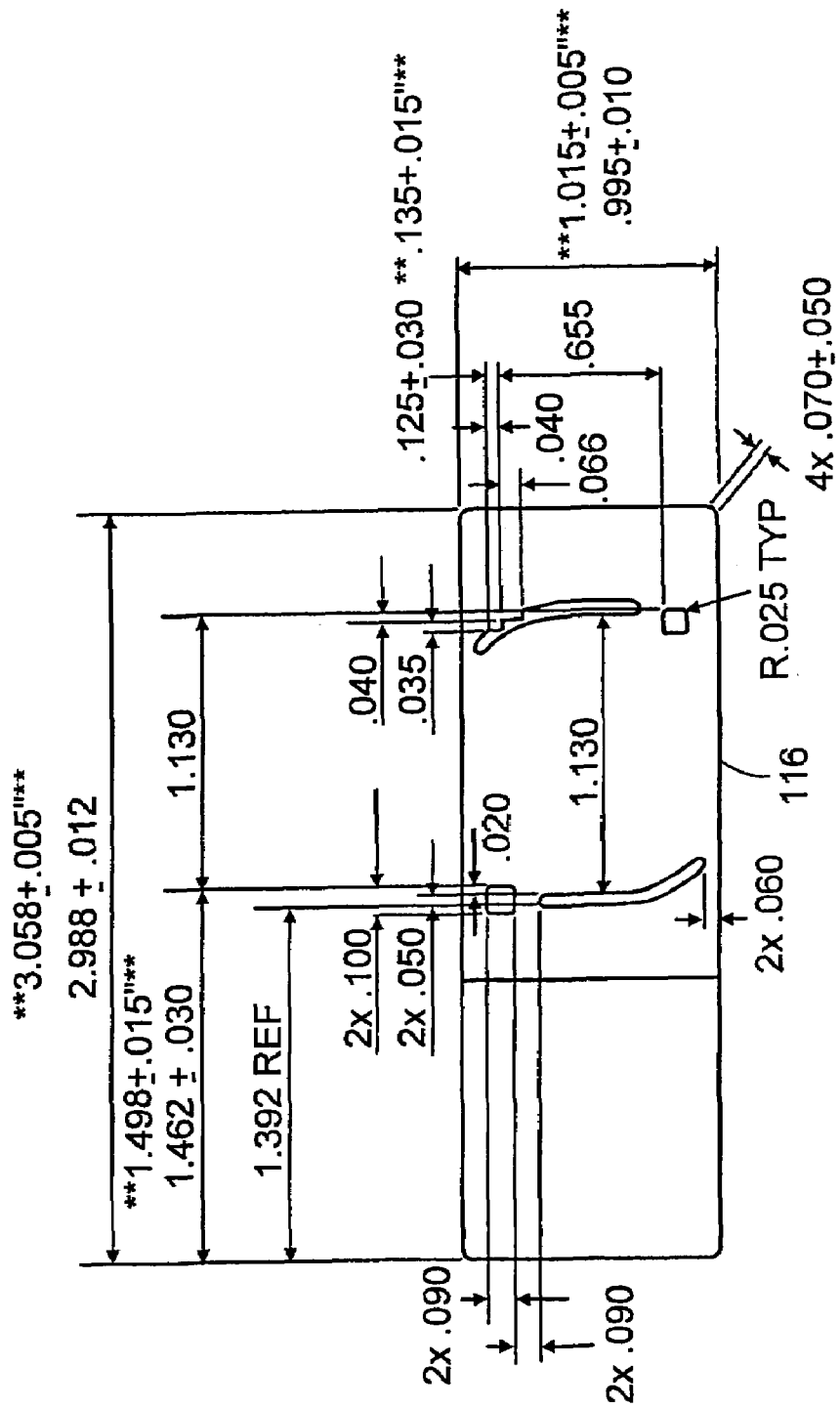
FIG. 27 is a schematic diagram illustrating various manufacturing tolerances for one embodiment of a float glass slide for use in the present invention.

Referring to FIG. 27, one embodiment of a slide 116 for use in the invention is shown. A float glass slide 116 is depicted with various dimensions and tolerances in inches for its fabrication. Float glass is made by forming a layer of molten glass on a molten metal such as tin and subsequently cooling the molten glass to solidification. Because of the method of manufacture, the glass surface is extremely flat, obviating the surface irregularities and waviness inherent in producing glass with rollers. Other types of slides 116 may also be used in various embodiments of the invention.

Figure 28:
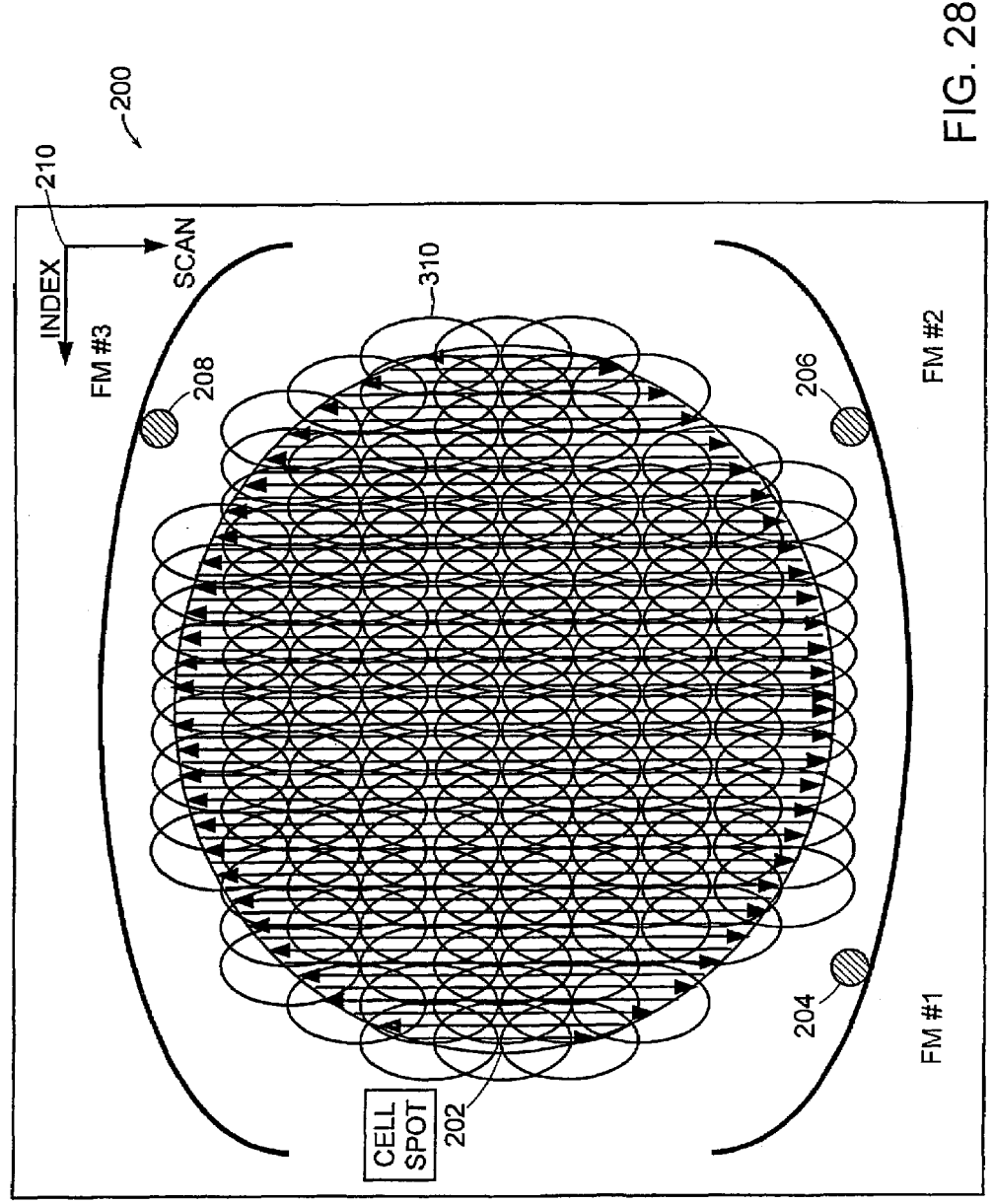
FIG. 28 is a schematic representation of a pattern of fine focus jurisdictions across a cell spot in accordance with the invention.

FIG. 28 includes a schematic representation of a generally circular cell spot 202 on a slide 200 to be imaged. The cell spot 202 is the region of interest of this slide, on which a cytological specimen lies, for instance. The cell spot 202 may be roughly two centimeters in diameter. In one embodiment of the invention, it is desired to acquire images covering substantially all of the cell spot 202 and which deviate from an optimal focus position no greater than about ±4 µm, as measured by position of an optical component along the focus axis generally normal to the plane of the slide 200. In this embodiment it is further desired to complete the imaging of the cell spot 202 of the slide 200 quickly, for example within 165 seconds or less.

An embodiment of the invention utilizes three fiducial marks 204, 206, 208 depicted in FIG. 28 located at predetermined coordinate locations on the slide 200. In this embodiment, the fiducial marks 204, 206, 208 have a known shape with a rapid transition from dark to light when in focus. By identifying and recording the optical component focus axis location at which a sharp edge transition occurs, the global focal surface (in this case, a plane) containing the sample can be estimated. This estimated global focal plane serves as a guide across the complete cell spot and helps to establish a boundary condition that the focus axis should not extend beyond under normal operating conditions.

Figure 29:
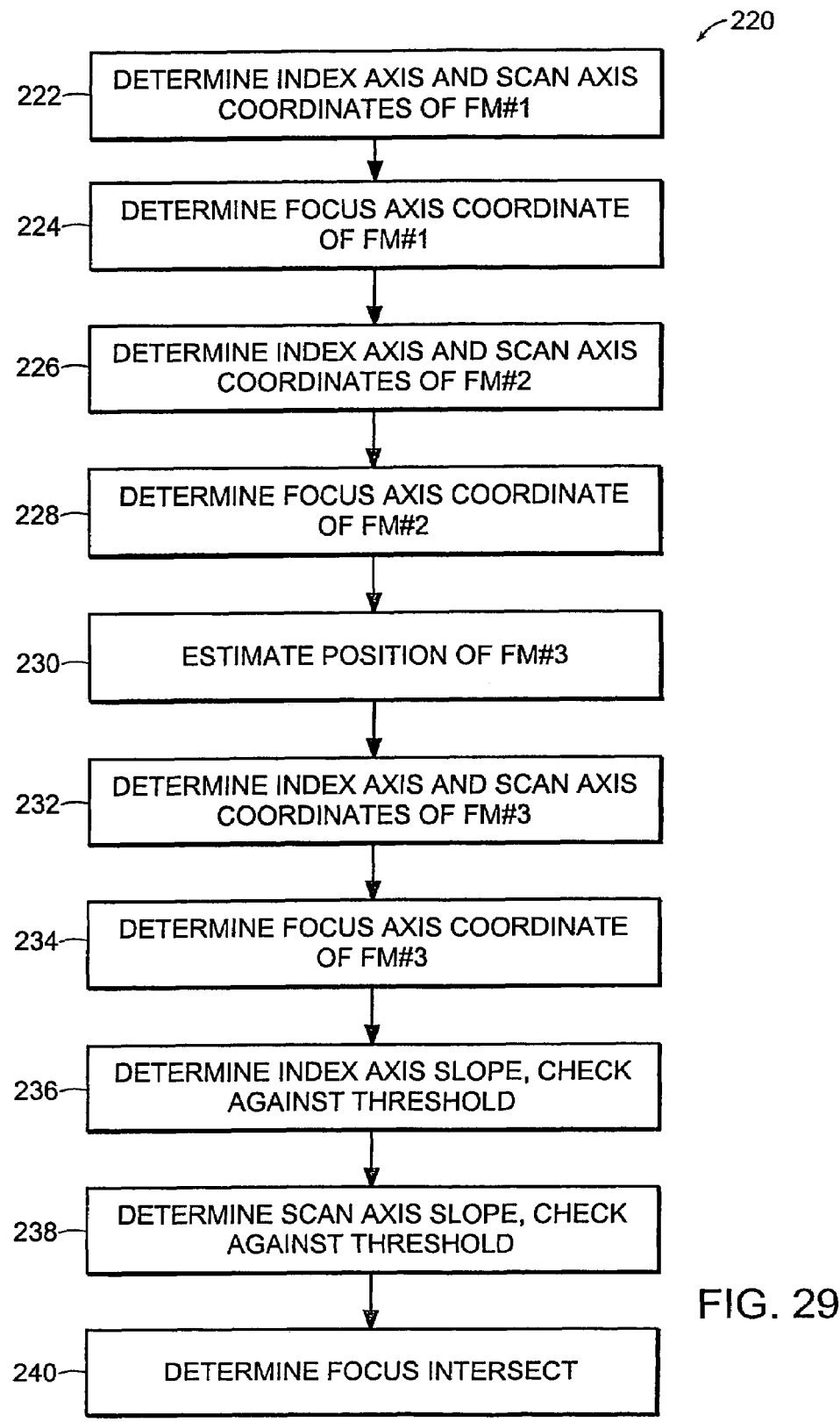
FIG. 29 is a schematic representation of a global focal surface determination flowchart summarizing certain process steps in accordance with the invention.

FIG. 29 is a schematic representation of a global focal surface determination flowchart 220 summarizing certain process steps in accordance with one embodiment of the present invention. In this embodiment, a system is contemplated which includes a two-axis slide imaging stage. The two orthogonal axes are the index and scan axes 210 shown in FIG. 28. At a given time, the system may perform either a coarse positioning move to get close to a desired location, or a scan movement. In this embodiment, a scan pass from one edge of the cell spot 202 to an opposite edge includes of a series of short moves, each approximately 370 µm long. Motion may be provided by a Piezo Ceramic Linear Motor (PCLM) packaged by the Anorad Corporation under the name of Pico Stage. Also, a linear encoder reports the actual position of the stage. The stage may be guided along its axis using crossed roller bearings. An optical sensor may be provided to indicate home position of the stage. The scan axis supports the slide holder and mounts normal to the index axis, in this embodiment. Naturally, other motion systems could be employed and will be apparent to those skilled in the art.

FIG. 29 shows that according to one embodiment, the first step 222 in determining the global focal surface is to determine the index axis and scan axis coordinates of the first fiducial mark, which is shown as FM#1 204 in FIG. 28. In this embodiment, the centroid of FM#1 204 is determined to within ±10 µm of the stage home position for the first fiducial mark FM#1 204. In step 224 of FIG. 29, the focus axis coordinate corresponding to FM#1 204 is determined. This is done by performing a coarse focus action at a position corresponding to FM#1 204. In this embodiment, a coarse focus action is performed by imaging FM#1 204 at an initial physical position, here, a z-position, which corresponds to a coordinate on the focus axis, and by determining a focus score corresponding to that coordinate. One method of determining a focus score, developed by Brenner et al. ("An Automated Microscope for Cytological Research: A Preliminary Evaluation," Brenner et al., The Journal of Histochemistry and Cytochemistry, Vol. 24, No. 1, pp. 100-111, 1976, the disclosure of which is incorporated herein by reference in its entirety), is to calculate the average change in gray level between pairs of points separated by n pixels, as follows:

$$f(z) = \sum_j \sum_i \{G_i(z) - G_{i+n}(z)\}^2 \quad (1)$$

where the index (i) ranges over all image points, in order, along a scan line (j); n is a small integer, especially 2; z is the focus axis position; and $G_i$ is the transmission gray level for point i. It is then desired to obtain a scan axis coordinate which provides a maximum value of focus score, f(z).

Figure 30:
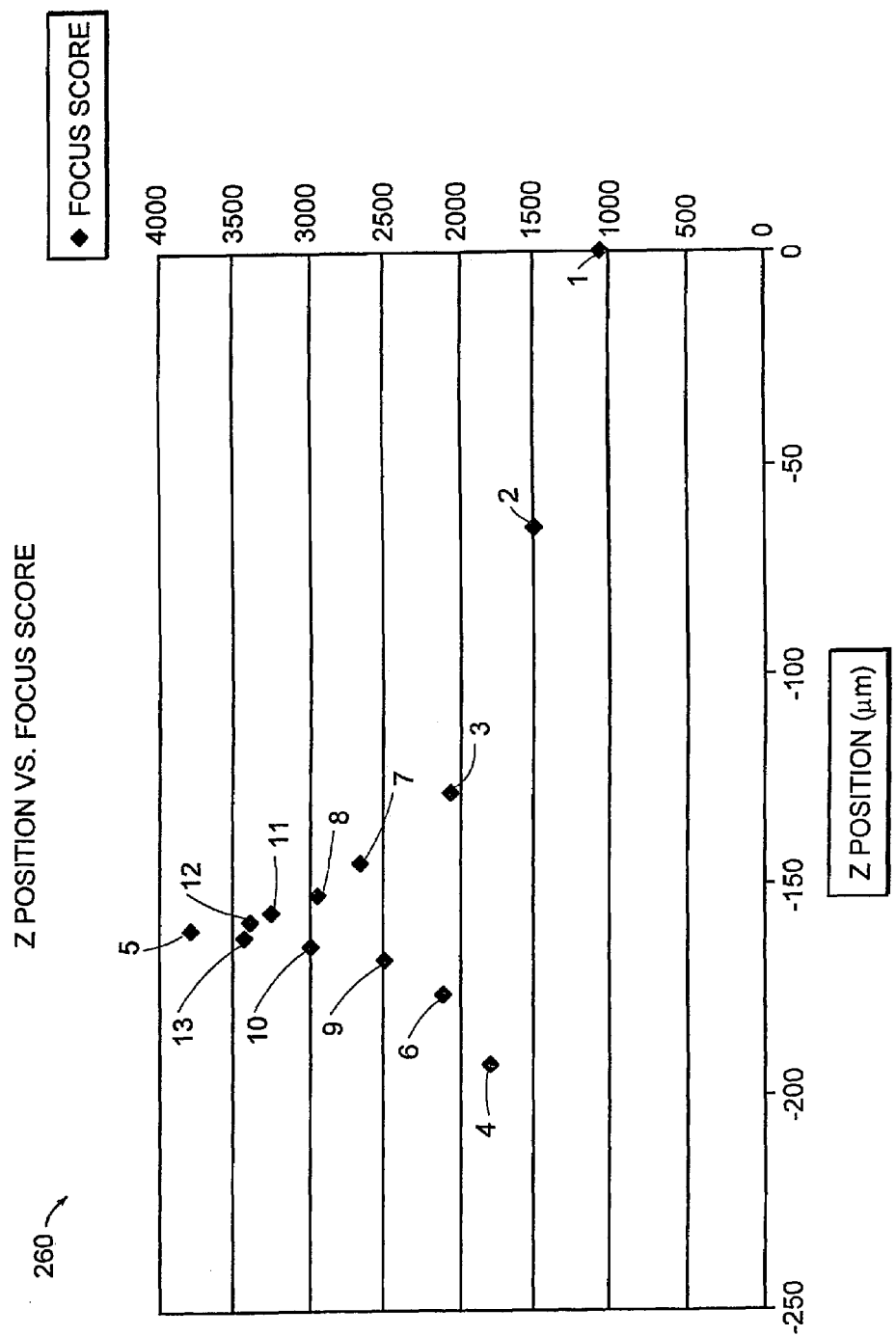
FIG. 30 is a schematic representation of a sample plot of focus axis position versus focus score in accordance with the invention.

FIG. 30 is a schematic representation of a sample plot of focus axis position versus focus score in accordance with one embodiment of the present invention. The plot 260 of FIG. 30 shows values of focus score, f(z), at positions corresponding to various coordinates on the z-axis (focus axis). One embodiment of the invention applies an algorithm to facilitate the determination of a z-axis (focus axis) coordinate to within ±4 µm of the coordinate providing the maximum focus score. In this embodiment, the imaging optics include an objective lens (numerical aperture of 0.25, magnification of 10×), a relay or tube lens (magnification of 1.8×), and a camera. The camera is used to capture images of discrete portions of the slide, and has the following features: an 8-bit resolution (providing 256 gray-scale values); progressive scan (non-interlaced) analog video signal to reduce the effect of any movement or vibration during image capture; asynchronous trigger reset mode, to allow for synchronized image capture; 25 Hz frame rate (minimum) for maximum throughput; square 8.3 µm pixels, square to eliminate x-y scaling and an 8.3 µm size to reduce magnification requirements thereby increasing the depth of field; 782×582 pixel array size, the minimum array size for the desired resolution; a sensitivity of 400 Lux, F4 for imaging; external electronically controlled shutter; a standard "C" mount for attachment; and a horizontal frequency of about 15,625 kHz, providing for a pixel clock rate of about 12 MHz. The use of a Sony model SC-8500CE (Sony Electronics Inc., USA) camera is consistent with these specifications.

The algorithm used in this embodiment during the coarse focus procedure applied at the first fiducial mark FM#1 204 is as follows, and is depicted in the plot 260 of FIG. 30. A picture is taken at an initial z-position (z=0) and its focus score, f(z) of Equation (1), is calculated. This is the first point, and the resulting focus score is depicted at box 1 of FIG. 30 (the boxed points are labeled in FIG. 30 according to the order in which they are measured). This score is set as the temporary maximum score. The position of the focus axis is then moved 64 µm below the initial z-position, relative to the surface of the slide. Note that this may be done either by moving an element of the optical system or by moving the slide, although moving an element of the optical system is generally easier. The position is imaged, and a focus score is determined at that position, depicted at box 2 of FIG. 30. The second focus score is compared to the first focus score. If the second focus score is less than the first focus score, then the focus axis is moved to a position 64 µm above the initial z-position. If the second focus score is greater than the first focus score, then the temporary maximum score is reset as the second focus score. The focus axis is moved in 64 µm increments until an image is captured at a z-position with a lower focus score than the current maximum focus score. In FIG. 30, the z-position corresponding to the point depicted at box 4 is just such a z-position. The idea is to continue making relatively large moves until an image has been captured on either side of a peak. Once the peak has been narrowed down to a 64 µm range, the current step size is divided by two. The focus axis is moved to the z-position substantially equidistant from the two positions on either side of the peak. A new image is taken and focus score calculated. If the score is greater than the maximum, the step size is divided by two again, and the next z-position is set to the current z-position plus the new step size. The process is continued until the step size reaches either 4 µm, 2 µm, or other predetermined small value, as shown in FIG. 30, and the image with the highest focus score is returned, which would be the image corresponding to the fifth z-position in the plot 260 of FIG. 30.

Thus, a value of focus axis coordinate is obtained for fiducial mark FM#1 204, thereby completing step 224 of FIG. 29. The next step 226 in determining the global focal plane in this embodiment is to determine the index axis and scan axis coordinates of the second fiducial mark, FM#2 206, shown in FIG. 28. In this embodiment, the centroid of FM#2 206 is determined to within ±10 µm of the stage home position for the second fiducial mark FM#2 206. After steps 222 and 226, where index axis and scan axis coordinates are determined, the embodiment will generate a slide error and flag the slide electronically or physically if the distance between FM#1 204 and FM#2 206 is greater than 500 µm. After step 226, the embodiment includes the performance of another course focus procedure, as discussed above, to complete step 228, the determination of a focus axis coordinate of FM#2 206. Then, the x-y position (index axis and scan axis coordinates) of the third fiducial mark, FM#3 208 of FIG. 28, is estimated based on the positions of FM#1 204 and FM#2 206. The stage is then moved to capture an image at this calculated position. If the third fiducial mark, FM#3 208, is greater than 300 µm from the computed location, the search results are rejected. Also, the slide is flagged and rejected if a fiducial mark cannot be located. Assuming the third fiducial mark is found, a coarse focus action is performed to determine the focus axis coordinate of FM#3 208, completing step 234 of FIG. 29. Step 236 is the determination of an index axis slope based on the coordinates for FM#1 204 and FM#2 206, which may be performed by computing the following quotient:

$$\text{index axis slope} = (z_2 - z_1)/(x_2 - x_1) \quad (2)$$

where $z_2$ is the focus axis coordinate of FM#2 206, $z_1$ is the focus axis coordinate of FM#1 204, $x_2$ is the index axis coordinate of FM#2 206, and $x_1$ is the index axis coordinate of FM#1 204. In this embodiment, the index axis slope is checked against a threshold value, for example, 2 µm focal axis distance over 25 mm along the index axis. If the index axis slope is greater than the threshold value, the slide is flagged and denoted physically or electronically as having an error. Step 238 of FIG. 29 is similar to step 236. Here, the scan axis slope is determined by calculating the following quotient:

$$\text{scan axis slope} = (z_3 - z_2)/(y_3 - y_2) \quad (3)$$

where $z_3$ is the focus axis coordinate of FM#3 208, $z_2$ is the focus axis coordinate of FM#2 206, $y_3$ is the scan axis coordinate of FM#3 208, and $y_2$ is the scan axis coordinate of FM#2. In this embodiment, the scan axis slope is checked against a threshold value, for example 2 µm focal axis distance over 25 mm along the scan axis (although this value does not necessarily have to be set equal to the threshold value for the index axis slope). If the scan axis slope is greater than the threshold value, the slide is flagged and denoted physically or electronically as having an error. A focus intersect is calculated in step 240 to complete the characterization of the global focal plane in this embodiment as follows:

$$\text{focus intersect} = z_1 - (\text{index axis slope}) * x_1 - (\text{scan axis slope}) * y_1 \qquad (4)$$

where $x_1$, $y_1$, and $z_1$ are the index axis, scan axis, and focus axis coordinates, respectively, at the point corresponding to the position of fiducial mark FM#1 204; and the index axis slope and scan axis slope are as determined in Equations (2) and (3), respectively.

Figure 31:
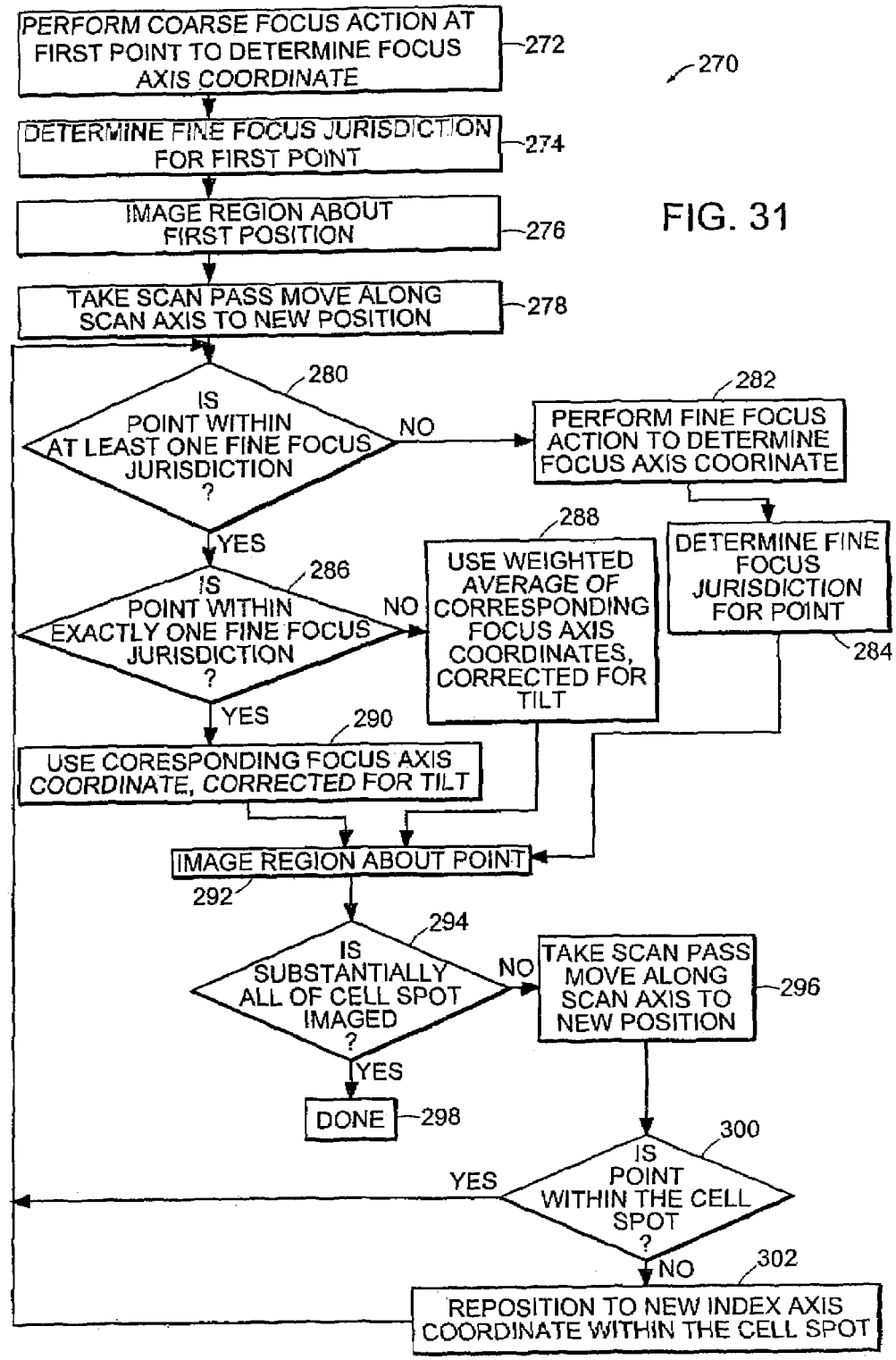
FIG. 31 is a schematic representation of a scan pass flowchart summarizing certain process steps in accordance with the invention.

Another embodiment of the invention involves the performance of a scan pass over the area of interest of a slide. FIG. 31 is a schematic representation of a scan pass flowchart 270 summarizing certain process steps in accordance with one embodiment of the present invention. In step 272 of FIG. 31, a coarse focus action, as discussed above, is performed at a first position on the area of interest of the slide. In one embodiment, this first position corresponds to the estimated center of the cell spot 202 on the slide. The scan pass starts at the center of the cell spot, and moves radially outwardly. This maximizes coverage of the cell spot and enhances efficiency of the scan process. The embodiment takes advantage of the implementation of an initial coarse focus followed by periodic fine focus actions during the scan pass. In one embodiment, a coarse focus begins by moving the focus axis relative to the surface of the slide to a position corresponding to a focus axis coordinate and incrementally raising and lowering the stage, searching for the location at which the focus score of the image is at a maximum. Unlike coarse focus actions, fine focus actions begin with the assumption that the current location is close to an in-focus location. Consequently, the search pattern for fine focus actions is more efficient.

Step 274 of FIG. 31 is the determination of a fine focus jurisdiction for the first point. The concept of a fine focus jurisdiction of this embodiment allows more efficient performance of the scan pass, such that focus actions do not have to be performed at each location at which an image is acquired. Instead, a focus action (coarse or fine) has a "jurisdiction" of influence, wherein any other image can reasonably rely upon that previous focus action for guidance on the focal plane. Note that FIG. 31 uses the term "fine focus jurisdiction," whether the focus action taken at a given point is coarse or fine. A focus action jurisdiction in this embodiment is defined as having a range of ±6 images along the scan axis and ±3 images along the index axis. An elliptical jurisdiction pattern applies for images that are not exactly along the scan or index axes from a previous fine focus action. If a new image is not within any focus action jurisdiction, then a new focus action occurs.

Figure 32:
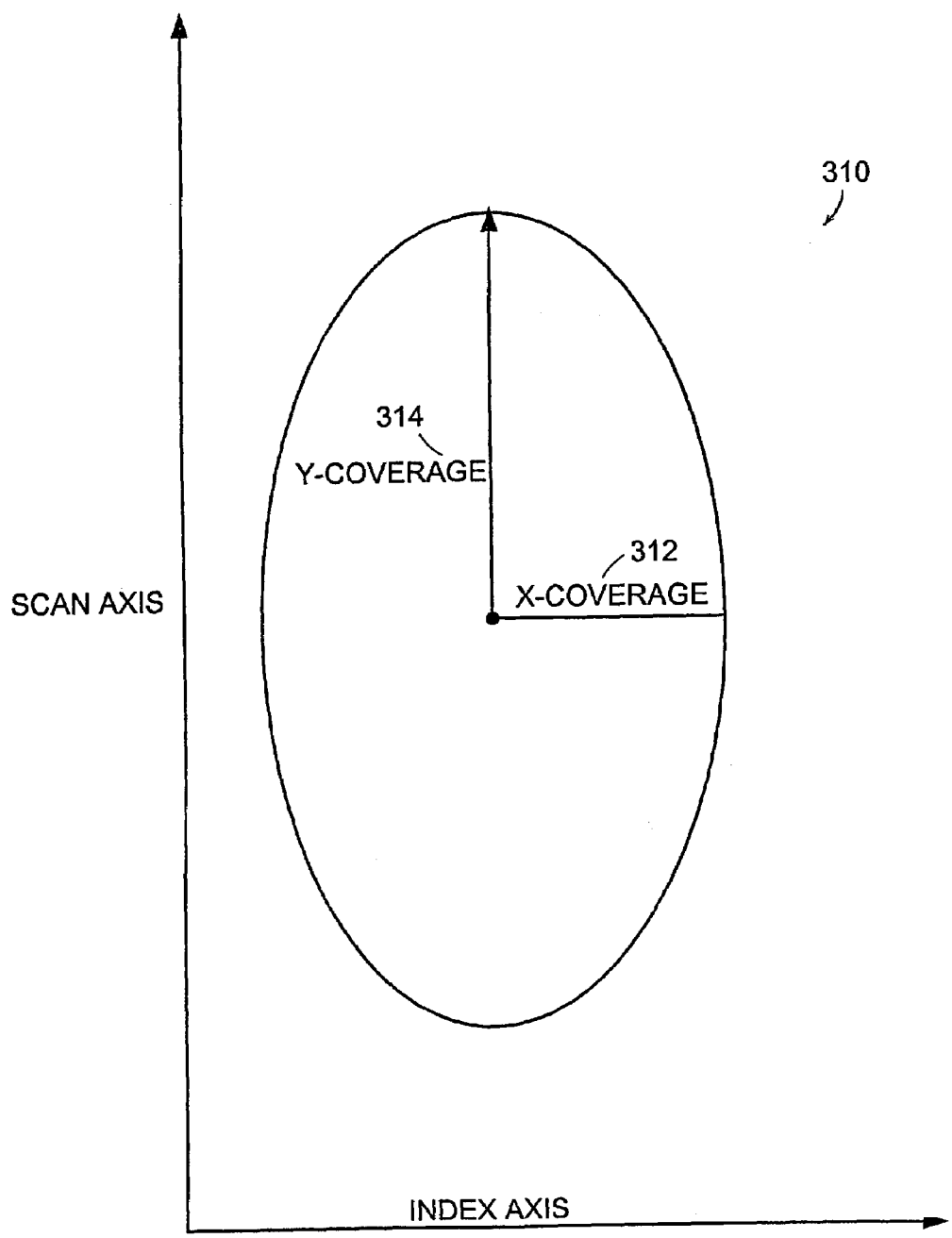
FIG. 32 is a schematic representation of an area of fine focus jurisdiction in accordance with the invention.

FIG. 32 is a schematic representation of an area of fine focus jurisdiction in accordance with one embodiment of the present invention. In this embodiment, the focus action jurisdiction 310 is generally elliptical in shape and has associated with it a predetermined length $X_{coverage}$ 312 along the minor axis of the ellipse and a predetermined length $Y_{coverage}$ 314 along the major axis of the ellipse. Also, in this embodiment the major axis of the ellipse is parallel to the scan axis, and the minor axis of the ellipse is parallel to the index axis.

An embodiment of the invention begins with a fine focus action to determine the focus score of the image at the best guess of the in-focus z-coordinate, determined using the representation of the global focal surface, as in FIG. 29. In this embodiment, from the best-guess location, up to four more images may be taken and scored. These represent images that are taken at +4, +8, −4, and −8 µm from the best guess location. The image with the highest corresponding score is declared the in-focus image.

Step 276 of FIG. 31 is the imaging of a region about the first point. A typical size of the area imaged during a single exposure in this embodiment is 640×480 pixels, but may vary according to the camera used. There are approximately 2500 frames over the cell spot depicted in FIG. 28.

In step 278 of FIG. 31, a scan pass move is made along the scan axis to a new position. In step 280, it is determined whether the new position corresponds to a point which is within at least one previously-determined fine focus jurisdiction. If not, a new fine focus action is performed to determine an appropriate focus axis coordinate at the new position, as shown in step 282, followed by the determination of a fine focus jurisdiction surrounding the new position, shown in step 284. In one embodiment, step 282 is performed using an initial estimate of an appropriate focus axis coordinate based on the determination of the global focal surface as shown in FIG. 29.

If the new position corresponds to a point which is determined to be within at least one previously-determined fine focus jurisdiction, step 286 determines whether the point is within exactly one fine focus jurisdiction. If so, step 290 prescribes the use of the corresponding focus axis coordinate correlated with the one fine focus jurisdiction, corrected for tilt. The tilt correction in this embodiment is based on the global focal surface equation for the slide determined as shown in FIG. 29, and is a modification of the value of the focus axis coordinate corresponding to the new position in an amount equal to the change in predicted focal plane from the previously imaged position to the new position.

If the new position corresponds to a point which is within more than one fine focus jurisdiction, then the determination of step 286 is negative, and step 288 of FIG. 31 prescribes the use of a weighted average of the corresponding focus axis coordinate values, corrected for tilt as discussed above. This step involves the use of an inverse distance weighting function to determine the in-focus value at the new point, such that the focus axis coordinate corresponding to the jurisdiction whose center is closer/closest to the new point is more heavily weighted than (any of) the focus axis coordinate(s) corresponding to the other jurisdiction(s) in which the new point lies.

After an appropriate focus axis coordinate is determined for the new point, a region about the point is imaged in this embodiment, as shown in step 292 of FIG. 31. Then, in step 294, it is determined whether substantially all of an area of interest—here, a cell spot—has been imaged. If so, the scan pass for this slide is complete, step 298. If not, step 296 prescribes a move along the scan axis to a new point. Step 300 determines whether this point is within the cell spot, and if not, step 302 calls for the repositioning to a new index axis coordinate within the cell spot. In this embodiment, the cell spot is considered made up of a center area and an edge area. For points inside the edge area, in this embodiment, an arc detect is used so that arcs indicating the edge of a cell spot are not used in any analysis, and frames that are believed to contain an arc are still imaged and may be analyzed.

In this embodiment, the scan pass process continues as shown in FIG. 31, with a determination made at each successive point of whether the point lies within a previously-determined fine focus jurisdiction, followed by the appropriate use of retrieved focus axis coordinates or the performance of fine focus actions at that point.

The pattern shown in the cell spot 202 of FIG. 28 represents the steps of the scan pass procedure of FIG. 31 completed over the entire cell spot. In this embodiment, an initial coarse focus action is taken at the center of the cell spot and the corresponding region is imaged. Since a focus action was taken, an area of fine focus jurisdiction is determined about this point, and the value of the focus axis coordinate corresponding to this area is associated with points within this area. Then, the stage is moved to a position about 370 µm below the center of the cell spot, along the scan axis. It is determined that this point lies within the fine focus jurisdiction of the first point, so no fine focus action is taken here. The focus axis coordinate of the first point is used to image the second point, corrected for tilt. Moves continue along the scan axis until a point is reached outside the area of jurisdiction of the initial point. Then, a fine focus action is performed at that point, and a new area of jurisdiction is determined. Moves continue until the edge of the cell spot is reached. A move is now made along the index axis to a new index axis coordinate, and moves continue along the scan index in an direction opposite that taken in the first line of moves along the scan axis. The process continues until one half of the cell spot is imaged, and the process continues again from the center extending in the opposite direction along the scan axis to that taken in the first line of moves from the center. The process continues until the entirety of the cell spot is imaged.

In one embodiment, to expedite identification of focus axis coordinates correlated with fine focus jurisdictions applicable at a specific location, the cell spot area (area of interest of the slide) is partitioned into bins. The bins represent rectangular regions of the cell spot area. Every fine focus jurisdiction that intersects a bin is put into the bin. Thus, a search for focus axis coordinates correlated with fine focus jurisdictions applicable at a specific location can be limited to those coordinates that are assigned to the bin wherein the specific location resides.

An embodiment of the invention includes numerous checks to ensure that the focus axis is tracking well to the in-focus plane. These include the establishment of absolute maximum and minimum focus axis values that are beyond the reasonable limit for an in-focus image; application of a maximum threshold to the value of the slope of the global focal surface as predicted by the fiducial mark locations; establishment of an out-of-bounds test for focus actions based upon the global focal surface as predicted by the fiducial mark locations; application of fiducial mark verification tolerances that demand that the location of the fiducial mark at the end of cell spot processing be within a particular distance from the initial search at the beginning of cell spot processing; establishment of a minimal focus score for both coarse and fine focus actions such that images scoring below this threshold are not judged as in-focus; establishment of a minimal number of fine focus actions that must occur across a cell spot; and establishment of a maximum percentage of fine focus actions that can occur at the extremes of the fine focus search region (±8 µm). Additionally, the embodiment may include the use of a checksum variable to account for each movement along the focus axis, in order to mitigate against data corruption associated with fine focus actions and cell spot partitioning.

In a further embodiment, after the acquired slide images have been processed, the data is reduced to a collection of Objects of Interest, which may merit further analysis by a cytotechnologist. The objects of interest are first ranked to determine the top 100 most important objects of interest. Once the top 100 objects of interest are sorted by importance, the objects of interest are mapped to slide coordinates. Once the mapping occurs, FOIs are computed. The FOIs are then organized to present an efficient path, using the Traveling Salesman (Hungarian) algorithm, for review by the cytotechnologist at the reviewing station.

The invention may be embodied in other specific forms without departing from the spirit or essential characteristics thereof. For example, the invention may be embodied in methods pertaining to electron microscope focusing systems. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

Having described certain preferred and exemplary embodiments of the invention, it will be apparent to those of ordinary skill in the art that other embodiments incorporating the concepts disclosed herein can be used without departing from the spirit and the scope of the invention. The described embodiments are to be considered in all respects only as illustrative and not limiting. Therefore, it is intended that the scope of the present invention be only limited by the following claims.

What is claimed is:

1. An automatic focusing method for an optical system, comprising:
    performing an initial coarse focus action along a focal axis at a scan position corresponding to a point on a surface of a slide; and
    respectively performing a plurality of subsequent fine focus actions along a plurality of focal axes at a plurality of scan positions corresponding to different points on the slide surface, wherein the performance of at least one of the fine focus actions comprises obtaining images of the slide, each of which has a two-dimensional array of pixels, at a plurality of coordinates within a predetermined range along the respective focal axis, and selecting one of the plurality of coordinates as a fine in-focus coordinate based on an examination of the pixel arrays of the images, wherein the slide comprises at least three fiducial points, and the method further comprises determining positions of the at least three fiducial points, and determining a scan axis slope, index axis slope, and focus intersect of a global focal plane based on the positions of the at least three fiducial points, wherein the Performance of the at least one of the fine focus actions comprises estimating an initial coordinate along the respective focal axis as a function of the global focal plane.

2. The method of claim 1, wherein the coordinates are evenly distributed within the predetermined range.

3. The method of claim 1, wherein the performance of the coarse focus action comprises determining a coarse in-focus coordinate along the focal axis.

4. The method of claim 3, wherein the performance of the at least one of the fine focus actions is based on the coarse in-focus coordinate.

5. The method of claim 1, wherein the performance of the coarse focus action comprises repeatedly obtaining an image of the slide at different coordinates along the focal axis until a coarse in-focus coordinate is determined.

6. The method of claim 5, wherein the performance of the coarse focus action comprises stepping the imaging between the different coordinates along the focal axis, wherein a step size of the imaging is gradually reduced, and wherein the coarse in-focus coordinate is determined at the smallest step size.

7. The method of claim 1, wherein the performance of the at least one of the fine focus actions comprises obtaining images of the slide at predetermined coordinates relative to the estimated initial coordinate along the respective focal axis.

8. The method of claim 1, wherein the performance of at least one of the coarse focus action and each fine focus action comprises:
obtaining images of the slide at a plurality of coordinates along the focal axis;
determining a plurality of focus scores for the respective coordinates; and
selecting one of the coordinates as an in-focus coordinate based on the focus scores.

9. The method of claim 8, wherein the coordinate having a maximum focus score is the coordinate selected as the in-focus coordinate.

10. The method of claim 1, wherein the slide carries a biological specimen.

11. The method of claim 1, wherein the coarse focus action and fine focus actions are performed during a single image scan.

12. The method of claim 1, wherein the performance of one or both of the coarse focus action and fine focus actions comprises moving an element of the optical system relative to the slide surface to coordinates along the respective focal axes.

13. The method of claim 1, wherein the performance of the fine focus actions comprises moving an element of the optical system relative to the slide along a scan axis to the respective scan positions.

14. The method of claim 1, wherein each of the images has a 640×480 pixel array size.

15. The method of claim 1, wherein the examination of each of the pixel arrays comprises comparing pixels to each other.

16. The method of claim 15, wherein the pixel comparison comprises comparing gray scale values of the pixels.

17. The method of claim 16, wherein the gray scale value comparison comprises comparing gray scale values between pairs of pixels separated by a fixed number of pixels.

18. The method of claim 1, wherein the examination of each of the pixel arrays comprises determining a focus score, and wherein the coordinate corresponding to the pixel array having the highest focus score is selected as the in-focus coordinate.

19. The method of claim 18, wherein the focus score for each of the pixel arrays is determined in accordance with the equation:

$$f(z) = \sum_j \sum_i (G_i(z) - G_{i+n}(z))^2,$$

where I is an index ranging over all imaging points, in order, along a scan line j, n is an integer, z is a position along the focal axis, $G_i$, is the transmission gray level between pairs of points separated by n pixels, and f(z) is the focus score.

20. The method of claim 1, wherein the at least one of the fine focus actions comprises the plurality of fine focus actions.

21. A review station, comprising:
a motorized stage coupled to the optical instrument for receiving a specimen;
an optical instrument having an optical path, the motorized stage configured for moving the specimen within the optical path, the optical instrument configured for performing an initial coarse focus action along a focal axis at the scan position corresponding to a point on the specimen, and respectively performing a plurality of subsequent fine focus actions along a plurality of focal axes at a plurality of scan positions corresponding to different points on the specimen;
a camera configured for obtaining images of the specimen along the optical path at a plurality of coordinates within a predetermined range along the respective focal axis during the performance of at least one of the fine focus actions, each of the images having a two-dimensional array of pixels; and
a processor configured for selecting one of the plurality of coordinates as a fine in-focus coordinate for at least one of the fine focus action based on an examination of the pixel arrays of the images, wherein the specimen comprises at least three fiducial points, and the processor is further configured for determining positions of the at least three fiducial points, and determining a scan axis slope, index axis slope, and focus intersect of a global focal plane based on the positions of the at least three fiducial points, wherein processor is further configured for estimating an initial coordinate along the respective focal axis as a function of the global focal plane for the at least one fine focus action.

22. The review station of claim 21, wherein the coordinates are evenly distributed within the predetermined range.

23. The review station of claim 21, wherein the performance of the coarse focus action comprises determining a coarse in-focus coordinate along the focal axis.

24. The review station of claim 21, wherein the performance of the at least one of the fine focus actions is based on the coarse in-focus coordinate.

25. The review station of claim 21, wherein the camera is configured for repeatedly obtaining an image of the specimen at different coordinates along the focal axis until a coarse in-focus coordinate is determined during the performance of the coarse focus action.

26. The review station of claim 25, wherein the camera is configured for stepping the imaging between the different coordinates along the focal axis during the performance of the coarse focus action, wherein a step size of the imaging is gradually reduced, and wherein the processor is configured for determining the coarse in-focus coordinate at the smallest step size.

27. The review station of claim 21, wherein the camera is configured for obtaining images of the specimen at predetermined coordinates relative to the estimated initial coordinate along the respective focal axis when the at least one of the fine focus actions is performed.

28. The review station of claim 21, wherein, during the performance of at least one of the coarse focus action and each fine focus action, the camera is configured for obtaining images of the specimen at a plurality of coordinates along the focal axis, and the processor is configured for determining a plurality of focus scores for the respective coordinates, and selecting one of the coordinates as an in-focus coordinate based on the focus scores.

29. The review station of claim 28, wherein the coordinate having a maximum focus score is the coordinate selected as the in-focus coordinate.

30. The review station of claim 21, wherein the specimen is carried by a slide.

31. The review station of claim 21, wherein the optical instrument is configured for performing the coarse focus action and fine focus actions during a single image scan.

32. The review station of claim 21, wherein each of the images has a 640×480 pixel array size.

33. The review station of claim 21, wherein the examination of each of the pixel arrays comprises comparing pixels to each other.

34. The review station of claim 33, wherein the pixel comparison comprises comparing gray scale values of the pixels.

35. The review station of claim 34, wherein the gray scale value comparison comprises comparing gray scale values between pairs of pixels separated by a fixed number of pixels.

36. The review station of claim 21, wherein the examination of each of the pixel arrays comprises determining a focus score, and wherein the coordinate corresponding to the pixel array having the highest focus score is selected as the in-focus coordinate.

37. The review station of claim 36, wherein the focus score for each of the pixel arrays is determined in accordance with the equation:

$$f(z) = \sum_j \sum_i (G_i(z) - G_{i+n}(z))^2,$$

where i is an index ranging over all imaging points, in order, along a scan line j, n is an integer, z is a position along the focal axis, $G_i$, is the transmission gray level between pairs of points separated by n pixels, and f(z) is the focus score.

38. The review station of claim 21, wherein the at least one of the fine focus actions comprises the plurality of fine focus actions.

* * * * *